United States Patent [19]

Iwamoto et al.

[11] Patent Number: 5,376,634
[45] Date of Patent: Dec. 27, 1994

[54] POLYPEPTIDE COMPOUND AND A PROCESS FOR PREPARATION THEREOF

[75] Inventors: Toshiro Iwamoto, Tsukuba; Akihiko Fujie, Tsuchiura; Kumiko Nitta, Tsuchiura; Yasuhisa Tsurumi; Nobuharu Shigematsu, both of Tsukuba; Chiyoshi Kasahara, Ikeda; Motohiro Hino, Tsuchiura; Masakuni Okuhara, Tsukuba; Kazuo Sakane, Kawanishi; Kohji Kawabata, Kawanishi; Hidenori Ohki, Ikeda, all of Japan

[73] Assignee: Fujisawa Pharmaceutical Co., Ltd., Osaka, Japan

[21] Appl. No.: 715,961

[22] Filed: Jun. 17, 1991

[30] Foreign Application Priority Data

Jun. 18, 1990 [GB] United Kingdom ............... 9013558
Oct. 31, 1990 [GB] United Kingdom ............... 9023666
Jan. 24, 1991 [GB] United Kingdom ............... 9101552

[51] Int. Cl.$^5$ .................. C07K 5/12; C07K 7/06; A61K 37/02
[52] U.S. Cl. ........................... 514/9; 514/11; 530/317
[58] Field of Search .............. 530/317; 514/9, 11

[56] References Cited

U.S. PATENT DOCUMENTS

| | | | |
|---|---|---|---|
| 4,293,482 | 10/1981 | Abbott et al. | 530/317 |
| 4,293,484 | 10/1981 | Debono | 530/317 |
| 4,293,488 | 10/1981 | Debono | 530/317 |
| 4,293,489 | 10/1981 | Debono | 530/317 |
| 4,791,100 | 12/1988 | Kramer et al. | 514/12 |

FOREIGN PATENT DOCUMENTS

| | | |
|---|---|---|
| 0031220 | 7/1981 | European Pat. Off. . |
| 0031662 | 8/1981 | European Pat. Off. . |
| 0311193 | 4/1989 | European Pat. Off. . |
| 0359529 | 3/1990 | European Pat. Off. . |
| 0431350 | 6/1991 | European Pat. Off. . |
| 0448354 | 9/1991 | European Pat. Off. . |
| 2066263 | 11/1980 | United Kingdom . |

Primary Examiner—Robert J. Hill, Jr.
Assistant Examiner—S. G. Marshall
Attorney, Agent, or Firm—Oblon, Spivak, McClelland, Maier & Neustadt

[57] ABSTRACT

A polypeptide compound having antimicrobial activity of the following general formula:

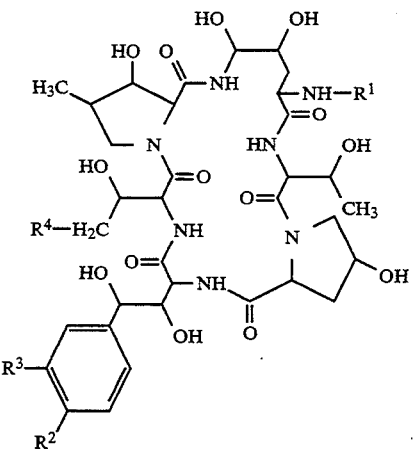

wherein $R^1$ is hydrogen or acyl group,
$R^2$ is hydroxy or acyloxy,
$R^3$ is hydroxysulfonyloxy, and
$R^4$ is hydrogen or carbamoyl,
with proviso that
$R^1$ is not palmitoyl, when $R^2$ is hydroxy,
$R^3$ is hydroxysulfonyloxy and
$R^4$ is carbamoyl,
and a pharmaceutically acceptable salt thereof.

11 Claims, No Drawings

POLYPEPTIDE COMPOUND AND A PROCESS FOR PREPARATION THEREOF

The present invention relates to new polypeptide compound and a pharmaceutically acceptable salt thereof.

More particularly, it relates to new polypeptide compound and a pharmaceutically acceptable salt thereof, which have antimicrobial activities (especially antifungal activities), to a process for preparation thereof, to pharmaceutical composition comprising the same, and to a method for treating or preventing infectious diseases in human being or animals.

Accordingly, one object of the present invention is to provide the polypeptide compound and a pharmaceutically acceptable salt thereof, which are highly active against a number of pathogenic microorganisms in human being and animals.

Another object of the present invention is to provide a process for the preparation of the polypeptide compound and a salt thereof.

A further object of the present invention is to provide a pharmaceutical composition comprising, as an active ingredient, said polypeptide compound or a pharmaceutically acceptable salt thereof.

Still further object of the present invention is to provide a method for treating or preventing infectious diseases caused by pathogenic microorganisms, which comprises administering said polypeptide compound to human being or animals.

The object polypeptide compound of the present invention is novel and can be represented by the following general formula [I] (SEQ ID NO: 1):

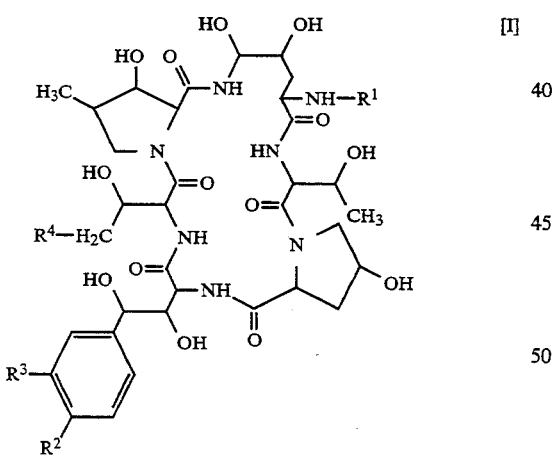

wherein
$R^1$ is hydrogen or acyl group,
$R^2$ is hydroxy or acyloxy,
$R^3$ is hydrogen or hydroxysulfonyloxy, and
$R^4$ is hydrogen or carbamoyl,
with proviso that
(i) $R^2$ is acyloxy, when $R^3$ is hydrogen, and
(ii) $R^1$ is not palmitoyl, when $R^2$ is hydroxy, $R^3$ is hydroxysulfonyloxy and $R^4$ is carbamoyl.

The polypeptide compound [I] (SEQ ID NO: 1) of the present invention can be prepared by the processes as illustrated in the following schemes.

Process 1

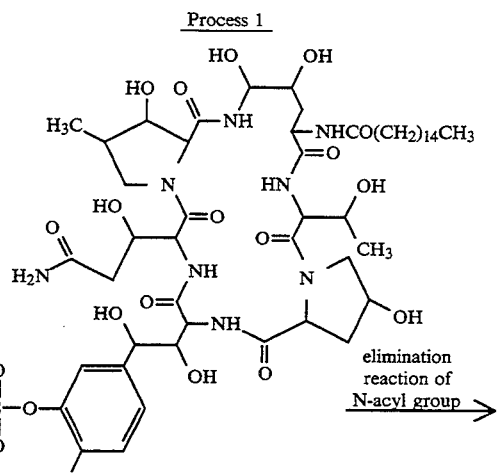

[II] (SEQ ID NO: 1)
or a salt thereof elimination reaction of N-acyl group →

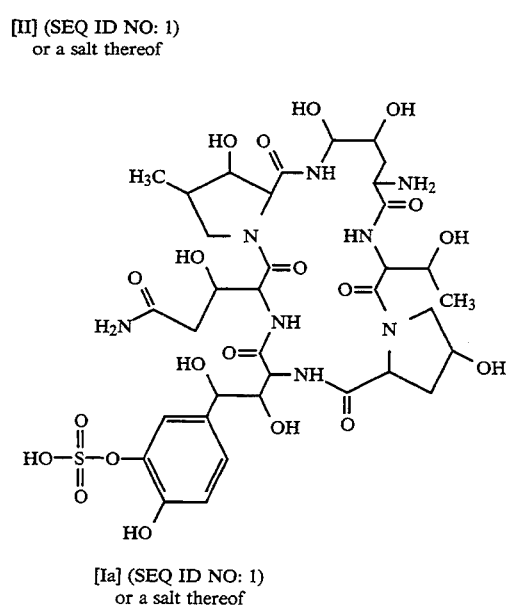

[Ia] (SEQ ID NO: 1)
or a salt thereof

Process 2

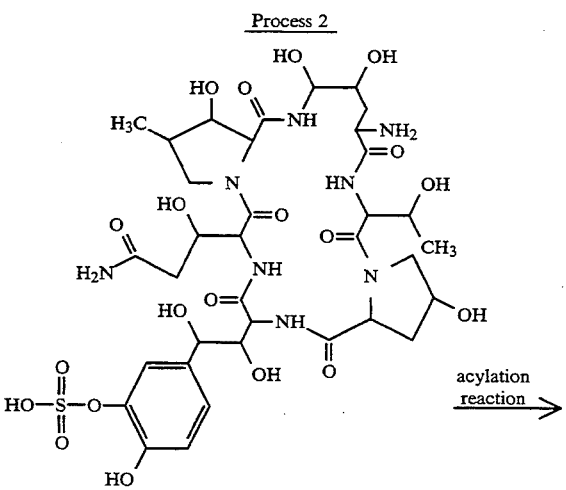

[Ia] (SEQ ID NO: 1)
or a salt thereof acylation reaction →

Process 2
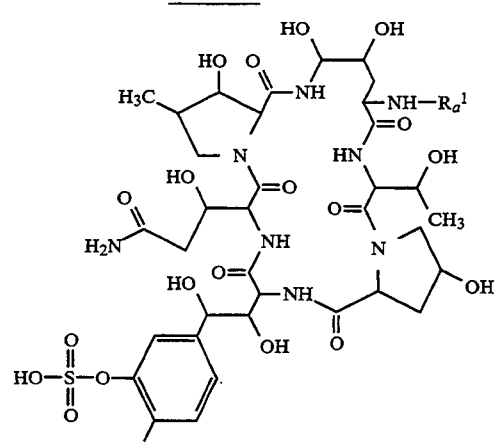
[Ib] (SEQ ID NO: 1)
or a salt thereof
Process 3
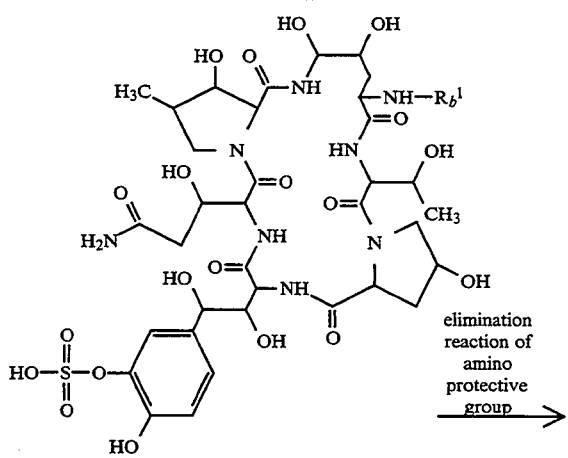
[Ic] (SEQ ID NO: 1)
or a salt thereof
→ elimination reaction of amino protective group
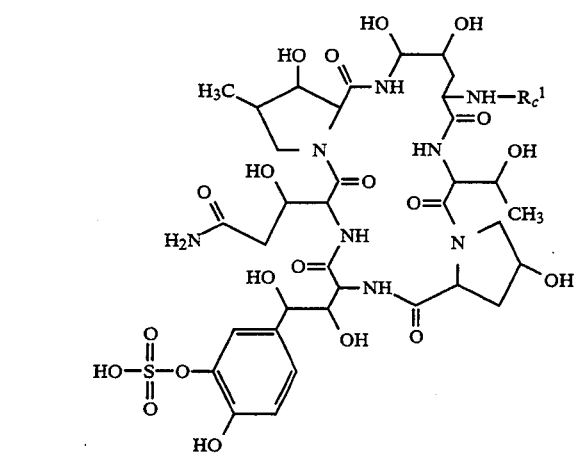
[Id] (SEQ ID NO: 1)
or a salt thereof
Process 4
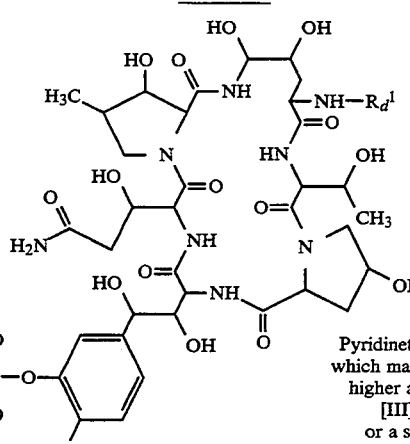
[Ie] (SEQ ID NO: 1)
or a salt thereof
→ Pyridinethione which may have higher alkyl [III] or a salt thereof
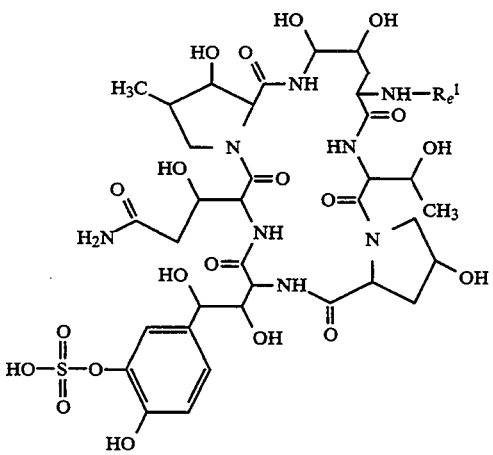
[If] (SEQ ID NO: 1)
or a salt thereof
Process 5
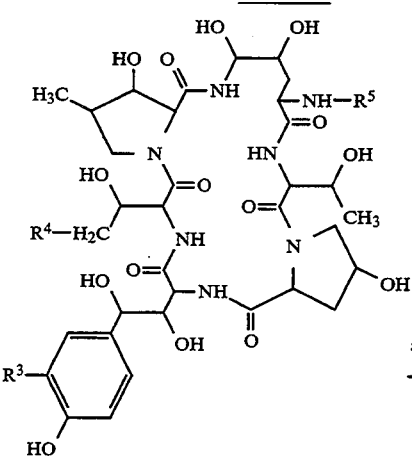
[IV] (SEQ ID NO: 1)
or a salt thereof
→ acylation reaction -continued
Process 5

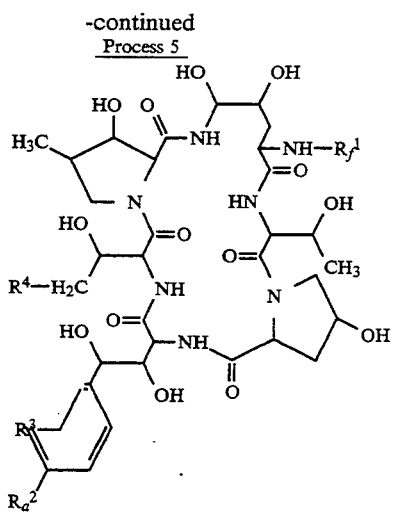

[Ig] (SEQ ID NO: 1)
or a salt thereof wherein
R³ and R⁴ are each as defined above,
$R_a^1$ is acyl group exclusive of palmitoyl,
$R_b^1$ is ar(lower)alkanoyl which has higher alkoxy and protected amino,
$R_c^1$ is ar(lower)alkanoyl which has higher alkoxy and amino,
$R_d^1$ is halo(lower)alkanoyl,
$R_e^1$ is pyridylthio(lower)alkanoyl which may have higher alkyl,
$R_f^1$ is acyl,
$R_a^2$ is acyloxy, and
$R^5$ is acyl group.

The starting compound [II] (SEQ ID NO: 1) or a salt thereof is novel and can be prepared by the following fermentation process.

Process A

A strain belonging
to the Coleophoma
which is capable    fermentation
of producing the    ⎯⎯⎯⎯⎯⎯→
compound [II] or
a salt thereof

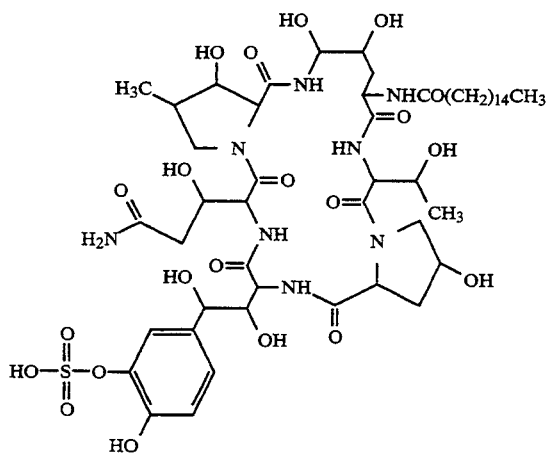

[II] (SEQ ID NO: 1)
or a salt thereof

Some of the starting compound [IV] are novel and can be prepared according to the aforesaid Process 1 to 4.

Suitable pharmaceutically acceptable salt of the object compound [I] (SEQ ID NO: 1) is conventional non-toxic mono or di salts and include a metal salt such as an alkali metal salt [e.g. sodium salt, potassium salt, etc.] and an alkaline earth metal salt [e.g. calcium salt, magnesium salt, etc.], an ammonium salt, an organic base salt [e.g. trimethylamine salt, triethylamine salt, pyridine salt, picoline salt, dicyclohexylamine salt, N,N-dibenzylethylenediamine salt, etc.] an organic acid addition salt [e.g. formate, acetate, trifluroacetate, maleate, tartrate, methanesulfonate, benzenesulfonate, toluenesulfonate, etc.], an inorganic acid addition salt e.g. hydrochloride, hydrobromide, hydroiodide, sulfate, phosphate, etc.], a salt with an amino acid [e.g. arginine salt, aspartic acid salt, glutamic acid salt, etc.], and the like.

In the above and subsequent description of this specification, suitable examples of the various definitions are explained in detail as follows:

The term "lower" is intended to mean 1 to 6 carbon atom(s), unless otherwise indicated.

The term "higher" is intended to mean 7 to 20 carbon atoms, unless otherwise indicated.

Suitable "acyl group" may be aliphatic acyl, aromatic acyl, heterocyclic acyl, arylaliphatic acyl and heterocyclic-aliphatic acyl derived from carboxylic acid, carbonic acid, carbamic acid, sulfonic acid, and the like.

Suitable example of the "acyl group" thus explained may be:

lower alkanoyl [e.g. formyl, acetyl, propionyl, butyryl, isobutyryl, valeryl, hexanoyl, pivaloyl, etc.] which may have one or more (preferably 1 to 3) suitable substituent(s) such as halogen (e.g. fluoro, chloro, bromo, iodo); aryl (e.g. phenyl, naphthyl, anthryl, etc.) which may have one or more (preferably 1 to 3) suitable substituent(s) like hydroxy, higher alkoxy as explained below, aforesaid aryl, or the like; lower alkoxy as explained below; amino; protected amino, preferably, acylamino such as lower alkoxycarbonylamino (e.g. methoxycarbonylamino, ethoxycarbonylamino, propoxycarbonylamino, butoxycarbonylamino, t-butoxycarbonylamino, pentyloxycarbonylamino, hexyloxycarbonylamino, etc.); or the like; di(lower)alkylamino (e.g. dimethylamino, N-methylethylamino, diethylamino, N-propylbutylamino, dipentylamino, dihexylamino, etc.); lower alkoxyimino (e.g. methoxyimino, ethoxyimino, propoxyimino, butoxyimino, t-butoxyimino, pentyloxyimino, hexyloxyimino, etc.); ar(-lower)alkoxyimino such as phenyl(lower)alkoxyimino (e.g. benzyloxyimino, phenethyloxyimino, benzhydryloxyimino, etc.) which may have one or more (preferably 1 to 3) suitable substituent(s) like higher alkoxy as explained below, or the like; heterocyclicthio, preferably, pyridylthio, which may have one or more (preferably 1 to 3) suitable substituent(s) like higher alkyl (e.g. heptyl, octyl, 2-ethylhexyl, nonyl, decyl, 3,7-dimethyloctyl, undecyl, dodecyl, tridecyl, tetradecyl, pentadecyl, 3-methyl-10-ethyldodecyl, hexadecyl, heptadecyl, octadecyl, nonadecyl, icosyl, etc.), or the like; heterocyclic group (e.g. thienyl, imidazolyl, pyrazolyl, furyl, tetrazolyl, thiazolyl, thiadiazolyl, etc.) which may have one or more (preferably 1 to 3) suitable substituent(s) like amino, aforesaid protected amino, aforesaid higher alkyl, or the like; or the like;

higher alkanoyl [e.g. heptanoyl, octanoyl, nonanoyl, decanoyl, undecanoyl, lauroyl, tridecanoyl, myristoyl, pentadecanoyl, palmitoyl, 10,12-dimethyltetradecanoyl, heptadecanoyl, stearoyl, nonadecanoyl, icosanoyl, etc.];

lower alkenoyl [e.g. acryloyl, methacryloyl, crotonoyl, 3-pentenoyl, 5-hexenoyl, etc.] which may have one or more (preferably 1 to 3) suitable substituent(s) such as aforesaid aryl which may have one or more (preferably 1 to 3) suitable substituent(s) like higher alkoxy as explained below, or the like, or the like;

higher alkenoyl [e.g. 4-heptenoyl, 3-octenoyl, 3,6-decadienoyl, 3,7,11-trimethyl-2,6,10-dodecatrienoyl, 4,10-heptadecadienoyl, etc.];

lower alkoxycarbonyl [e.g. methoxycarbonyl, ethoxycarbonyl, propoxycarbonyl, butoxycarbonyl, t-butoxycarbonyl, pentyloxycarbonyl, hexyloxycarbonyl, etc.];

higher alkoxycarbonyl [e.g. heptyloxycarbonyl, octyloxycarbonyl, 2-ethylhexyloxycarbonyl, nonyloxycarbonyl, decyloxycarbonyl, 3,7-dimethyloctyloxycarbonyl, undecyloxycarbonyl, dodecyloxycarbonyl, tridecyloxycarbonyl, tetradecyloxycarbonyl, pentadecyloxycarbonyl, 3-methyl-10-ethyldodecyloxycarbonyl, hexadecyloxycarbonyl, heptadecyloxycarbonyl, octadecyloxycarbonyl, nonadecyloxycarbonyl, icosyloxycarbonyl, etc.];

aryloxycarbonyl [e.g. phenoxycarbonyl, naphthyloxycarbonyl, etc.];

arylglyoxyloyl [e.g. phenylglyoxyloyl, naphthylglyoxyloyl, etc.];

ar(lower)alkoxycarbonyl which may have one or more suitable substituent(s) such as phenyl(lower)alkoxycarbonyl which may have nitro or lower alkoxy [e.g. benzyloxycarbonyl, phenethyloxycarbonyl, p-nitrobenzyloxycarbonyl, p-methoxybenzyloxycarbonyl, etc.];

lower alkylsulfonyl [e.g. methylsulfonyl, ethylsulfonyl, propylsulfonyl, isopropylsulfonyl, pentylsulfonyl, butylsulfonyl, etc.];

arylsulfonyl [e.g. phenylsulfonyl, naphthylsulfonyl, etc.] which may have one or more (preferably 1 to 3) suitable substituent(s) such as lower alkyl as explained below, higher alkoxy as explained below, or the like;

ar(lower)alkylsulfonyl such as phenyl(lower)alkylsulfonyl [e.g. benzylsulfonyl, phenethylsulfonyl, benzhydrylsulfonyl, etc.], or the like;

aroyl [e.g. benzoyl, naphthoyl, anthrylcarbonyl, etc.] which may have one or more (preferably 1 to 5) suitable substituent(s) such as aforesaid halogen; lower alkyl (e.g. methyl, ethyl, propyl, butyl, t-butyl, pentyl, hexyl, etc.); aforesaid higher alkyl; lower alkoxy (e.g. methoxy, ethoxy, propoxy, butoxy, t-butoxy, pentyloxy, hexyloxy, etc.) which may have one or more (preferably 1 to 10) suitable substituent(s) like aforesaid lower alkoxy, aforesaid halogen, aforesaid aryl, or the like; higher alkoxy (e.g. heptyloxy, octyloxy, 2-ethylhexyloxy, nonyloxy, decyloxy, 3,7-dimethyloctyloxy, undecyloxy, dodecyloxy, tridecyloxy, tetradecyloxy, pentadecyloxy, 3-methyl-10-ethyldodecyloxy, hexadecyloxy, heptadecyloxy, octadecyloxy, nonadecyloxy, icosyloxy, etc.) which may have one or more (preferably 1 to 17) suitable substituent(s) like aforesaid halogen; higher alkenyloxy (e.g. 3-heptenyloxy, 7-octenyloxy, 2,6-octadienyloxy, 5-nonenyloxy, 1-decenyloxy, 3,7-dimethyl-6-octenyloxy, 3,7-dimethyl-2,6-octadienyloxy, 8-undecenyloxy, 3,6,8-dodecatrienyloxy, 5-tridecenyloxy, 7-tetradecenyloxy, 1,8-pentadecadienyloxy, 15-hexadecenyloxy, 11-heptadecenyloxy, 7-octadecenyloxy, 10-nonadecenyloxy, 18-icosenyloxy, etc.); carboxy; aforesaid aryl which may have one or more (preferably 1 to 3) suitable substituent(s) like aforesaid higher alkoxy; aryloxy (e.g. phenoxy, naphthyloxy, anthryloxy, etc.) which may have one or more (preferably 1 to 3) suitable substituent(s) like aforesaid lower alkoxy, or aforesaid higher alkoxy; or the like; or the like.

In said "acyl group", the preferred one may be lower alkanoyl; halo(lower)alkanoyl;

ar(lower)alkanoyl which may have one or more (preferably 1 to 3) hydroxy, lower alkoxy, higher alkoxy, aryl, amino, protected amino, di(lower)alkylamino, lower alkoxyimino or ar(lower)alkoxyimino which may have one or more (preferably 1 to 3) higher alkoxy;

heterocyclicthio(lower)alkanoyl which may have one or more (preferably 1 to 3) higher alkyl;

heterocyclic(lower)alkanoyl which may have one or more (preferably 1 to 3) lower alkoxyimino, higher alkyl, amino or protected amino;

ar(lower)alkoxyimino(lower)alkanoyl which may have one or more (preferably 1 to 3) higher alkoxy;

higher alkanoyl;

ar(lower)alkenoyl which may have one or more (preferably 1 to 3) higher alkoxy;

higher alkenoyl; lower alkoxycarbonyl; higher alkoxycarbonyl; aryloxycarbonyl;

arylsulfonyl which may have one or more (preferably 1 to 3) lower alkyl or higher alkoxy;

aroyl which may have one or more (preferably 1 to 5) halogen, lower alkyl, higher alkyl, carboxy, lower alkoxy which may have one or more (preferably 1 to 10) halogen, lower alkoxy(lower)alkoxy, ar(lower)alkoxy, higher alkoxy which may have one or mare (preferably 1 to 17) halogen, higher alkenyloxy, aryl which may have one or more (preferably 1 to 3) higher alkoxy or aryloxy which may have one or more (preferably 1 to 3) lower alkoxy or higher alkoxy;

in which the more preferred one may be lower alkanoyl; halo(lower)alkanoyl;

phenyl(lower)alkanoyl or naphthyl(lower)alkanoyl, each of which may have 1 to 3 hydroxy, lower alkoxy, higher alkoxy, phenyl, amino, lower alkoxycarbonylamino, di(lower)alkylamino, lower alkoxyimino, or phenyl(lower)alkoxyimino which may have 1 to 3 higher alkoxy;

pyridylthio(lower)alkanoyl which may have 1 to 3 higher alkyl;

imidazolyl(lower)alkanoyl or thiazolyl(lower)alkanoyl, each of which may have 1 to 3 lower alkoxyimino, higher alkyl, amino or lower alkoxycarbonylamino;

phenyl(lower)alkoxyimino(lower)alkanoyl which may have 1 to 3 higher alkoxy;

higher alkanoyl;

phenyl(lower) alkenoyl which may have 1 to 3 higher alkoxy;

higher alkenoyl; lower alkoxycarbonyl, higher alkoxycarbonyl; phenoxycarbonyl;

phenylsulfonyl or naphthylsulfonyl, each of which may have 1 to 3 lower alkyl or higher alkoxy;

benzoyl, naphthoyl or anthrylcarbonyl, each of which may have 1 to 5 halogen, lower alkyl, higher alkyl, carboxy, lower alkoxy which may have 6 to 10 halogen, lower alkoxy(lower)alkoxy, phenyl(lower)alkoxy, higher alkoxy which may have 12 to 17 halogen, higher alkenyloxy, phenyl which may have 1 to 3 higher alkoxy, phenoxy which may have 1 to 3 lower alkoxy or higher alkoxy;

the much more preferred one may be $(C_1-C_4)$alkanoyl; halo$(C_1-C_4)$alkanoyl;

phenyl(C₁-C₄)alkanoyl which may have 1 to 3 hydroxy, (C₁-C₄)alkoxy, (C₇-C₁₆)alkoxy, phenyl, amino, (C₁-C₄)alkoxycarbonylamino, di(C₁-C₄)alkylamino, (C₁-C₄)alkoxyimino or phenyl(C₁-C₄)alkoxyimino which may have (C₇-C₁₆)alkoxy;

naphthyl (C₁-C₄)alkanoyl which may have 1 to 3 (C₁-C₄)alkoxycarbonylamino;

1-(C₇-C₁₆)alkylpyridiniothio (C₁-C₄)alkanoyl;

imidazolyl(C₁-C₄)alkanoyl which may have 1 to 3 (C₇-C₁₆) alkyl or (C₁-C₄)alkoxycarbonylamino;

thiazolyl(C1-C4)alkanoyl which may have 1 to 3 (C₁-C₄)alkoxyimino or amino;

phenyl(C₁-C₄)alkoxyimino(C1-C₄)alkanoyl which may have 1 to 3 (C₇-C₁₆)alkoxy;

(C₇-C₁₇)alkyl;

phenyl(C₁-C₄)alkenoyl which may have 1 to 3 (C₇-C₁₆)alkoxy;

(C₇-C₁₈)alkenoyl; (C₃-C₆)alkoxycarbonyl; (C₇-C₁-₆)alkoxycarbonyl; phenoxycarbonyl;

phenylsulfonyl which may have (C₁-C₄)alkyl or (C₇-C₁₆)alkoxy;

naphthylsulfonyl which may have (C₇-C₁₆)alkoxy;

benzoyl which may have 1 to 5 halogen, (C₃-C₆)alkyl, (C₇-C₁₆)alkyl, carboxy, (C₁-C₆)alkoxy which may have 6 to 10 halogen, (C₁-C₄)alkoxy(C₁-C₄)alkoxy, phenyl (C₃-C₆)alkoxy, (C₇-C₁₆)alkoxy which may have 12 to 17 halogen, phenyl which may have 1 to 3 (C₇-C₁₆)alkoxy or phenoxy which may have 1 to 3 (C₃-C₆)alkoxy or (C7-C16)alkoxy;

naphthoyl which may have 1 to 3 (C₃-C₆)alkoxy, (C₇-C₁₆)alkoxy or (C₇-C₁₆)alkenyloxy;

anthrylcarbonyl;

and the most preferred one may be acetyl, 2-bromoacetyl, 2-(4-biphenylyl )acetyl, 2-(4-octyloxyphenyl)acetyl, 3-(4-octyloxyphenyl)propionyl, 2-amino-2-(4-octyloxyphenyl)acetyl, 2-(t-butoxycarbonylamino)-2-(4-octyloxyphenyl)acetyl, 2-amino-3-(4-octyloxyphenyl)propionyl, 2-(t-butoxycarbonylamino)-3-(4-octyloxyphenyl)propionyl, 2-dimethylamino-3-(4-octyloxyphenyl)propionyl, 2-(t-butoxycarbonylamino)-2-(2-naphthyl)acetyl, 2-methoxy-2-(4-octyloxyphenyl)acetyl, 2-methoxyimino-2-(4-octyloxyphenyl)acetyl, 2-(4-octyloxybenzyloxyimino)-2-(4-hydroxyphenyl)acetyl, 2-(4-octyloxybenzyloxyimino)-2-phenylacetyl, 2-(4-octyloxybenzyloxyimino)acetyl, 2-(1-octyl-4-pyridinio)thioacetyl, 2-methoxyimino-2-(2-aminothiazol-4-yl)acetyl, 2-(t-butoxycarbonylamino)-3-(1-octyl-4-imidazolyl)propionyl, 3-(4-octyloxyphenyl)acryloyl, 3,7,11-trimethyl-2,6,10-dodecatrienoyl, t-butoxycarbonyl, octyloxycarbonyl, phenoxycarbonyl, p-tolylsulfonyl, 4-octyloxyphenylsulfonyl, 6-octyloxy-2-naphthylsulfonyl, 4-(t-butyl)benzoyl, 4-octylbenzoyl, 2,3,5,6-tetrafluoro-4-(2,2,3,3,4,4,5,5-octafluoropentyloxy)benzoyl, 4-(2-butoxyethoxy)benzoyl, 4-(4-phenylbutoxy)benzoyl, 4-octyloxybenzoyl, 2-carboxy-4-octyloxybenzoyl, 3-methoxy-4-octyloxybenzoyl, 4-(2,2,3,3,4,4,5,5,6,6,7,7,8,8-pentadecafluorooctyloxy)-2,3,5,6-tetrafluorobenzoyl, 4-(4-octyloxyphenyl)benzoyl, 4-(4-octyloxyphenoxy)benzoyl, 6-butoxy-2-naphthoyl, 6-hexyloxy-2-naphthoyl, 6-octyloxy-2-naphthoyl, 6-(2-ethylhexyloxy)-2-naphthoyl, 6-decyloxy-2-naphthoyl, 6-(3,7-dimethyloctyloxy)-2-naphthoyl, 6-dodecyloxy-2-naphthoyl, 6-(3,7-dimethyl-6-octenyloxy)-2-naphthoyl, 6-(3,7-dimethyl-2,6-octadienyloxy)-2-naphthoyl, 2-anthrylcarbonyl), 4-(4-heptyloxyphenyl)benzoyl and 4-(4-hexyloxyphenoxy)benzoyl.

Suitable "acyl group exclusive of palmitoyl" can be referred to the ones as exemplified before for "acyl group" except palmitoyl.

Suitable "ar(lower)alkanoyl" moiety in "ar(lower)alkanoyl which has higher alkoxy and protected amino" and "ar(lower)alkanoyl which has higher alkoxy and amino" can be referred to the ones as exemplified before for "acyl group" and suitable examples of the substituent(s) "higher alkoxy" and "protected amino" can be referred to the ones as exemplified before for "acyl group".

Suitable "halo(lower)alkanoyl" can be referred to the ones as exemplified before for "acyl group".

Suitable "pyridylthio(lower)alkanoyl" in "pyridylthio(lower)alkanoyl which may have higher alkyl" can be referred to the ones as exemplified before for "acyl group", and suitable examples of the substituent "higher alkyl" can be exemplified before for "acyl group".

Suitable "acyloxy" may include hydroxysulfonyloxy, phosphonooxy, and the like.

In the object compound [I] (SEQ ID NO: 1) thus defined, the following compound [I] is especially preferable.

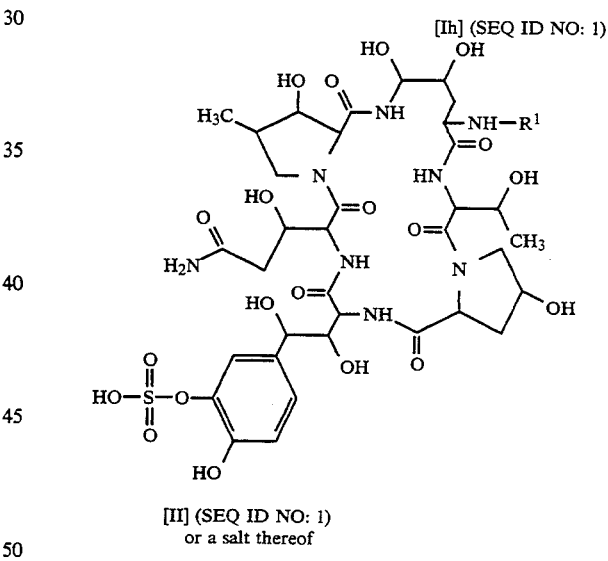

[Ih] (SEQ ID NO: 1)

[II] (SEQ ID NO: 1)
or a salt thereof wherein R¹ is hydrogen or acyl group, with proviso that R¹ is not palmitoyl.

Suitable "acylating agent" for the acylation reaction is Process 2 may be an acid compound corresponding to the acyl group to be introduced or its reactive derivative at the carboxy group or a salt thereof and suitable example of said acylating agent is represented by the formula:

$$R_a^1\text{—OH} \qquad [V]$$

wherein $R_a^1$ is as defined above or its reactive derivative at the carboxy group or a salt thereof.

In the compound [V], the following compounds are novel.

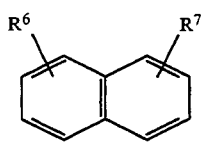

[V-1]
or its reactive derivative
at the carboxy group
or a salt thereof

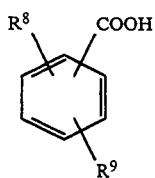

[V-2]
or its reactive derivative
at the carboxy group
or a salt thereof wherein $R^6$ is lower alkoxy, higher alkoxy or higher alkenyloxy, $R^7$ is —COOH or —SO$_3$H, $R^8$ is 1 to 4 halogen, $R^9$ is lower alkoxy which has one or more halogen, higher alkoxy which has one or more halogen.

The compounds [V-1] and [V-2] can be prepared by the following processes.

Process B

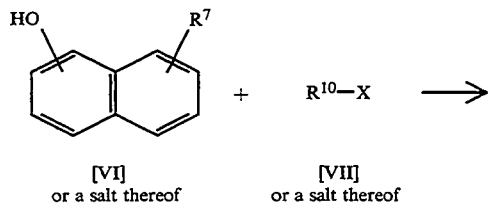

[VI]              [VII]
or a salt thereof   or a salt thereof

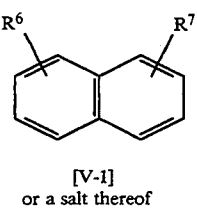

[V-1]
or a salt thereof

Process C

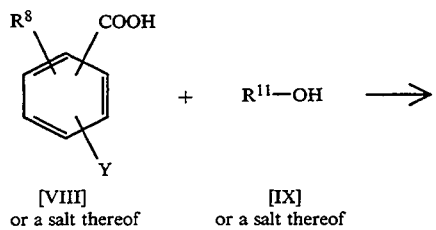

[VIII]             [IX]
or a salt thereof   or a salt thereof

①

②

-continued

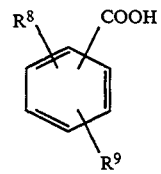

[V-2]
or a salt thereof wherein $R^6$, $R^7$, $R^8$ and $R^9$ are each as defined above $R^{10}$ is lower alkyl, higher alkyl or higher alkenyl, $R^{11}$ is lower alkyl which has one or more halogen or higher alkyl which has one or more halogen, and X and Y are each a leaving group.

In the above definitions, suitable "lower alkoxy", "higher alkoxy", "higher alkenyloxy", "halogen", "lower alkyl" and "higher alkyl" can be referred to the ones as exemplified before.

Suitable "higher alkenyl" may include 3-heptenyl, 7-octenyl, 2,6-octadienyl, 5-nonenyl, 1-decenyl, 3,7-dimethyl-6-octenyl, 3,7-dimethyl-2,6-octadienyl, 8-undecenyl, 3,6,8-dodecatrienyl, 5-tridecenyl, 7-tetradecenyl, 1,8-pentadecadienyl, 15-hexadecenyl, 11-heptadecenyl, 7-octadecenyl, 10-nonadecenyl, 18-icosenyl and the like, in which the preferred one may be ($C_7$-$C_{16}$)alkenyl.

As for $R^9$, "lower alkoxy" has one or more (preferably 1 to 10, more preferably 6 to 10) halogen, and "higher alkoxy" has one or more (preferably 1 to 17, more preferably 12 to 17) halogen.

As for $R^{11}$, "lower alkyl" has one or more (preferably 1 to 10, more preferably 6 to 10) halogen, and "higher alkyl" has one or more (preferably 1 to 17, more preferably 12 to 17)halogen.

As for $R^6$, preferred "lower alkoxy" may be ($C_4$-$C_6$)alkoxy.

Suitable "a leaving group" may include aforesaid halogen, lower alkanoyloxy (e.g. acetoxy, etc.), sulfonyloxy (e.g. mesyloxy, tosyloxy, etc.), and the like.

Regarding suitable salts and the reactive derivatives at the carboxy group of the compounds [V-1] and [V-2], they can be referred to the ones as exemplified below for the compound [V].

The reactions in Processes B and C can be carried out according to the methods disclosed later in Preparations of the present specification or the similar manners thereto.

In the compound [V], there are other novel compounds than compounds [V-1] and [V-2], and they can be prepared, for example, by the methods disclosed later in Preparations.

Suitable "pyridinethione" in Process 4 may include 1,2-dihydropyridine-2-thione, 1,4-dihydropyridine-4-thione, and the like, and said "pyridinethione" may have aforesaid "higher alkyl".

The processes for preparing the object compound [I] or a salt thereof of the present invention are explained in detail in the following.

PROCESS 1

The object compound [Ia] (SEQ ID NO: 1) or a salt thereof can be prepared by subjecting a compound [II] (SEQ ID NO: 1) or a salt thereof to elimination reaction of N-acyl group.

This reaction is carried out in accordance with a conventional method such as hydrolysis, reduction, reaction with an enzyme or the like.

The hydrolysis is preferably carried out in the presence of a base or an acid including Lewis acid. Suitable base may include an inorganic base and an organic base such as an alkali metal [e.g. sodium, potassium, etc.], an alkaline earth metal [e.g. magnesium, calcium, etc.], the hydroxide or carbonate or bicarbonate thereof, trialkylamine [e.g. trimethylamine, triethylamine, etc.], picoline, 1,5-diazabicyclo[4.3.0]non-5-ene, 1,4-diazabicyclo[2.2.2]octane, 1,8-diazabicyclo[5.4.0]undec-7-ene, or the like.

Suitable acid may include an organic acid [e.g. formic acid, acetic acid, propionic acid, trichloroacetic acid, trifluoroacetic acid, etc.] and an inorganic acid [e.g. hydrochloric acid, hydrobromic acid, sulfuric acid, hydrogen chloride, hydrogen bromide, etc.]. The elimination using Lewis acid such as trihaloacetic acid [e.g. trichloroacetic acid, trifluoroacetic acid, etc.] or the like is preferably carried out in the presence of cation trapping agents [e.g. anisole, phenol, etc.].

The reaction is usually carried out in a solvent such as water, an alcohol [e.g. methanol, ethanol, etc.], methylene chloride, tetrahydrofuran, a mixture thereof or any other solvent which does not adversely influence the reaction. A liquid base or acid can be also used as the solvent. The reaction temperature is not critical and the reaction is usually carried out under cooling to warming.

The reduction method applicable for the elimination reaction may include chemical reduction and catalytic reduction.

Suitable reducing agents to be used in chemical reduction are a combination of metal [e.g. tin, zinc, iron, etc.] or metallic compound [e.g. chromium chloride, chromium acetate, etc.] and an organic or inorganic acid [e.g. formic acid, acetic acid, propionic acid, trifluoroacetic acid, p-toluenesulfonic acid, hydrochloric acid, hydrobromic acid, etc.].

Suitable catalysts to be used in catalytic reduction are conventional ones such as platinum catalysts [e.g. platinum plate, spongy platinum, platinum black, colloidal platinum, platinum oxide, platinum wire, etc.], palladium catalysts [e.g. spongy palladium, palladium black, palladium oxide, palladium on carbon, colloidal palladium, palladium on barium sulfate, palladium on barium carbonate, etc.], nickel catalysts [e.g. reduced nickel, nickel oxide, Raney nickel, etc.], cobalt catalysts [e.g. reduced cobalt, Raney cobalt, etc.], iron catalysts [e.g. reduced iron, Raney iron, etc.], copper catalysts [e.g. reduced copper, Raney copper, Ullman copper, etc.] and the like.

The reduction is usually carried out in a conventional solvent which does not adversely influence the reaction such as water, methanol, ethanol, propanol, N,N-dimethylformamide, or a mixture thereof. Additionally, in case that the above-mentioned acids to be used-in chemical reduction are in liquid, they can also be used as a solvent. Further, a suitable solvent to be used in catalytic reduction may be the above-mentioned solvent, and other conventional solvent such as diethyl ether, dioxane, tetrahydrofuran, etc., or a mixture thereof.

The reaction temperature of this reduction is not critical and the reaction is usually carried out under cooling to warming.

The reaction with an enzyme can be carried out by reacting the compound [II] (SEQ ID NO: 1) or a salt thereof with an enzyme suitable for the elimination reaction of N-acyl group.

Suitable example of said enzyme may include the one produced by certain microorganisms of the Actinoplanaceae, for example, Actinoplanes utahensis IFO-13244, Actinoplanes utahensis ATCC 12301, Actinoplanes missourienses NRRL 12053, or the like; and the like.

This elimination reaction is usually carried out in a solvent such as phosphate buffer, Tris-HCl buffer or any other solvent which does not adversely influence the reaction The reaction temperature is not critical and the reaction can be carried out at room temperature or under warming.

PROCESS 2

The object compound [Ib] (SEQ ID NO: 1) or a salt thereof can be prepared by subjecting the compound [Ia] (SEQ ID NO: 1) or a salt thereof to acylation reaction.

The acylation reaction of this process can be carried out by reacting the compound [Ia] (SEQ ID NO: 1) or a salt thereof with aforesaid "acylating agent", for example, the compound [V] (SEQ ID NO: 1) or its reactive derivative at the carboxy group or a salt thereof.

Suitable reactive derivative at the carboxy group of the compound [V] may include an acid halide, an acid anhydride, an activated amide, an activated ester, and the like. Suitable examples of the reactive derivatives may be an acid chloride; an acid azide; a mixed acid anhydride with an acid such as substituted phosphoric acid [e.g. dialkylphosphoric acid, phenylphosphoric acid diphenylphosphoric acid, dibenzylphosphoric acid, halogenated phosphoric acid, etc.], dialkylphosphorous acid, sulfurous acid, thiosulfuric acid, sulfuric acid, sulfonic acid [e.g. methanesulfonic acid, etc.], aliphatic carboxylic acid [e.g. acetic acid, propionic acid, butyric acid, isobutyric acid, pivaric acid, pentanoic acid, isopentanoic acid, 2-ethylbutyric acid, trichloroacetic acid, etc.]; or aromatic carboxylic acid [e.g. benzoic acid, etc.]; a symmetrical acid anhydride; an activated amide with imidazole, 4-substituted imidazole, dimethylpyrazole, triazole, tetrazole or 1-hydroxy-1H-benzotriazole; or an activated ester [e.g. cyanomethyl ester, methoxymethyl ester, dimethyliminomethyl [(CH$_3$)$_2$N$^+$=CH—] ester, vinyl ester, propargyl ester, p-nitrophenyl ester, 2,4-dinitrophenyl ester, trichlorophenyl ester, pentachlorophenyl ester, mesylphenyl ester, phenylazophenyl ester, phenyl thioester, p-nitrophenyl thioester, p-cresyl thioester, carboxymethyl thioester, pyranyl ester, pyridyl ester, piperidyl ester, 8-quinolyl thioester, etc.], or an ester with a N-hydroxy compound [e.g. N,N-dimethylhydroxylamine, 1-hydroxy-2-(1H)-pyridone, N-hydroxysuccinimide, N-hydroxyphthalimide, 1-hydroxy-1H-benzotriazole, etc.], and the like. These reactive derivatives can optionally be selected from them according to the kind of the compound [V] (SEQ ID NO: 1) to be used.

Suitable salts of the compound [V] (SEQ ID NO: 1) and its reactive derivative can be referred to the ones as exemplified for the compound [I] (SEQ ID NO: 1).

The reaction is usually carried out in a conventional solvent such as water, alcohol [e.g. methanol, ethanol, etc.], acetone, dioxane, acetonitrile, chloroform, methylene chloride, ethylene chloride, tetrahydrofuran, ethyl acetate, N,N-dimethylformamide, pyridine or any other organic solvent which does not adversely influence the reaction. These conventional solvent may also be used in a mixture with water.

In this reaction, when the compound [V] (SEQ ID NO: 1) is used in a free acid form or its salt form, the reaction is preferably carried out in the presence of a conventional condensing agent such as N,N'-dicyclohexylcarbodiimide; N-cyclohexyl-N'-morpholinoethylcarbodiimide; N-cyclohexyl-N'-(4-diethylaminocyclohexyl)carbodiimide; N,N'-diethylcarbodiimide, N,N'-diisopropylcarbodiimide; N-ethyl-N'-(3-dimethylaminopropyl)carbodiimide, N,N'-carbonylbis-(2-methylimidazole); pentamethyleneketene-N-cyclohexylimine; diphenylketene-N-cyclohexylimine; ethoxyacetylene; 1-alkoxy-1-chloroethylene; trialkyl phosphite; ethyl polyphosphate; isopropyl polyphosphate; phosphorus oxychloride (phosphoryl chloride); phosphorus trichloride; thionyl chloride; oxalyl chloride; lower alkyl haloformate [e.g. ethyl chloroformate, isopropyl chloroformate, etc.]; triphenylphosphine; 2-ethyl-7-hydroxybenzisoxazolium salt; 2-ethyl-5-(m-sulfophenyl)isoxazolium hydroxide intramolecular salt; 1-(p-chlorobenzenesulfonyloxy)-6-chloro-1H-benzotriazole; so-called Vilsmeier reagent prepared by the reaction of N,N-dimethylformamide with thionyl chloride, phosgene, trichloromethyl chloroformate, phosphorus oxychloride, methanesulfonyl chloride, etc.; or the like.

The reaction may also be carried out in the presence of an inorganic or organic base such as an alkali metal carbonate, alkali metal bicarbonate, tri(lower)alkylamine, pyridine, di(lower)alkylaminopyridine (e.g. 4-dimethylaminopyridine, etc.), N-(lower)alkylmorpholine, N,N-di(lower)alkylbenzylamine, or the like.

The reaction temperature is not critical, and the reaction is usually carried out under cooling to warming.

PROCESS 3

The object compound [id] (SEQ ID NO: 1) or a salt thereof can be prepared by subjecting a compound [Ic] (SEQ ID NO: 1) or a salt thereof to elimination reaction of amino protective group.

Suitable salts of the compounds [Ic] (SEQ ID NO: 1) and [Id] (SEQ ID NO: 1) can be referred to the ones as exemplified for the compound [I] (SEQ ID NO: 1).

This elimination reaction can be carried out in accordance with a conventional method as explained above for Process 1.

PROCESS 4

The object compound [If] (SEQ ID NO: 1) or a salt thereof can be prepared by reacting a compound [Ie] (SEQ ID NO: 1) or a salt thereof with a compound [III] (SEQ ID NO: 1) or a salt thereof.

Suitable salt of the compound [If] (SEQ ID NO: 1) can be referred to the ones as exemplified for the compound [I] (SEQ ID NO: 1).

Suitable salt of the compound [III] (SEQ ID NO: 1) can be referred to acid addition salts as exemplified for the compound [I] (SEQ ID NO: 1).

The present reaction may be carried out in a solvent such as water, phosphate buffer, acetone, chloroform, acetonitrile, nitrobenzene, methylene chloride, ethylene chloride, formamide, N,N-dimethylformamide, methanol, ethanol, diethyl ether, tetrahydrofuran, dimethyl sulfoxide, or any other organic solvent which does not adversely affect the reaction, preferably in ones having strong polarities. Among the solvents, hydrophilic solvents may be used in a mixture with water. When the compound [III] (SEQ ID NO: 1) is in liquid, it can also be used as a solvent.

The reaction is preferably conducted in the presence of a base, for example, inorganic base such as alkali metal hydroxide, alkali metal carbonate, alkali metal bicarbonate, organic base such as trialkylamine, and the like.

The reaction temperature is not critical, and the reaction is usually carried out under cooling, at room temperature, under warming or under heating.

The present reaction is preferably carried out in the presence of alkali metal halide [e.g. sodium iodide, potassium iodide, etc.], alkali metal thiocyanate [e.g. sodium thiocyanate, potassium thiocyanate, etc.] or the like.

PROCESS 5

The object compound [Ig] (SEQ ID NO: 1) or a salt thereof can be prepared by subjecting a compound [IV] (SEQ ID NO: 1) or a salt thereof to acylation reaction.

Suitable salts of the compounds [Ig] (SEQ ID NO: 1) and [IV] (SEQ ID NO: 1) can be referred to the ones as exemplified for the compound [I] (SEQ ID NO: 1).

Suitable "acylating agent" in this Process 5 may be an acid compound corresponding to the acyl group to be introduced, for example, phosphoric acid and its derivative (e.g. phosphoryl chloride, diphenylphosphorochloridate, etc.), sulfuric acid and its derivative [e.g. sulfur trioxide-pyridine, sulfur trioxidetri(lower)alkylamine (e.g. trimethylamine, triethylamine, etc.), chlorosulfonic acid, etc.], or the like.

This reaction can be carried out in a conventional manner.

The process for preparing the starting compound [II] (SEQ ID NO: 1) or a salt thereof of the present invention is explained in detail in the following.

PROCESS A

The compound [II] (SEQ ID NO: 1) or a salt thereof can be prepared by the fermentation process.

The fermentation process is explained in detail in the following.

The compound [II] (SEQ ID NO: 1) or a salt thereof of this invention can be produced by fermentation of the compound [II] (SEQ ID NO: 1) or a salt thereof-producing strain belonging to the genus Coleophoma such as Coleophoma sp. F-11899 in a nutrient medium.

(i) Microorganism:

Particulars of the microorganism used for producing the compound [II] (SEQ ID NO: 1) or a salt thereof is explained in the following.

The strain F-11899 was originally isolated from a soil sample collected at Iwaki-shi, Fukushima-ken, Japan. This organism grew rather restrictedly on various culture media, and formed dark grey to brownish grey colonies. Anamorph (conidiomata) produced on a steam-sterilized leaf segment affixed on a Miura's LCA plate[1]) or a corn meal agar plate by inoculating the isolate, while neither teleomorph nor anamorph formed on the agar media. Its morphological, cultural and physiological characteristics are as follows.

1) Miura, K. and M. Y. Kudo: An agar-medium for aquatic Hyphomycetes., Trans. Ycolo. Soc. Japan, 11:116–118, 1970.

Cultural characteristics on various agar media are summarized in Table 1. Cultures on potato dextrose agar grew rather rapidly, attaining 3.5–4.0 cm in diameter after two weeks at 25° C. This colony surface was plane, felty, somewhat wrinkly and brownish grey. The colony center was pale grey to brownish grey, and covered with aerial hyphae. The reverse color was dark grey. Colonies on malt extract agar grew more restrictedly, attaining 2.5-3.0 cm in diameter under the same conditions. The surface was plane, thin to felty and olive brown. The colony center was yellowish grey, and covered with aerial hyphae. The reverse was brownish grey.

The morphological characteristics were determined on basis of the cultures on a sterilized leaf affixed to a Miura's LCA plate. Conidiomata formed on the leaf segment alone. They were pycnidial, superficial, separate, discoid to ampulliform, flattened at the base, unilocular, thin-walled, black, 90–160(−200) μm in diameter and 40–70 μm high. Ostiole was often single, circular, central, papillate, 10–30 μm in diameter and 10–20 μm high. Conidiophores formed from the lower layer of inner pycnidial walls. They were hyaline, simple or sparingly branched, septate and smooth. Conidiogenous cells were enteroblastic, phialidic, determinate, ampulliform to obpyriform, hyaline, smooth, 5–8×4–6 μm, with a collarette. The collarettes were campanulate to cylindrical, and 14–18×3–5 μm. Conidia were hyaline, cylindrical, thin-walled, aseptate, smooth and 14–16(−18)×3–3 μm.

The vegetative hyphae were septate, brown, smooth and branched. The hyphal cells were cylindrical and 2–7 μm thick. The chlamydospores were absent.

The strain F-11899 had a temperature range for growth of 0° to 31° C. and an optimum temperature of 23° to 27° C. on potato dextrose agar.

The above characteristics indicate that the strain F-11899 belongs to the order Coelomycetes[2], [3], [4]. Thus, we named the strain "Coelomycetes strain F-11899".

2) Arx, J. A. von: The Genera of Fungi—Sporulating in Pure Culture (3rd ed.), 315 p., J. Cramer, Vaduz, 1974.
3) Sutton, B. C.: The Coelomycetes—Fungi Imperfecti with Pycnidia, Acervuli and Stromata., 696 p., Commonwealth Mycological Institute, Kew, 1980.
4) Hawksworth, D. L., B. C. Sutton and G. C. Ainsworth: Dictionary of the Fungi (7th ed.), 445 p., Commonwealth Mycological Institute, Kew., 1983.

TABLE 1

| Cultural characteristics of the strain F-11899 | | |
|---|---|---|
| Medium | | Cultural characteristics |
| Malt extract agar (Blakeslee 1915) | G: | Rather restrictedly, 2.5-3.0 cm |
| | S: | Circular, plane, thin to felty, olive brown (4F5), arising aerial hyphae at the center (yellowish grey (4B2)) |
| | R: | Brownish grey (4F2) |
| Potato dextrose agar (Difco 0013) | G: | Rather rapidly, 3.5-4.0 cm |
| | S: | Circular, plane, felty, somewhat wrinkly, brownish grey (4F2), arising aerial hyphae at the center (pale grey (4B1) to brownish grey (4F2)) |
| | R: | Dark grey (4F1) |
| Czapeck's solution agar (Raper and Thom 1949) | G: | Very restrictedly, 1.0-1.5 cm |
| | S: | Irregular, thin, scanty, immersed, subhyaline to white. |
| | R: | Subhyaline to white |
| Sabouraud dextrose agar (Difco 0109) | G: | Restrictedly, 2.0-2.5 |
| | S: | Circular, plane, thin, white, sectoring, light brown (6D5) at the colony center |
| | R: | Pale yellow (4A3) |
| Oatmeal agar (Difco 0552) | G: | Fairly rapidly, 4.0-4.5 cm |
| | S: | Circular, plane, felty to cottony, dark grey (4F1) to brownish grey (4F2) |
| | R: | Brownish grey (4D2) |
| Emerson Yp Ss agar (Difco 0739) | G: | Restrictedly, 2.0-2.5 cm |
| | S: | Circular to irregular, plane, felty, dark grey (4F1) to brownish grey (4F2) |
| | R: | Medium grey (4E1) to dark grey (4F1) |
| Corn meal agar (Difco 0386) | G: | Rather restrictedly, 2.5-3.0 cm |
| | S: | Circular, plane, thin to felty, dark grey (2F1) to olive (2F3) |
| | R: | Dark grey (2P1) to olive (2F3) |
| MY20 agar | G: | Restrictedly, 1.5-2.0 cm |
| | S: | Circular to irregular, thin, sectoring, yellowish white (4A2) |
| | R: | Pale yellow (4A3) to orange white (5A2) |

Abbreviations:
G: growth, measuring colony size in diameter
S: colony surface
R: reverse These characteristics were observed after 14 days of incubation at 25° C. The color descriptions were based on the Methuen Handbook of Colour[5].

5) Kornerup, A. and Wanscher, J. H.: Methuen Handbook of Colour (3rd ed.), 252 p., Methuen, London, 1983.

A culture of Coelomycetes strain F-11899 thus named has been deposited with the Fermentation Research Institute Agency of Industrial Science and Technology (1–3, Higashi 1 chome, Tsukuba-shi, IBARARKI 305 JAPAN) on Oct. 26, 1989 under the number of FERM BP-2635.

After that, however, we have further studied the classification of the strain F-11899, and have found that the strain F-11899 resembled Coleophoma empetri (Rostrup) Petrak 1929 2), 3), 4) belonging to the order Coelomycetes, but differed in some pycnidial characteristics: globose or flattened at the base, immersed, and not papillate.

Considering these characteristics, we classified this strain in more detail and renamed it as "Coleophoma sp. F-11899".

In this connection, we have already taken step to amend the name, "Coelomycetes strain F-11899" to Coleophoma sp. F-11899 with the Fermentation Research Institute Agency of Industrial Science and Technology on Sep. 21, 1990.

(ii) Production of the compound [II] (SEQ ID NO: 1) or a salt thereof

The compound [II] (SEQ ID NO: 1) or a salt thereof of this invention is produced when the compound [II] (SEQ ID NO: 1) or a salt thereof-producing strain belonging to the genus Coleophoma is grown in a nutrient medium containing sources of assimilable carbon and nitrogen under aerobic conditions (e.g. shaking culture, submerged culture, etc.).

The preferred sources of carbon in the nutrient medium are carbohydrates such as glucose, sucrose, starch, fructose or glycerin, or the like.

The preferred sources of nitrogen are yeast extract, peptone, gluten meal, cotton seed flour, soybean meal, corn steep liquor, dried yeast, wheat germ, etc., as well as inorganic and organic nitrogen compounds such as ammonium salts (e.g. ammonium nitrate, ammonium sulfate, ammonium phosphate, etc.), urea or amino acid, or the like.

The carbon and nitrogen sources, though advantageously employed in combination need not to he used in their pure form because less pure materials, which contain traces of growth factors and considerable quantities of mineral nutrients, are also suitable for use.

When desired, there may be added to the medium mineral salts such as sodium or calcium carbonate, sodium or potassium phosphate, sodium or potassium chloride, sodium or potassium iodide, magnesium salts, copper salts, zinc salt, or cobalt salts, or the like.

If necessary, especially when the culture medium foams seriously a defoaming agent, such as liquid paraffin, fatty oil, plant oil, mineral oil or silicone, or the like may be added.

As in the case of the preferred methods used for the production of other biologically active substances in massive amounts, submerged aerobic cultural conditions are preferred for the production of the compound [II] (SEQ ID NO: 1) or a salt thereof in massive amounts.

For the production in small amounts, a shaking or surface culture in a flask or bottle is employed.

Further, when the growth is carried out in large tanks, it is preferable to use the vegetative form of the organism for inoculation in the production tanks in order to avoid growth lag in the process of production of the compound [II] (SEQ ID NO: 1) or a salt thereof. Accordingly, it is desirable first to produce a vegetative inoculum of the organism by inoculating a relatively small quantity of culture medium with spores or mycelia of the organism and culturing said inoculated medium, and then to transfer the cultured vegetative inoculum to large tanks. The medium, in which the vegetative inoculum is produced, is substantially the same as or different from the medium utilized for the production of the compound [II] (SEQ ID NO: 1) or a salt thereof.

Agitation and aeration of the culture mixture may be accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

The fermentation is usually conducted at a temperature between about 10° C. and 40° C., preferably 20° C. to 30° C., for a period of about 50 hours to 150 hours, which may be varied according to fermentation conditions and scales.

When the fermentation is completed, the culture broth is then subjected for recovery of the compound [II] (SEQ ID NO: 1) or a salt thereof to various procedures conventionally used for recovery and purification of biological active substances, for instance, solvent extraction with an appropriate solvent or a mixture of some solvents, chromatography or recrystallization from an appropriate solvent or a mixture of some solvents, or the like.

According to this invention, in general, the compound [II] (SEQ ID NO: 1) or a salt thereof is found both in the cultured mycelia and cultured broth. Accordingly, then the compound [II](SEQ ID NO: 1) or a salt thereof is removed from the whole broth by means of extraction using an appropriate organic solvent such as acetone or ethyl acetate, or a mixture of these solvents, or the like.

The extract is treated by a conventional manner to provide the compound [II]](SEQ ID NO: 1) or a salt thereof, for example, the extract is concentrated by evaporation or distillation to a smaller amount and the resulting residue containing active material, i.e. the compound [II] (SEQ ID NO: 1) or a salt thereof is purified by conventional purification procedures, for example, chromatography or recrystallization from an appropriate solvent or a mixture of some solvents.

When the object compound is isolated as a salt of the compound [II](SEQ ID NO: 1), it can be converted to the free compound [II] (SEQ ID NO: 1) or another salt of the compound [II] (SEQ ID NO: 1) according to a conventional manner.

BIOLOGICAL PROPERTIES OF THE POLYPEPTIDE COMPOUND [I] (SEQ ID NO: 1) OF THE PRESENT INVENTION

In order to show the usefulness of the polypeptide compound [I] (SEQ ID NO: 1) of the present invention, some biological data of the representative compounds are explained in the following.

Test 1 Antimicrobial Activity (1):

Antimicrobial activity of the compound of Example 2 disclosed later (hereinafter referred to as FR131535 substance) was measured by micro-broth dilution method in 96 well multi-trays employing yeast nitrogen base dextrose medium. To a 50 μl sample solution with serial 2-fold dilution was added a 50 μl of microorganism suspension in saline to yield a final concentration of $1 \times 10^5$ colony forming units/ml. The Candida cultures were incubated at 37° C. for 22 hours. After incubation, the growth of microorganism in each well was determined by measuring the turbidity. The results were shown as $IC_{50}$ value in which concentration the turbidity was half of that in the well without sample. The results are shown in Table 2.

TABLE 2

| organism | $IC_{50}$ |
|---|---|
| Candida albicans FP578 | 0.31 |
| Candida tropicalis YC118 | 0.47 |

Test 2 Acute Toxicity of FR131535 Substance:

The acute toxicity of the FR131535 substance was determined to ICR mice (female, 4 weeks old) by a single intravenous injection. No toxic symptom was observed at the dose of 500 mg/kg.

Test 3 Antimicrobial Activity (2):

In vitro antimicrobial activity of the compound of Example 12 disclosed later (hereinafter referred to as FR139687 substance) was determined by the two-fold agar-plate dilution method as described below.

One loopful of an overnight culture of each test microorganism in Sabouraud broth containing 2% Glucose ($10^5$ viable cells per ml) was streaked on yeast nitrogen base dextrose agar (YNBDA) containing graded concentrations of the FR139687 substance, and the minimal inhibitory concentration (MIC) was expressed in terms of μg/ml after incubation at 30° C. for 24 hours.

| organism | MIC (μg/ml) |
|---|---|
| Candida ablicans YU-1200 | 0.05 |

From the test results, it is realized that the polypeptide compound [I] (SEQ ID NO: 1) of the present invention has an anti-microbial activity (especially, antifungal activity).

The pharmaceutical composition of this invention can be used in the form of a pharmaceutical preparation, for example, in solid, semisolid or liquid form, which contains the polypeptide compound [I] (SEQ ID NO: 1) or a pharmaceutically acceptable salt thereof, as an active ingredient in admixture with an organic or inorganic carrier or excipient suitable for rectal, pulmonary (nasal or buccal inhalation), nasal, ocular, external (topical), oral or parenteral (including subcutaneous, intravenous and intramuscular) administrations or insufflation. The active ingredient may be compounded, for example, with the usual non-toxic, pharmaceutically acceptable carriers for tablets, pellets, troches, capsules, suppositories, creams, ointments, aerosols, powders for insufflation, solutions, emulsions, suspensions, and any other form suitable for use. And, if necessary, in addition, auxiliary, stabilizing, thickening and coloring agents and perfumes may be used. The polypeptide compound [I] (SEQ ID NO: 1) or a pharmaceutical acceptable salt thereof is/are included in the pharmaceutical composition in an amount sufficient to produce the desired antimicrobial effect upon the process or condition of diseases.

For applying the composition to human, it is preferable to apply it by intravenous, intramuscular, pulmonary, or oral administration, or insufflation. While the dosage of therapeutically effective amount of the polypeptide compound [I] (SEQ ID NO: 1) varies from and also depends upon the age and condition of each individual patient to be treated, in the case of intravenous administration, a daily dose of 0.01-20 mg of the polypeptide compound [I] (SEQ ID NO: 1) per kg weight of human being, in the case of intramuscular administration, a daily dose of 0.1-20 mg of the polypeptide compound [I] (SEQ ID NO: 1) per kg weight of human being, in case of oral administration, a daily dose of 0.5-50 mg of the polypeptide compound [I] (SEQ ID NO: 1) per kg weight of human being is generally given for treating or preventing infectious diseases.

The following Preparations and Examples are given for the purpose of illustrating the present invention in more detail.

Preparation 1

To methanol (50 ml) was added thionyl chloride (8.73 ml) at $-5°$ C. and the mixture was stirred for 10 minutes and then D-2-(p-hydroxyphenyl)glycine (5 g) was added thereto under ice-cooling. The mixture was stirred for 12 hours at room temperature. The reaction mixture was evaporated under reduced pressure to give D-2-(p-hydroxyphenyl)glycine methyl ester hydrochloride (6.3 g).

IR (Nujol): 3380, 1720, 1580, 1250 cm$^{-1}$

NMR (DMSO-d$_6$, δ): 3.70 (3H, s), 5.11 (1H, s), 6.83 (2H, d, J=8.6 Hz), 7.28 (2H, d, J=8.6 Hz), 8.91 (2H, s), 9.93 (1H, s)

Preparation 2

To a solution of D-2-(p-hydroxyphenyl)glycine methyl ester hydrochloride (6.3 g) and triethylamine (8.71 ml) in tetrahydrofuran (100 ml) was added di-t-butyl dicarbonate (6.82 g). The mixture was stirred for 2 hours at room temperature. The reaction mixture was added to diethyl ether (1 l) and an insoluble material was filtered off, and the filtrate was evaporated under reduced pressure to give N-(t-butoxycarbonyl)-D-2-(p-hydroxyphenyl)glycine methyl ester (6.83 g).

IR (Nujol): 3420, 3350, 1720, 1660 cm$^{-1}$

NMR (DMSO-d$_6$, δ): 1.38 (9H, s), 3.59 (3H, s), 5.05 (1H, d, J=7.9 Hz), 6.70 (2H, d, J=8.5 Hz), 7.16 (2H, d, J=8.5 Hz), 7.60 (1H, d, J=7.9 Hz), 9.48 (1H, s)

Preparation 3

To a suspension of N-(t-butoxycarbonyl)-D-2-(p-hydroxyphenyl)glycine methyl ester (6.8 g) and potassium bicarbonate (1.84 g) in N,N-dimethylformamide (34 ml) was added octyl bromide (4.176 ml). The mixture was stirred for 6 hours at 60° C. The reaction mixture was added to a mixture of water and ethyl acetate. The organic layer was separated and dried over magnesium sulfate. The magnesium sulfate was filtered off, and the filtrate was evaporated under reduced pressure to give N-(t-butoxycarbonyl)-D-2-(p-octyloxyphenyl)glycine methyl ester (6.96 g).

IR (Nujol): 1710, 1490, 1240, 1160 cm$^{-1}$

NMR (DMSO-d$_6$, δ): 0.859 (3H, t, J=6.2 Hz), 1.17-1.33 (10H, m), 1.38 (9H, s), 1.60-1.80 (2H, m), 3.59 (3H, s), 3.93 (2H, t, J=6.3 Hz), 5.11 (1H, d, J=7.9 Hz ), 6.87 (2H, d, J=8.7 Hz ), 7.27 (2H, d, J=8.7 Hz), 7.68 (1H, d, J=7.9 Hz)

Preparation 4

To 4N aqueous solution of sodium hydroxide (8.77 ml ) was added N-(t-butoxycarbonyl)-D-2-(p-octyloxyphenyl)glycine methyl ester (6.9 g) and stirred for 1.5 hours at room temperature. The reaction mixture was added to a mixture of water and ethyl acetate and 1N hydrochloric acid was added thereto to adjust the mixture to pH 3. The organic layer was separated and dried over magnesium sulfate. The magnesium sulfate was filtered off, and the filtrate was evaporated under reduced pressure to give N-(t-butoxycarbonyl)-D-2-(p-octyloxyphenyl)glycine (3.9 g).

NMR (DMSO-d$_6$, δ): 0.860 (3H, t, J=6.8 Hz), 1.17-1.33 (10H, m), 1.38 (9H, s), 1.60-1.80 (2H, m), 3.93 (2H, t, J=6.4 Hz), 5.10 (1H, d, J=8.2 Hz), 6.87 (2H, d, J=8.7 Hz), 7.28 (2H, d, J=8.7 Hz), 7.46 (1H, d, J=8.2 Hz)

Preparation 5

To a solution of N-(t-butoxycarbonyl)-D-2-(p-octyloxyphenyl)glycine (1 g) in acetonitrile (10 ml) and pyridine (0.213 ml) in acetonitrile (10 ml) was added N,N'-disuccinimidyl carbonate (0.675 g). The mixture was stirred for 12 hours at room temperature. The reaction mixture was added to a mixture of water and ethyl acetate. The organic layer was separated and dried over magnesium sulfate. The magnesium sulfate was filtered off, and the filtrate was evaporated under reduced pressure to give N-(t-butoxycarbonyl)-D-2-(p-octyloxyphenyl)glycine succinimido ester (0.92 g).

IR (Nujol): 3350, 1810, 1730, 1680 cm$^{-1}$

NMR (DMSO-d$_6$, δ): 0.862 (3H, t, J=6.7 Hz), 1.17-1.33 (10H, m), 1.40 (9H, s), 1.60-1.80 (2H, m), 2.77 (4H, s), 3.97 (2H, t, J=6.5 Hz), 5.54 (1H, d, J=8.1 Hz), 6.91 (2H, d, J=8.7 Hz), 7.39 (2H, d, J=8.7 Hz), 8.05 (1H, d, J=8.1 Hz)

Preparation 6

N-(t-Butoxycarbonyl)-L-tyrosine methyl ester was obtained according to a similar manner to that of Preparation 2.

IR (Nujol): 3430, 3360, 1730, 1670, 1170 cm$^{-1}$

NMR (DMSO-d$_6$, δ): 1.33 (9H, s), 2.90 (2H, m), 3.59 (3H, s), 4.05 (1H, m), 6.65 (2H, d, J=8.4 Hz), 7.00 (2H, d, J=8.4 Hz), 7.21 (1H, d, J=8.0 Hz), 9.22 (1H, s)

Preparation 7

$O^4$-Octyl-N-(t-butoxycarbonyl)-L-tyrosine methyl ester was obtained according to a similar manner to that of Preparation 3.

IR (Nujol): 3350, 1735, 1685, 1250, 1170 cm$^{-1}$

NMR (DMSO-d$_6$, δ): 0.859 (3H, t, J=6.7 Hz), 1.20–1.30 (10H, m), 1.68 (2H, quintet, J=7.3 Hz), 2.82 (2H, m), 3.60 (3H, s), 3.91 (2H, t, J=7.3 Hz), 4.08 (1H, m), 6.81 (2H, d, J=8.6 Hz), 7.12 (2H, d, J=8.6 Hz), 7.25 (1H, d, J=8.0 Hz)

Preparation 8

$O^4$-Octyl-N-(t-butoxycarbonyl)-L-tyrosine was obtained according to a similar manner to that of Preparation 4.

IR (Nujol): 3400–2900 (br), 1700, 1240, 1160 cm$^{-1}$

NMR (DMSO-d$_6$, δ): 0.859 (3H, t, J=6.8 Hz), 1.20–1.30 (10H, m), 1.32 (9H, s), 1.68 (2H, quintet, J=7.0 Hz), 2.67–2.95 (1H, m), 3.90 (2H, t, J=7.0 Hz), 4.01 (1H, m), 6.81 (2H, d, J=8.6 Hz), 7.02 (1H, d, J=8.3 Hz), 7.13 (2H, d, J=8.6 Hz)

Preparation 9

$O^4$-Octyl-N-(t-butoxycarbonyl)-L-tyrosine succinimido ester was obtained according to a similar manner to that of Preparation 5.

IR (Nujol): 3350, 1780, 1720, 1690 cm$^{-1}$

NMR (DMSO-d$_6$, δ): 0.860 (3H, t, J=6.7 Hz), 1.20–1.30 (10H, m), 1.32 (9H, s), 1.68 (2H, quintet, J=7.0 Hz), 2.82 (4H, s), 2.80–3.20 (1H, m), 3.92 (2H, t, J=7.0 Hz), 4.44 (1H, m), 6.81 (2H, d, J=8.5 Hz), 7.22 (2H, d, J=8.5 Hz), 7.60 (1H, d, J=8.3 Hz)

Preparation 10

(1) A seed medium (160 ml) consisting of sucrose 4%, cotton seed flour 2%, dried yeast 1%, peptone 1%, KH$_2$PO$_4$ 0.2%, CaCO$_3$ 0.2% and Tween 80 (made by NAKARAI CHEMICALS LTD.) 0.1% was poured into each of two 500 ml Erlenmeyer flasks and sterilized at 121° C. for 30 minutes. A loopful of slant culture of Coleophoma sp. F-11899 was inoculated to each of the medium and cultured under shaking condition at 25° C. for 4 days.

A production medium (20 liters) consisting of Pine Dex #3 (made by Matsutani Chemical Ltd. ) 3%, glucose 1%, wheat germ 1%, cotton seed flour 0.5%, KH$_2$PO$_4$ 2%, Na$_2$HPO$_4$.12H$_2$O 1.5%, ZnSO$_4$.7H$_2$O 0.001% and Adekanol (defoaming agent, made by Asahi Denka Co., Ltd.) 0.05% was poured into a 30 liter-jar fermentor and sterilized at 121° C. for 30 minutes.

The resultant seed culture broth (320 ml) was inoculated to the production medium and cultured at 25° C. for 4 days, agitated at 200 rpm and aerated at 20 liters per minute. To the cultured broth thus obtained (20 liters) was added an equal volume of acetone. After occasionally stirring at room temperature for a while, the broth was filtered. The filtrate was concentrated in vacuo to remove acetone. The aqueous filtrate (10 liters) was washed with two equal volume of ethyl acetate and extracted with n-butanol (10 liters) twice. The combined n-butanol layer was concentrated in vacuo and the residue was applied on a column (300 ml) of Silica gel 60 (made by E. Merck) and eluted with a stepwise organic solvent mixture consisting of dichloromethane-methanol. The fractions having anti-Candida activity were eluted in the range of the solvent mixture (3:1 through 1:1). The active fractions were combined and concentrated in vacuo to dryness. The residue was dissolved in 50% aqueous methanol (15 ml) and applied on a column (250 ml) of ODS YMC GEL (made by Yamamura Chemical Lab.). The column was washed with 50% aqueous methanol and eluted with 80% aqueous methanol. The eluate was concentrated and was further purified on a centrifugal partition chromatography (CPC) using a solvent system n-butanol:-methanol:water (4:1:5) of upper stationary phase and lower mobile phase in a descending mode. The pooled fractions containing the object compound (major component) were concentrated in vacuo and applied on a column (35 ml) of silica gel 60. The column was developed with n-butanol:acetic acid:water (6:1:1). The active fractions were combined and concentrated in vacuo to dryness and dissolved in a small volume of 50% aqueous methanol. The solution was passed through a column (3.5 ml) of ODS YMC GEL. The column was washed with 50% aqueous methanol and eluted with methanol. The eluate was concentrated to dryness, dissolved in a small volume of water and adjusted to pH 7.0 with 0.01N NaOH. The solution was freeze-dried to give a white powder of said compound in its sodium salt form (hereinafter referred to as FR901379 substance (SEQ ID NO: 1)) (11 mg).

The FR901379 substance (SEQ ID NO: 1) as obtained has the following physico-chemical properties.

Appearance:
  white powder
Nature:
  neutral substance
Melting point:
  215°–221° C. (dec.)
Specific rotation:
  $[\alpha]_D^{23}$ −20.3 (C: 0.5, H$_2$O)
Molecular formula:
  $C_{51}H_{81}N_8O_{21}SNa$
Elemental Analysis:
  Calcd.: for $C_{51}H_{81}N_8SO_{21}Na$ C 51.17, H 6.77, N 9.36, S 2.68 (%) Found: C 49.61, H 7.58, N 7.65, S 2.14 (%)
Molecular weight:
  HRFAB-MS: 1219.5078 (Calcd for $C_{51}H_{82}N_8SO_{21}+2Na-H$: 1219.5032)
Solubility:
  soluble: methanol, water
  slightly soluble: ethyl acetate, acetone
  insoluble: chloroform, n-hexane
Color reaction:
  positive: iodine vapor reaction, cerium sulfate reaction, ferric chloride reaction, Ninhydrin reaction
  negative: Dragendorff reaction, Ehrlich reaction

| Thin layer chromatography (TLC): | | |
|---|---|---|
| Stationary phase | Developing solvent | Rf value |
| silica gel* | n-butanol:acetic acid; water (3:1:1) | 0.36 |
|  | ethyl acetate:isopropyl alcohol:water (5:3:1) | 0.31 |

*Silica Gel 60 (made by E. Merck)

Ultraviolet absorption spectrum:
  $\lambda_{max}^{methanol}$ (E$_1$ $_{cm}^{1\%}$): 207(169), 276(13.5), 225(sh),283(sh) nm
  $\lambda_{max}^{methanol+0.01N\text{-}NaOH}$ (E$_1$ $_{cm}^{1\%}$): 209(232), 244(59.5), 284(13.5), 294(sh) nm
Infrared absorption spectrum:

$\lambda_{max}^{KBr}$: 3350, 2920, 2840, 1660, 1625, 1530, 1510, 1435, 1270, 1240, 1070, 1045, 800, 755, 710 cm$^{-1}$ 1H Nuclear magnetic resonance spectrum:
(CD$_3$OD, 400 MHz)

δ: 7.30 (1H, d, J=2 Hz), 7.03 (1H, dd, J=8 and 2 Hz), 6.85 (1H, d, J=8 Hz), 5.23 (1H, d, J=3 Hz), 5.06 (1H, d, J=4 Hz), 4.93 (1H, d, J=3 Hz), 4.59-4.51 (3H, m), 4.47-4.35 (5H, m), 4.29 (1H, dd, J=6 and 2 Hz), 4.17 (1H, m), 4.07 (1H, m), 3.95-3.89 (2H, m), 3.76 (1H, broad d, J=11 Hz), 3.36 (1H, m), 2.75 (1H, dd, J=16 and 4 Hz), 2.50 (1H, m), 2.47 (1H, dd, J=16 and 9 Hz), 2.38 (1H, m), 2.21 (2H, m), 2.03-1.93 (3H, m), 1.57 (2H, m), 1.45-1.20 (24H, m), 1.19 (3H, d, J=6 Hz), 1.08 (3H, d, J=6 Hz), 0.90 (3H, t, J=7 Hz)

From the analysis of the above physical and chemical properties, and the result of the further investigation of identification of chemical structure, the chemical structure of the FR901379 substance (SEQ ID NO: 1) has been identified and assigned as follows.

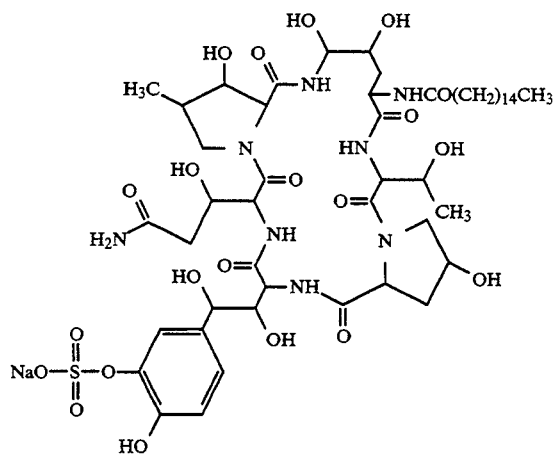

EXAMPLE 1

N-acyl group of FR901379 substance (SEQ ID NO: 1) was eliminated by the reaction with an enzyme. In the following, this elimination process is explained in detail.

(1) Fermentation of Actinoplanes utahensis

The enzyme which is useful for eliminating N-acyl group of FR901379 substance (SEQ ID NO: 1) is produced by certain microorganisms of the Actinoplanaceae, preferably the microorganism Actinoplanes utahensis IFO-13244.

A stock culture of Actinoplanes utahensis IFO-13244 is prepared and maintained on agar slant. A loopful of the slant culture was inoculated into a seed medium consisted of starch 1%, sucrose 1%, glucose 1%, cotton seed flour 1%, peptone 0.5%, soy bean meal 0.5% and CaCO$_3$ 0.1%. The inoculated vegetative medium was incubated in a 225-ml wide mouth Erlenmeyer flask at 30° C. for about 72 hours on a rotary shaker.

This incubated vegetative medium was used directly to inoculate into a production medium consisted of sucrose 2%, peanut powder 1%, K$_2$HPO$_4$ 0.12% KH$_2$PO$_4$ 0.05% and MgSO$_4$·7H$_2$O 0.025%. The inoculated production medium was allowed to ferment in a 30-liter jar fermentor at a temperature of 30° C. for about 80 hours. The fermentation medium was stirred with conventional agitators at 250 rpm and aerated at 20 liters per minute. The vegetative mycelium was collected from the fermented broth by filtration and once washed with water. The washed mycelium was directly used to eliminate N-acyl group of FR901379 substance (SEQ ID NO: 1) as an enzyme source.

(2) Elimination Condition

FR901379 substance was dissolved in 0.25M phosphate buffer (pH 6.5) at a concentration of 0.9 mg/ml. To a 36-liter of the solution was added a 2 kg wet weight of washed mycelium of Actinoplanes utahensis IFO-13244. The elimination reaction was carried out at 37° C. under for 23 hours. Reduction of FR901379 substance (SEQ ID NO: 1) and increase of the deacylated FR901379 substance (SEQ ID NO: 1) (hereinafter referred to as FR133303 substance) were measured using a HPLC equipped with a reverse phase column. From a 30 g of FR901379 substance (SEQ ID NO: 1), a 22.2 g of FR133303 substance was formed in the reaction mixture.

(3) Isolation of FR133303 Substance (SEQ ID NO: 1)

The reaction mixture described above was filtered with a filter aid. The mycelial cake was discarded. The filtrate thus obtained was passed through a column of activated carbon (2 L). The column was washed with 6 L of water and eluted with 12 L of 50% aqueous acetone. The eluate was evaporated in vacuo to remove acetone and then passed through a column (4 L) of YMC GEL ODS-AM 120-S50 (Yamamura Chemical Labs). The column was washed with water and eluted with 2% aqueous acetonitrile containing 50 mM NaH$_2$PO$_4$. Elution was monitored by analytical HPLC, using a column of LiChrospher 100 RP-18 (Cica-MERCK) and a solvent system of 3% aqueous acetonitrile containing 0.5% NH$_4$H$_2$PO$_4$ at a flow rate of 1 ml/min, detecting the FR133303 substance with a UV monitor at 210 nm. The fractions containing the FR133303 substance were combined and passed through a column of activated carbon (400 ml). The column was washed with water and eluted with 50% aqueous acetone. The eluate was concentrated in vacuo to remove acetone and lyophilized to give 16.4 g of FR133303 substance (SEQ ID NO: 1) as a white powder.

FR133303 substance (SEQ ID NO: 1) has following physico-chemical properties:

Appearance:
  white powder
Melting point:
  150°-160° C.(dec.)
Specific rotation:
  $[\alpha]_D^{24}$ −31.17° (C: 1.0, H$_2$O)
Molecular formula:
  C$_{35}$H$_{51}$N$_8$SO$_{20}$Na
Elemental Analysis:
  Calcd: for C$_{35}$H$_{51}$N$_8$SO$_{20}$Na C 43.84, H 5.36, N 11.69, S 3.34 (%) Found: C 41.14, H 5.74, N 10.88, S 3.10 (%)
Solubility:
  soluble: water
  slightly soluble: methanol
  insoluble: n-hexane
Color reaction:
  positive: iodine vapor reaction, cerium sulfate reaction, Ninhydrin reaction
  negative: Molish reaction

| Thin layer chromatography (TLC): | | |
|---|---|---|
| Stationary phase | Developing solvent | Rf value |
| silica gel* | n-butanol:acetic acid | 0.15 |

| Thin layer chromatography (TLC): | | |
|---|---|---|
| Stationary phase | Developing solvent | Rf value |
| | water (3:1:2) | |

Silica Gel 60 (made by E. Merck)

Ultraviolet absorption spectrum:
$\lambda_{max}^{H2O}$ (E$_{1\,cm}^{1\%}$): 201(340), 273(18), 224(sh), 281(sh) nm
$\lambda_{max}^{H2O+0.01N\text{-}NaOH}$ (E$_{1\,cm}^{1\%}$): 207(414), 243(122), 292(34)

Infrared absorption spectrum:
$v_{max}^{KBr}$: 3350, 2920, 1660, 1625, 1515, 1440, 1270, 1080, 1045, 800, 755, 715 cm$^{-1}$ $^1$H Nuclear magnetic resonance spectrum:
(D$_2$O, 400 MHz)
δ: 7.31 (1H, d, J=2 Hz), 7.12 (1H, dd, J=2 Hz and 8 Hz), 7.06 (1H, d, J=8 Hz), 5.40 (1H, d, J=3 Hz), 5.04 (1H, d, J=3.5 Hz), 4.94 (1H, d, J=6 Hz), 4.73–4.55 (3H, m), 4.51–4.38 (4H, m), 4.31–4.23 (3H, m), 4.11–4.06 (2H, m), 3.94–3.89 (2H, m), 3.41 (1H, m), 2.60–2.34 (5H, m), 2.14 (1H, m), 2.03 (1H, m), 1.28 (3H, d, J=6 Hz), 1.01 (3H, d, J=6.5 Hz)

$^{13}$C Nuclear magnetic resonance spectrum:
(D$_2$O, 100 MHz)
δ: 178.3 (s), 175.9 (s), 174.3 (s), 174.2 (s), 174.0 (s), 171.8 (s), 171.3 (s), 150.9 (s), 141.5 (s), 134.4 (s), 128.2 (d), 124.5 (d), 120.3 (d), 78.1 (d), 77.0 (d), 76.9 (d], 76.6 (d), 72.9 [d), 72.8 (d), 71.2 (d), 69.3 (d), 69.2 (d), 63.7 (d), 60.1 (d), 58.3 (t), 58.0 (d), 56.9 (d), 55.3 (d), 54.7 (t), 41.8 (t), 39.7 (d), 39.5 (t), 33.5 (t), 21.4 (g), 13.3 (g)

The chemical structure of FR133303 substance (SEQ ID NO: 1) has been identified and assigned as follows.

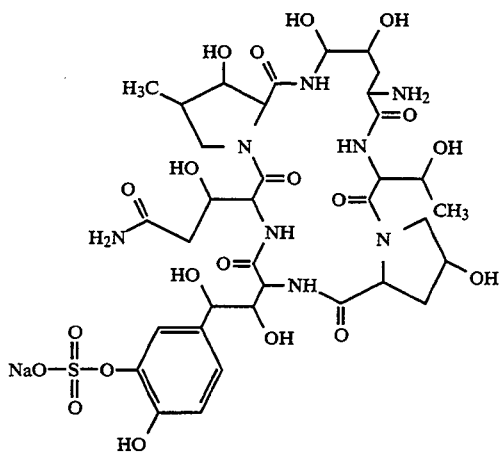

EXAMPLE 2

(1) A solution of 4-hydroxybenzoic acid (19.2 g) in 10% NaOH (120 ml) was dropwise added to 480 ml of dimethyl sulfoxide over 30 minutes during which the temperature in reaction mixture was controlled between 30° and 40° C. After adding, the solution was cooled to 17°–20° C. 1-Bromooctane (28.95 g) was dropwise added to the solution over 30 minutes and the reaction mixture was vigorously stirred for 4 hours at room temperature. The reaction mixture was poured into ice water (1200 ml) and acidified with 40 ml of conc. hydrochloric acid. After vigorously stirring for another 1 hour, the resulting solid was removed by filtration and dissolved in 60 ml of acetonitrile. The solution was refluxed over 30 minutes and was allowed to stand overnight at room temperature to yield 4-octyloxybenzoic acid (13.8 g) as a crystal (MP 96° C., Anal Calcd. for C$_{15}$H$_{22}$O$_3$: C 71.97, H 8.86, Found: C 71.30, H 8.89).

To a solution of 4-octyloxybenzoic acid (13.8 g) in diethyl ether (552 ml) were added 2,4,5-trichlorophenol (10.87 g) and N,N'-dicyclohexylcarbodiimide (11.37 g). The solution was stirred under a nitrogen atmosphere for 18 hours at room temperature. The precipitate was removed by filtration and the filtrate was concentrated in vacuo. The residue was dissolved in petroleum ether and was allowed to stand on ice-water. The resulting crystals (15.2 g) were filtered and dissolved in warm n-hexane (150 ml). After standing overnight at room temperature, the resulting crystal was removed by filtration. The filtrate was concentrated to an oil which was purified by a column chromatography over silica gel using a mixture of ethyl acetate and n-hexane to give 2,4,5-trichlorophenyl 4-octyloxybenzoate (7.58 g) (MP 53° C., Anal Calcd. for C$_{21}$H$_{23}$O$_3$Cl$_3$: Cl 24.75, Found: Cl 24.05).

(2) To a solution of FR133303 substance (SEQ ID NO: 1) (2.04 g) in N,N-dimethylformamide (60 ml) were added 2,4,5-trichlorophenyl 4-octyloxybenzoate (2.04 g) and 4-dimethylaminopyridine (0.283 g). The solution was stirred under a nitrogen atmosphere at room temperature for 15 hours. 4-Dimethylaminopyridine (0.20 g) was added to the solution and mixture was stirred for another 24 hours. The reaction mixture was poured into water (600 ml) and the pH was adjusted to 6.0. The mixture was washed twice with an equal volume of ethyl acetate and concentrated to 30 ml. The concentrate was applied on a column (150 ml) of DEAE-Toyopearl (Cl type, manufactured by Tosoh). The column was washed with 50% aqueous methanol and developed with 50% aqueous methanol containing 1M sodium chloride aqueous solution. The elution of product was assessed by the same HPLC system as described in Example 1(3) except that the concentration of acetonitrile in solvent was 40%. The fractions containing the object compound were pooled and evaporated in vacuo to remove methanol. The solution was absorbed on a column (1 L) of YMC GEL ODS-AM 120-S50 in order to remove salt. The column was washed with water and eluted with 30% aqueous acetonitrile. The eluate was evaporated in vacuo to remove acetonitrile and lyophylized to give the object compound (hereinafter referred to as FR131535 substance (SEQ ID NO: 1)) (1.4 g) as a white powder.

FR131535 substance has following physico-chemical properties:

Appearance:
 white powder
Melting point:
 170°–189° C. (dec.)
Specific rotation:
 [α]$_D^{20}$ −14.4° (C: 10, H$_2$O)
Molecular formula:
 C$_{50}$H$_{71}$N$_8$SO$_{22}$Na
Elemental Analysis:
 Calcd: for C$_{50}$H$_{71}$N$_8$SO$_{22}$Na.6H$_2$O C 46.22, H 6.44, N 8.62, S 2.46, Na 1.77 (%) Found: C 46.80, H 6.13, N 8.78, S 1.96, Na 1.81 (%)
Solubility:
 soluble: methanol, water
 slightly soluble: acetone insoluble: n-hexane
Color reaction:
  positive: iodine vapor reaction, cerium sulfate reaction

| Thin layer chromatography (TLC): | | |
|---|---|---|
| Stationary phase | Developing solvent | Rf value |
| silica gel* | n-butanol:acetic acid:water (6:1:1) | 0.21 |

*Silica Gel 60 (made by E. Merck)

Infrared absorption spectrum:
  $\nu_{max}^{KBr}$: 3330, 2900, 2850, 1620, 1500, 1430, 1270, 1250, 1170, 1110, 1080, 1040, 960, 940, 880, 840, 800, 750, 710 cm$^{-1}$ $^1$H Nuclear magnetic resonance spectrum:
  (CD$_3$OD, 200 MHz)
  δ: 7.78 (2H, d, J=8 Hz), 7.31 (1H, d, J=2 Hz), 7.03 (1H, dd, J=8 Hz and 8 Hz), 6.96 (2H, d, J=8 Hz), 6.87 (1H, d, J=8 Hz), 5.33 (1H, d, J=3 Hz), 5.08 (1H, d, J=4 Hz), 4.99 (1H, d, J=3 Hz), 4.80-3.20 (17H, m), 2.83 (1H, m), 2.65-2.30 (4H, m), 2.22-1.90 (2H, m), 1.79 (2H, m), 1.56-1.25 (10H, m), 1.19 (3H, d, J=6 Hz), 1.06 (3H, d, J=6.5 Hz), 0.90 (3H, t, J=6.5 Hz)

The chemical structure of FR131535 substance (SEQ ID NO: 1) has been identified and assigned as follows.

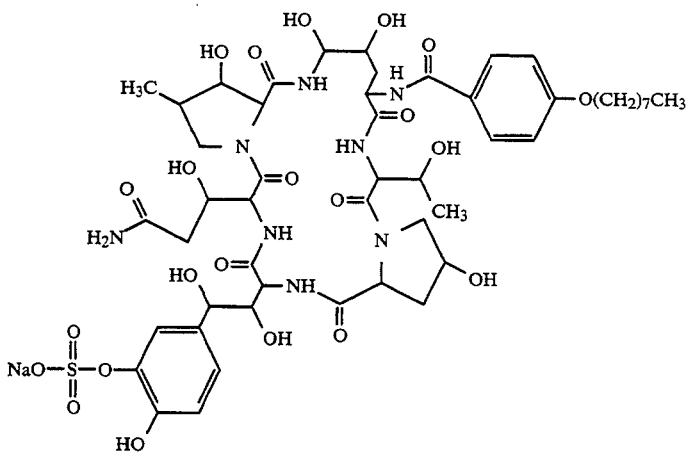

In the following, the structures of the compounds Examples 3 to 11 are shown (SEQ ID NO: 1).

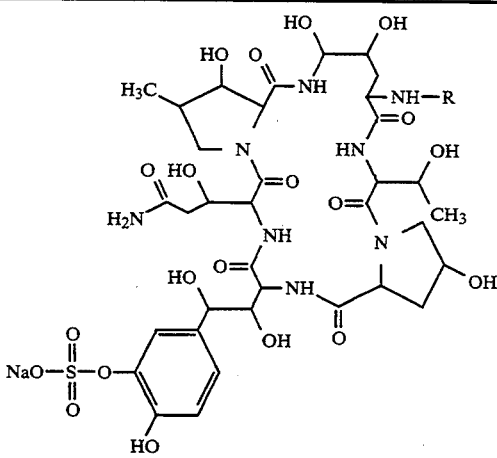

| Example No. | Compound No. | R |
|---|---|---|
| 3 | FR138260 | —COCH(D)(NHCOO$^t$Bu)—C$_6$H$_4$—O(CH$_2$)$_7$CH$_3$ |
| 4 | FR138727 | —COCH(D)(NH$_2$)—C$_6$H$_4$—O(CH$_2$)$_7$CH$_3$ |

-continued

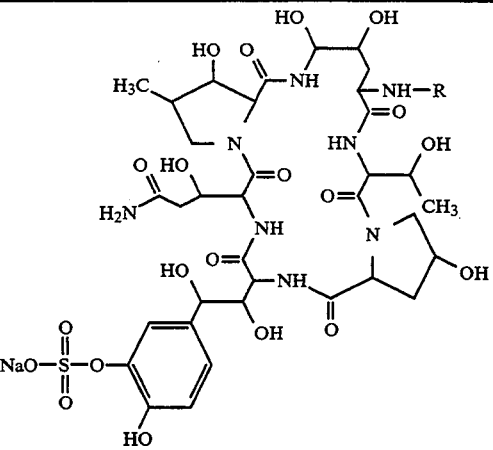

| Example No. | Compound No. | R |
|---|---|---|
| 5 | FR138364 | —COCHCH₂—C₆H₄—O(CH₂)₇CH₃ (L), with NHCOO^tBu |
| 6 | FR138261 | —COO^tBu |
| 7 | FR138363 | —COCH₃ |
| 8 | FR138728 | —COCH₂Br |
| 9 | FR138538 | —COO—C₆H₅ |
| 10 | FR138539 | —COC(=NOCH₃)—(thiazol-2-yl with NH₂) |
| 11 | FR138365 | —O₂S—C₆H₄—CH₃ |

EXAMPLE 3

To a solution of FR133303 substance (SEQ ID NO: 1) (1 g) and N-(t-butoxycarbonyl)-D-2-(p-octyloxyphenyl)glycine succinimido ester (0.596 g) in N,N-dimethylformamide (3 ml) was added 4-dimethylaminopyridine (0.165 g). The mixture was stirred for 12 hours at room temperature. The reaction mixture was added to water (30 ml) and then adjusted to pH 6. The aqueous solution was washed with ethyl acetate, and subjected to ion exchange chromatography on DEAE-Toyopearl (Cl ⊖) (60 ml) and eluted with 50% methanol in 1M aqueous solution of sodium chloride. The fractions containing the object compound were combined and evaporated under reduced pressure to remove methanol. The aqueous solution was adjusted to pH 4.5 with 1N hydrochloric acid and subjected to column chromatography on Diaion HP-20 (Trademark, Manufactured by Mitsubishi Chemical Industries) (130 ml) and eluted with 80% aqueous methanol. The fractions containing the object compound were combined and evaporated under reduced pressure to remove methanol. The residue was lyophilized to give object acylated compound (hereinafter referred to as FR138260 substance (SEQ ID NO: 1)) (0.77 g).

IR (Nujol): 3300, 1660, 1500, 1240, 1045, 800, 720 cm⁻¹

NMR (CD₃OD, δ): 0.92 (3H, t, J=6.8 Hz), 1.05 (3H, d, J=6.8 Hz), 1.17–1.33 (13H, m), 1.43 (9H, s), 1.6–1.8 (2H, m), 1.9–2.1 (3H, m), 2.50 (3H, m), 2.75 (1H, dd, J=16 Hz and 4 Hz), 3.35 (1H, m), 3.7–3.8 (1H, m), 3.93 (2H, t, J=6.2 Hz), 3.9–4.2 (5H, m), 4.3–4.5 (5H, m), 4.5–4.7 (3H, m), 4.97 (1H, d, J=3 Hz), 5.05 (1H, d, J=4 Hz), 5.11 (1H, s), 5.30 (1H, d, J=3 Hz), 6.85 (1H, d, J=8.3 Hz), 6.86 (2H, d, J=8.6 Hz), 7.02 (1H, d, J=8.3 Hz), 7.26 (2H, d, J=8.6 Hz), 7.31 (1H, s)

FAB-MS: e/z=1343 (M+Na)

EXAMPLE 4

FR138260 substance (SEQ ID NO: 1) obtained in Example 3 (0.25 g) was added to trifluoroacetic acid (1.25 ml) and stirred for 10 minutes. The reaction mixture was added to water (30 ml) and then adjusted to pH 4.5 with saturated aqueous solution of sodium bicarbonate. The aqueous solution was subjected to column chromatography on Diaion HP-20 (100 ml) and eluted with 80% aqueous methanol. The fractions containing the object compound were combined and evaporated under reduced pressure to remove methanol. The residue was lyophilized to give the object compound (hereinafter referred to as FR138727 substance) (SEQ ID NO: 1) (15 mg).

NMR (CD$_3$OD, δ): 0.90 (3H, t, J=6.8 Hz), 1.05 (3H, d, J=6.8 Hz), 1.17–1.33 (13H, m), 1.6–1.8 (2H, m), 1.9–2.1 (3H, m), 2.50 (1H, m), 2.75 (1H, dd, J=16 Hz and 4 Hz), 3.40 (1/4, m), 3.7–3.8 (1H, m), 3.98 (2H, t, J=6.2 Hz), 3.9–4.2 (5H, m), 4.3–4.5 (5H, m), 4.5–4.7 (3H, m), 4.97 (1H, d, J=3 Hz), 5.06 (1H, s), 5.20 (1H, d, J=3 Hz), 5.40 (1H, d, J=3 Hz), 6.85 (1H, d, J=8.3 Hz), 6.95 (2H, d, J=8.5 Hz), 7.02 (1H, d, J=8.3 Hz), 7.30 (1H, d, J=8.5 Hz ), 7.44 (1H, s)

FAB-MS: e/z=12.59 (M+K)

EXAMPLE 5

FR138364 substance (SEQ ID NO: 1) was obtained by reacting FR133303 substance (SEQ ID NO: 1) with O$^4$-octyl-N-(t-butoxycarbonyl)-L-tyrosine succinimido ester according to a similar manner to that of Example 3.

IR (Nujol): 3300, 1660, 1620, 1240, 1050 cm$^{-1}$

NMR (CD$_3$OD, δ): 0.904 (3H, t, J=6.8 Hz), 1.06 (3H, d, J=6.8 Hz), 1.17 (3H, d, J=6.7 Hz), 1.20–1.30 (10H, m ), 1.35 (9H, s ), 1.74 (2B, quintet, J=6.5 Hz), 1.9–2.1 (3H, m), 2.45 (3H, m), 2.76 (1H, dd, J=16 Hz and 4 Hz), 3.0–3.1 (2B, m), 3.37 (1H, m), 3.77 (1H, d, J=11 Hz), 3.92 (2H, t, J=6.8 Hz), 3.9–4.2 (7B, m), 4.3–4.5 (5H, m), 4.5–4.6 (3H, m), 4.94 (1H, d, J=3 Hz), 5.05 (1H, d, J=3.8 Hz), 5.31 (1H, d, J=3 Hz), 6.79 (2H, d, J=8.5 Hz), 6.85 (1H, d, J=S.3Hz), 7.03 (1H, dd, J=8.3 Hz and 2 Hz), 7.12 (2H, d, J=8.5 Hz), 7.31 (1H, d, J=2 Hz)

FAB-MS: e/z=1357 (M+Na)

EXAMPLE 6

A solution of FR133303 substance (SEQ ID NO: 1) (0.5 g) in a mixture of water (5 ml) and tetrahydrofuran (5 ml) was adjusted to pH 7 with saturated aqueous solution of sodium bicarbonate and N,N-di-t-butylcarbonate (0.114 g) was added thereto at room temperature. The mixture was stirred for 5 hours at room temperature maintaining pH 7 with saturated aqueous solution of sodium bicarbonate. The reaction mixture was added to water and adjusted to pH6. The aqueous solution was washed with ethyl acetate, and subjected to ion exchange chromatography on DEAE-Toyopearl (Cl$^-$) (30 ml) and eluted with 50% methanol in 1M aqueous solution of sodium chloride. The fractions containing the object compound were combined and evaporated under reduced pressure to remove methanol. The aqueous solution was adjusted to pH 4.5 with 1N hydrochloric acid and subjected to column chromatography on Diaion HP-20 (100 ml) and eluted with 80% aqueous methanol. The fractions containing the object compound were combined and evaporated under reduced pressure to remove methanol. The residue was lyophilized to give the object acylated compound (hereinafter referred to as FR138261 substance) (SEQ ID NO: 1) (0.145 g).

IR (Nujol): 3300, 1660, 1620, 1240, 1050 cm$^{-1}$

NMR (CD$_3$OD, δ): 1.06 (3H, d, J=6.8 Hz), 1.18 (3H, d, J=6.0 Hz), 1.40 (9H, s), 1.9–2.1 (3H, m), 2.44 (3H, m), 2.82 (1/{, dd, J=16 Hz and 4 Hz), 3.37 (1H, m), 3.75 (1H, d, J=11Hz), 3.89–4 (2H, m), 4.10 (1H, m), 4.15 (1H, m), 4.29 (1H, dd, J=6 Hz and 2 Hz), 4.36–4.45 (5H, m), 4.5–4.6 (3H, m), 4.97 (1H, d, J=3 Hz), 5.06 (1H, dd, J=8.2 Hz and 4 Hz), 5.33 (1H, d, J=3 Hz), 6.85 (1H, d, J=8.3 Hz), 7.03 (1H, dd, J=8.3 Hz and 2 Hz), 7.30 (1H, d, J=2 Hz), 7.50 (1H, d, J=8.2 Hz)

FAB-MS: e/z=1081 (M+Na)

EXAMPLE 7

FR138363 substance (SEQ ID NO: 1) was obtained by reacting FR133303 substance (SEQ ID NO: 1) with acetyl chloride according to a similar manner to that of Example 6.

IR (Nujol): 3300, 1620, 1250, 1040 cm$^{-1}$

NMR (CD$_3$OD, δ): 1.06 (3H, d, J=6.8 Hz), 1.20 (3H, d, J=6 Hz), 1.78–2.05 (3H, m), 1.96 (3H, s), 2.21–2.54 (3H, m), 2.95 (1H, m), 3.35–3.42 (1H, m), 3.58–4.42 (11H, m), 4.50–5.05 (5H, m), 5.23 (1H, m), 6.88 (1H, d, J=8.3 Hz), 7.05 (1H, dd, J=8.3 Hz and 2 Hz), 7.35 (1H, d, J=2 Hz)

FAB-MS: 1023 (M+Na)

EXAMPLE 8

FR138728 substance (SEQ ID NO: 1) was obtained by reacting FR133303 substance (SEQ ID NO: 1) with 2-bromoacetyl chloride according to a similar manner to that of Example 6.

IR (Nujol): 3300, 1660, 1620, 1500, 1220, 1040 cm$^{-1}$

NMR (CD$_3$OD, δ): 1.06 (3H, d, J=6.9 Hz), 1.17 (3H, d, J=6.1 Hz), 1.9–2.1 (3H, m), 2.50 (3H, m), 2.80 (1H, dd, J=16 Hz and 4 Hz), 3.37 (1H, m), 3.6–4.0 (5H, m), 4.09 (1H, m), 4.16 (1H, m), 4.29 (1H, dd, J=6 Hz and 2 Hz), 4.36–4.45 (5H, m), 4.5–4.7 (3H, m), 4.97 (1H, d, J=3 Hz), 5.04 (1H, dd, J=8.6 Hz and 4 Hz), 5.25 (1H, d, J=3.1 Hz), 6.85 (1H, d, J=8.3 Hz), 7.03 (1H, dd, J=8.3 Hz and 2.1 Hz), 7.31 (1H, d, J=2 Hz), 7.52 (1H, d, J=8.6 Hz)

FAB-MS: e/z=1103 (M+Na)

EXAMPLE 9

FR138538 substance (SEQ ID NO: 1) was obtained by reacting FR133303 substance (SEQ ID NO: 1) with benzoyl chloride according to a similar manner to that of Example 6.

IR (Nujol): 3300, 1640, 1240 cm$^{-1}$

NMR (CD$_3$OD, δ): 1.05 (3H, d, J=6.8 Hz), 1.18 (3H, d, J=6 Hz), 1.89–2.12 (3H, m), 2.31–2.53 (3H, m), 2.75 (1H, dd, J=12 Hz and 4 Hz), 3.38 (1H, m), 3.76 (1H, d, J=11Hz), 3.87–3.98 (1H, m), 4.02–4.18 (2H, m), 4.22–4.32 (4H, m), 4.37–4.40 (3H, m), 4.49–4.62 (3H, m), 4.98 (1H, m), 5.02 (1H, m), 5.37 (1H, d, J=3 Hz), 6.85 (1H, d, J=8.3 Hz), 7.04 (1H, dd, J=8.3 Hz and 2 Hz), 7.11–7.50 (6H, m)

FAB-MS: e/z=1101 (M+Na)

EXAMPLE 10

FR138539 substance (SEQ ID NO: 1 ) was obtained by reacting FR133303 substance (SEQ ID NO: 1) with 2-(2-aminothiazol-4-yl)-2-methoxyiminoacetic acid according to a similar manner to that of Example 6.

IR (Nujol): 3300, 1650, 1620, 1520, 1260, 1040 cm$^{-1}$

NMR (CD$_3$OD, δ): 1.05 (3H, d, J=6.8 Hz), 1.21 (3H, d, J=5.9 Hz), 1.89–2.21 (3H, m), 2–29–2.61 (3H, m), 2.78–2.89 (1H, m), 3.32–3.42 (1H, m), 3.76–3.82 (1H, m), 3–91–4.01 (2H, m), 3.95 (3H, s), 4.13 (1H, m), 4.16 (1H, m), 4.24–4.27 (1H, m), 4.32–4.43 (5H, m), 4.46–4.62 (3H, m), 4.97–4.99 (1H, m), 5.08 (1H, m), 5.41 (1H, m), 6.79 (1H, s), 6.86 (1H, d, J=8.1 Hz), 7.04 (1H, dd, J=8.1 Hz and 2 Hz), 7.31 (1H, d, J=2 Hz), 7.51 (1H, d, J=7 Hz)

FAB-MS: e/z=1143 (M$^+$)

EXAMPLE 11

FR138365 substance (SEQ ID NO: 1) obtained by reacting FR133303 substance (SEQ ID NO: 1) with tosyl chloride according to a similar manner to that of Example 6.

IR (Nujol): 3300, 1650, 1620, 1260, 1060 cm$^{-1}$

NMR (CD$_3$OD, δ): 0.75 (3H, d, J=6.8 Hz), 1.07 (3H, d, J=6.0 Hz), 1.61–1.79 (1H, m), 1.91–2.05 (3H, m), 2.30–2.59 (3H, m), 3.36 (1H, m), 3.68 (1H, d, J=11 Hz), 3.81–4.07 (4H, m), 4.22 (1H, m), 4.32–4.40 (5H, m), 4.42–4.60 (3H, m), 4.7 (1H, m), 5.0 (1H, m), 5.42 (1H, d, J=3 Hz), 6.85 (1H, d, J=8.3 Hz), 7.03 (1H, dd, J=8.3 Hz and 2 Hz), 7.29–7.33 (3H, m), 7.75 (1H, d, J=8.3 Hz)

FAB-MS: e/z=1135 (M+Na)

Preparation 11

To a solution of 6-hydroxy-2-naphthoic acid (1 g) in the mixture of 10% sodium hydroxide aqueous solution (4.25 ml) and dimethylsulfoxide (17 ml) was added octyl bromide (0.918 ml). The mixture was stirred for 6 hours at 60° C.

The reaction mixture was added to a mixture of water and ethyl acetate and adjusted to pH 3 with conc. hydrochloric acid. The organic layer was separated and dried over magnesium sulfate. The magnesium sulfate was filtered off, and the filtrate was evaporated under reduced pressure to give 6-octyloxy-2-naphthoic acid (0.91 g).

IR (Nujol): 1670, 1620, 1210 cm$^{-1}$

NMR (DMSO-d$_6$, δ): 0.86 (3H, t, J=6.7 Hz), 1.2–1.6 (10H, m), 1.78 (2H, m), 4.10 (2H, t, J=6.7 Hz), 7.19 (1H, dd, J=2.3 and 8.8 Hz), 7.36 (1H, d, J=2.3 Hz), 7.83 (1H, d, J=8.8 Hz), 7.97 (2H, d, J=8.8 Hz), 8.52 (1H, s)

Preparation 12

1-Ethyl-3-(3-dimethylaminopropyl)carbodiimide hydrochloride (0.703 g) was added to a solution of 6-octyloxy-2-naphthoic acid (0.85 g) and 1-hydroxy-1H-benzotriazole (0.382 g) in ethyl acetate (26 ml). The mixture was stirred for two hours at room temperature.

The reaction mixture was added to water and the separated organic layer was washed with water and sodium chloride aqueous solution. Then the organic layer was dried over magnesium sulfate. The magnesium sulfate was filtered off, and the filtrate was evaporated under reduced pressure to give 1-(6-octyloxy-2-naphthoyl)-1H-benzotriazole-3-oxide (0.74 g).

IR (Nujol): 1770, 1740, 1620, 1190, 1020, 740 cm$^{-1}$

NMR (CDCl$_3$, δ): 0.90 (3H, t, J=6.8 Hz), 1.2–1.6 (10H, m), 1.89 (2H, m), 4.14 (2H, t, J=6.8 Hz), 7.1–7.3 (2H, m), 7.4–7.6 (3H, m), 7.8–8.0 (2H, m), 8.1–8.2 (2H, m), 8.80 (1H, s)

In the following, the structure of the compound of Example 12 is shown.

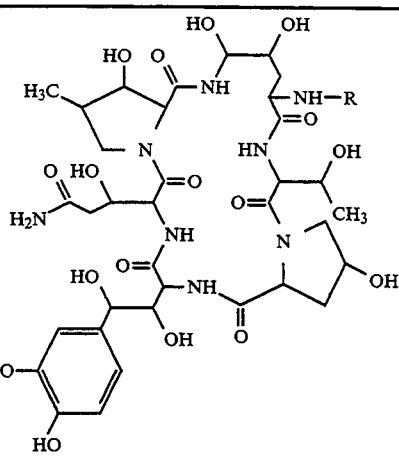

| Example No. | Compound No. | R |
|---|---|---|
| 12 | FR139687 | —CO—(6-octyloxy-2-naphthyl), i.e. —CO-naphthyl-O(CH$_2$)$_7$CH$_3$ |

EXAMPLE 12

To a solution of FR133303 substance (0.5 g) and 1-(6-octyloxy-2-naphthoyl)-1H-benzotriazole-3-oxide (0.271 g) in N,N-dimethylformamide (1.5 ml) was added 4-dimethylaminopyridine (0.0828 g). The mixture was stirred for 12 hours at room temperature.

The reaction mixture was added to water and adjusted to pH 6. The aqueous solution was washed with ethyl acetate, and subjected to ion exchange chromatography on DEAE-Toyopearl (Cl$^-$) (30 ml) and eluted with 50% methanol in 1M sodium chloride solution. The fractions containing the object compound were combined and evaporated under reduced pressure to remove methanol. The aqueous solution was adjusted to pH 4.5 with 1N hydrochloric acid and subjected to column chromatography on Diaion HP-20 (65 ml) and eluted with 80% aqueous methanol. The fractions containing the object compound were combined and evaporated under reduced pressure to remove methanol. The residue was lyophilized to give object acylated compound (hereinafter referred to as FR139687 substance) (0.214 g).

IR (Nujol): 3300, 1620, 1500 cm$^{-1}$

NMR (DMSO-d$_6$+D$_2$O, δ): 0.86 (3H, t, J=6.8 Hz), 0.97 (3H, d, J=6.8 Hz), 1.06 (3H, d, J=6.8 Hz), 1.2–1.5 (10H, m), 1.6–2.0 (5H, m), 2.2–2.5 (3H, m), 2.4–2.6 (1H, m), 3.18 (1H, m), 3.6–3.9 (1H, m), 4.0–4.6 (15H, m), 4.84 (1H, d, J=3 Hz), 4.90 (1H, d, J=3 Hz), 5.11 (1H, d, J=3 Hz), 6.76 (1H, d, J=8.3 Hz), 6.93 (1H, d, J=8.3 Hz), 7.13 (1H, s), 7.25 (1H, d, J=8.3 Hz), 7.39 (1H, s), 7.8–8.0 (3H, m), 8.44 (1H, s)

FAB-MS e/z=1264 (M+Na) The following compounds (Preparations 13 to 16) were obtained according to a similar manner to that of Preparation 5.

Preparation 13

N-(t-Butoxycarbonyl)-L-2-(2-naphthyl)glycine succinimido ester

IR (Nujol): 3350, 1800, 1770, 1730, 1680, 1500, 1200 cm$^{-1}$

Preparation 14

Succinimido 2-(4-biphenylyl)acetate
IR (Nujol): 1800, 1770, 1720, 1200 cm$^{-1}$
NMR (DMSO-d$_6$, δ): 2.82 (4H, s), 4.17 (2H, s), 7.30–7.50 (5H, m), 7.45 (2H, d, J=8.1 Hz), 7.67 (2H, d, J=8.1 Hz)

Preparation 15

Succinimido 4-t-butylbenzoate
IR (Nujol): 1760, 1730, 1200, 1070, 990 cm$^{-1}$
NMR (DMSO-d$_6$, δ): 1.33 (9H, s), 2.89 (4H, s), 7.68 (2H, d, J=8.5 Hz), 8.03 (2H, d, J=8.5 Hz)

Preparation 16

Succinimido 4-(4-phenylbutoxy)benzoate
IR (Nujol): 1730, 1600, 1240, 1170, 1070 cm$^{-1}$
NMR (DMSO-d$_6$, δ): 1.75 (4H, m), 2.65 (2H, m), 4.14 (2H, m), 7.15 (2H, d, J=8.9 Hz), 7.13–7.35 (5H, m), 8.03 (2H, d, J=8.9 Hz)

Preparation 17

To neat 3,7-dimethyloctanol (5 ml) was added phosphorus tribromide (1.01 ml). The mixture was stirred for 4 hours at 60° C. The reaction mixture was added to a mixture of water and n-hexane. The organic layer was separated and dried over magnesium sulfate. The magnesium sulfate was filtered off, and the filtrate was evaporated under reduced pressure to give 3,7-dimethyloctyl bromide (4.40 g).

IR (Neat): 2900, 1450 cm$^{-1}$
NMR (CDCl$_3$, δ): 0.87 (6H, d, J=6.6 Hz), 0.89 (3H, d, J=6.4 Hz), 1.1–1.3 (6H, m), 1.5–1.9 (4H, m), 3.3–3.5 (2H, m)

The following compounds (Preparations 18 to 23) were obtained according to a similar manner to that of Preparation 11.

Preparation 18

4-[4-(Octyloxy)phenoxy]benzoic acid
IR (Nujol): 1680, 1600, 1240, 840 cm$^{-1}$
NMR (DMSO-d$_6$, δ): 0.87 (3H, t, J=6.7 Hz), 1.1–1.6 (10H, m), 1.71 (2H, m), 3.96 (2H, t, J=6.4 Hz), 6.9–7.1 (6H, m), 7.92 (2H, d, J=8.7 Hz), 12.8 (1H, br s)

Preparation 19

6-(Butoxy)-2-naphthoic acid
IR (Nujol): 1660, 1610, 1205 cm$^{-1}$
NMR (DMSO-d$_6$, δ): 0.96 (3H, t, J=7.29 Hz), 1.48 (2H, qt, J=7.29 Hz and 7 Hz), 1.78 (2H, tt, J=7 Hz and qt, J=7.29 Hz and 7 Hz), 1.78 (2H, tt, J=7Hz and 6.45 Hz), 4.12 (2H, t, J=6.45 Hz), 7.24 (1H, dd, J=9.0 Hz and 2.3 Hz), 7.40 (1H, d, J=2.3 Hz), 7.86 (1H, d, J=8.7 Hz), 7.94 (1H, d, J=8.7 Hz), 8.01 (1H, d, J=9.0 Hz), 8.52 (1H, s)

Preparation 20

6-Decyloxy-2-naphthoic acid
IR (Nujol): 1670, 1620, 1210 cm$^{-1}$
NMR (DMSO-d$_6$, δ): 0.85 (3H, t, J=6.7 Hz), 1.2–1.6 (14H, m), 1.78 (2H, m), 4.11 (2H, t, J=6.4 Hz), 7.23 (1H, dd, J=8.9 Hz and 2.4 Hz), 7.39 (1H, d, J=2.4 Hz), 7.86 (1H, d, J=8.7 Hz), 7.93 (1H, d, J=8.7 Hz), 8.01 (1H, d, J=8.9 Hz), 8.5 (1H, s)

Preparation 21

6-Hexyloxy-2-naphthoic acid
IR (Nujol): 1660, 1620, 1290, 1210 cm$^{-1}$
NMR (DMSO-d$_6$, δ): 0.89 (3H, t, J=6.8 Hz), 1.2–1.6 (6H, m), 1.78 (2H, quint, J=6.5 Hz), 4.11 (2H, t, J=6.5 Hz), 7.23 (1H, dd, J=9.0 Hz and 2.4 Hz), 7.39 (1H, d, J=2.4 Hz), 7.86 (1H, d, J=8.7 Hz), 7.94 (1H, d, J=8.7 Hz), 8.01 (1H, d, J=9.0 Hz), 8.52 (1H, s)

Preparation 22

6-Dodecyloxy-2-naphthoic acid
IR (Nujol): 1670, 1620, 1210 cm$^{-1}$
NMR (DMSO-d$_6$, δ): 0.85 (3H, t, J=6.7 Hz), 1.20–1.60 (18H, m), 1.78 (2H, m), 4.11 (2H, t, J=6.5 Hz), 7.22 (1H, dd, J=9.0 Hz and 2.4 Hz), 7.39 (1H, d, J=2.4 Hz), 7.85 (1H, d, J=8.7 Hz), 7.93 (1H, d, J=8.7 Hz), 8.00 (1H, d, J=9.0 Hz), 8.51 (1H, s), 12.90 (1H, s)

Preparation 23

6-(3,7-Dimethyloctyloxy)-2-naphthoic acid
IR (Nujol): 1660, 1610, 1290, 1210 cm$^{-1}$
NMR (DMSO-d$_6$, δ): 0.84 (6H, d, J=6.6 Hz), 0.94 (3H, d, J=6.1 Hz), 1.1–1.4 (6H, m), 1.4–1.9 (4H, m), 4.15 (2H, t, J=6.7 Hz), 7.22 (1H, dd, J=9.0 Hz and 2.4 Hz), 7.4i (1H, d, J=2.4 Hz), 7.86 (1H, d, J=8.6 Hz), 7.93 (1H, d, J=8.6 Hz), 8.01 (1H, d, J=9.0 Hz), 8.52 (1H, s)

The following compounds (Preparations 24 to 31) were obtained according to a similar manner to that of Preparation 12.

Preparation 24

1-[4-(4-Octyloxy)phenoxy]benzoyl-1H-benzotriazole-3-oxide
IR (Nujol): 1770, 1730, 1600, 1500, 1230, 980 cm$^{-1}$

Preparation 25

1-(6-Butoxy-2-naphthoyl)-1H-benzotriazole-3-oxide
IR (Nujol): 1760, 1610, 1260, 1180, 1020 cm$^{-1}$

Preparation 26

1-(6-Decyloxy-2-naphthoyl)-1H-benzotriazole-3-oxide
IR (Nujol): 1780, 1620, 1190, 1000 cm$^{-1}$

Preparation 27

1-(6-Hexyloxy-2-naphthoyl)-1H-benzotriazole-3-oxide
IR (Nujol): 1780, 1610, 1190 cm$^{-1}$
NMR (DMSO-d$_6$, δ): 0.89 (3H, t, J=6.7 Hz), 1.2–1.6 (6H, m), 1.79 (2H, m), 4.12 (2H, t, J=6.5 Hz), 7.24 (1H, dd, J=9.0 Hz and 2.4 Hz), 7.39 (1H, d, J=2.4 Hz), 7.41 (1H, t, J=8 Hz), 7.54 (1H, t, J=8 Hz), 7.72 (1H, d, J=8 Hz), 7.88 (1H, d, J=8.7 Hz), 7.90 (1H, d, J=8.7 Hz), 7.97 (1H, d, J=8 Hz), 8.02 (1H, d, J=9.0 Hz), 8.51 (1H, s)

Preparation 28

1-(6-Dodecyloxy-2-naphthoyl)-1H-benzotriazole-3-oxide
IR (Nujol): 1770, 1620, 1190, 1030, 730 cm$^{-1}$
NMR (DMSO-d$_6$, δ): 0.85 (3H, t, J=6.7 Hz), 1.2–1.3 (18H, m), 1.78 (2H, m), 4.11 (2H, t, J=6.5 Hz), 7.22 (1H, dd, J=9.0 Hz and 2.4 Hz), 7.39 (1H, d, J=2.4 Hz), 7.40 (1H, t, J=8 Hz), 7.55 (1H, t, J=8 Hz), 7.73 (1H, d, J=8 Hz), 7.85 (1H, d, J=8.7 Hz), 7.93 (1H, d, J=8.7 Hz), 7.99 (1H, d, J=8 Hz), 8.00 (1H, d, J=9.0 Hz), 8.51 (1H, s)

Preparation 29

1-[6-(3,7-Dimethyloctyloxy)-2-naphthoyl]-1H-benzotriazole-3-oxide

IR (Nujol): 1780, 1620, 1190 cm$^{-1}$

Preparation 30

1-[(2E,6E)-3,7,11-Trimethyl-2,6,10-dodecatrienoyl]-1H-benzotriazole-3-oxide

IR (Neat): 2900, 1780, 1620, 1420, 1070 cm$^{-1}$

Preparation 31

3,7-Dimethyl-6-octenyl bromide was obtained according to a similar manner to that of Preparation 17.

IR (Neat): 2900, 1440, 1380 cm$^{-1}$

NMR (DMSO-d$_6$, δ): 0.86 (3H, d, J=6.3 Hz), 1.0–1.5 (2H, m), 1.57 (3H, s), 1.65 (3H, s), 1.7–2.1 (5H, m), 3.4–.3.7 (2H, m), 5.08 (1H, m)

Preparation 32

To a suspension of sodium hydride (2.04 g) in N,N-dimethylformamide (50 ml) was added 4-hydroxypyridine (5 g) at room temperature. Octyl bromide (9.08 ml) was added thereto. The mixture was stirred for 2 hours at 50° C. The reaction mixture was added to a mixture of brine (100 ml), trtrahydrofuran (100 ml) and ethyl acetate (100 ml). The organic layer was separated and dried over magnesium sulfate. The magnesium sulfate was filtered off, and the filtrate was evaporated under reduced pressure to give 1-octyl-4-pyridone (14.7 g).

NMR (DMSO-d$_6$, δ): 0.86 (3H, t, J=6 Hz), 1.1–1.4 (10H, m), 1.4–1.8 (2H, m), 3.81 (2H, t, J=7 Hz), 6.05 (2H, d, J=8 Hz), 7.63 (2H, d, J=8 Hz)

Preparation 33

To a solution of 1-octyl-4-pyridone (10.9 g) in pyridine (100 ml) was added phosphorous pentasulfide (8.65 g) at room temperature. The mixture was stirred for 3 hours at 80° C. The reaction mixture was added to a mixture of water (200 ml) and methylene chloride (200 ml). The organic layer was separated and dried over magnesium sulfate. The magnesium sulfate was filtered off, and the filtrate was evaporated under reduced pressure to give 1-octyl-1,4-dihydropyridine-4-thione (5.27 g).

IR (Neat): 2910, 2850, 1620, 1460, 1110 cm$^{-1}$

NMR (DMSO-d$_6$, δ): 0.86 (3H, t, J=6 Hz), 1.1–1.4 (10H, m), 1.5–1.9 (2H, m), 3.95 (2H, t, J=7 Hz), 7.13 (2H, d, J=7 Hz), 7.60 (2H, d, J=7 Hz)

The following compounds (Preparations 34 to 36) were obtained according to a similar manner to that of Preparation 1.

Preparation 34

Methyl 2-(4-hydroxyphenyl)-2-methoxyacetate

IR (Nujol): 3350, 1740, 1610, 1600, 1220, 1100 cm$^{-1}$

NMR (DMSO-d$_6$, δ): 3.23 (3H, s), 3.60 (3H, s), 4.73 (1H, s), 6.72 (2H, d, J=8.9 Hz), 7.15 (2H, d, J=8.9 Hz)

EI-MS (e/z)=196 (M$^+$)

Preparation 35

D-Tyrosine methyl ester hydrochloride

IR (Nujol): 3300, 1740, 1220 cm$^{-1}$

NMR (DMSO-d$_6$, δ): 3.02 (2H, m), 3.67 (3H, s), 4.16 (1H, t, J=6.7 Hz), 6.72 (2H, d, J=8.4 Hz), 7.01 (2H, d, J=8.4 Hz), 8.58 (2H, s), 9.47 (1H, s)

Preparation 36

Methyl (4-hydroxyphenyl)glyoxylate

IR (Nujol): 3380, 1730, 1700, 1600, 1580, 1220 cm$^{-1}$

NMR (DMSO-d$_6$, δ): 3.91 (3H, s), 6.94 (2H, d, J=8.8 Hz), 7.83 (2H, d, J=8.8 Hz), 10.9 (1H, s)

Preparation 37

N-(t-Butoxycarbonyl)-D-tyrosine methyl ester was obtained according to a similar manner to that of Preparation 2.

IR (Nujol): 3360, 1700, 1680, 1290, 1270, 1250 cm$^{-1}$

NMR (DMSO-d$_6$, δ): 1.33 (9H, s), 2.73 (2H, m), 3.59 (3H, s), 4.05 (1H, m), 6.65 (2H, d, J=8.4 Hz), 7.00 (2H, d, J=8.4 Hz), 7.23 (1H, d, J=7.9 Hz), 9.23 (1H, s)

Preparation 38

To a solution of L-tyrosine methyl ester hydrochloride (1 g) in water (1.5 ml) was added sodium bicarbonate (0.363 g) under ice-cooling and stirred for 10 minutes, and then acetonitrile (7 ml), 37% formaldehyde aqueous solution (0.637 ml) and sodium cyanoborohydride (0.182 g) was added thereto at −5° C. The mixture was stirred for 2 hours at −5° C. The resultant insoluble material was filtered off, and the filtrate was extracted with ethyl acetate. The organic layer was separated and dried over magnesium sulfate. The magnesium sulfate was filtered off, and the filtrate was evaporated under reduced pressure to give N,N-dimethyl-L-tyrosine methyl ester (0.21 g).

IR (Nujol): 1730, 1260, 1010 cm$^{-1}$

NMR (DMSO-d$_6$, δ): 2.24 (6H, s), 2.72 (2H, m), 3.34 (1H, m), 3.53 (3H, s), 6.54 (2H, d, J=8.4 Hz), 6.97 (2H, d, J=8.4 Hz), 9.18 (1H, s)

The following compounds (Preparations 39 to 44) were obtained according to a similar manner to that of Preparation 3.

Preparation 39

Methyl 2-(4-octyloxyphenyl)acetate

IR (Neat): 2910, 2850, 1730, 1240 cm$^{-1}$

NMR (DMSO-d$_6$, δ): 0.86 (3H, t, J=6.3 Hz), 1.2–1.5 (10H, m), 1.6–1.9 (2H, m), 3.58 (2H, s), 3.59 (3H, s), 3.92 (2H, t, J=6.4 Hz), 6.85 (2H, d, J=8.7 Hz), 7.15 (2H, d, J=8.7 Hz)

Preparation 40

Ethyl 3-(4-octyloxyphenyl)propionate

IR (Neat): 2920, 2850, 1730, 1240 cm$^{-1}$

NMR (DMSO-d$_6$, δ): 0.86 (3H, t, J=6.7 Hz), 1.15 (3H, t, J=7.1 Hz), 1.2–1.5 (10H, m), 1.6–1.8 (2H, m), 2.55 (2H, t, J=7.2 Hz), 2.77 (2H, t, J=7.2 Hz), 3.90 (2H, t, J=6.4 Hz), 4.03 (2H, q, J=7.1 Hz), 6.81 (2H, d, J=8.6 Hz), 7.11 (2H, d, J=8.6 Hz)

Preparation 41

Methyl 2-(4-octyloxyphenyl)-2-methoxyacetate

IR (Neat): 2910, 2850, 1740, 1600, 1240, 1100 cm$^{-1}$

NMR (DMSO-d$_6$, δ): 0.86 (3H, t, J=6.8 Hz), 1.2–1.5 (10H, m), 1.6–1.8 (2H, m), 3.26 (3H, s), 3.62 (3H, s), 3.94 (2H, t, J=6.4 Hz), 4.83 (1H, s), 6.91 (2H, d, J=8.7 Hz), 7.27 (2H, d, J=8.7 Hz)

EI-MS (e/z)=308 (M$^+$)

Preparation 42

O$^4$-Octyl-N-(t-butoxycarbonyl)-D-tyrosine methyl ester

IR (Nujol): 3350, 1730, 1680, 1510, 1240, 1160 cm$^{-1}$

NMR (DMSO-d$_6$, δ): 0.86 (3H, t, J=6.7 Hz), 1.2–1.3 (10H, m), 1.68 (2H, m), 2.82 (2H, m), 3.60 (3H, s), 3.91 (2H, t, J=7.3 Hz), 4.08 (1H, m), 6.81 (2H, d, J=8.6 Hz), 7.12 (2H, d, J=8.6 Hz), 7.25 (1H, d, J=8.0 Hz)

Preparation 43

O⁴-Octyl-N,N-dimethyl-L-tyrosine methyl ester
IR (Neat): 2930, 2860, 1730, 1250 cm⁻¹
NMR (DMSO-d₆, δ): 0.86 (3H, t, J=6.6 Hz), 1.26 (10H, m), 1.68 (2H, m), 2.80 (2H, m), 3.33 (6H, s), 3.37 (1H, m), 3.53 (3H, s), 3.89 (2H, t, J=6.4 Hz), 6.79 (2H, d, J=8.6 Hz), 7.08 (2H, d, J=8.6 Hz)

Preparation 44

Methyl (4-octyloxyphenyl)glyoxylate
IR (Neat): 2930, 2850, 1730, 1670, 1600, 1260, 1210, 1160 cm⁻¹
NMR (DMSO-d₆, δ): 0.86 (3H, t, J=6.3 Hz), 1.2-1.5 (10H, m), 1.6-1.9 (2H, m), 3.93 (3H, s), 4.10 (2H, t, J=6.8 Hz), 7.12 (2H, d, J=8.9 Hz), 7.92 (2H, d, J=8.9 Hz)

The following compounds (Preparations 45 to 51) were obtained according to a similar manner to that of Preparation 4.

Preparation 45

4-(2-Butoxyethoxy)benzoic acid
IR (Nujol): 1670, 1610, 1260 cm⁻¹
NMR (DMSO-d₆, δ): 0.87 (3H, t, J=7.2 Hz), 1.2-1.6 (4H, m), 3.45 (2H, t, J=6.4 Hz), 3.70 (2H, t, J=4.4 Hz), 4.16 (2H, t, J=4.4 Hz), 7.02 (2H, d, J=8.9 Hz), 7.88 (2H, d, J=8.9 Hz), 12.63 (1H, s)

Preparation 46

2-(4-Octyloxyphenyl)acetic acid
IR (Nujol): 1680, 1240, 820, 780 cm⁻¹
NMR (DMSO-d₆, δ): 0.86 (3H, t, J=6.8 Hz), 1.1-1.5 (10H, m), 1.6-1.8 (2H, m), 3.47 (2H, s), 3.92 (2H, t, J=6.4 Hz), 6.84 (2H, d, J=8.6 Hz), 7.14 (2H, d, J=8.6 Hz)

Preparation 47

3-(4-Octyloxyphenyl)propionic acid
IR (Nujol): 1680, 1500, 1200 cm⁻¹
NMR (DMSO-d₆, δ): 0.86 (3H, t, J=6.3 Hz), 1.1-1.5 (10H, m), 1.6-1.8 (2H, m), 2.47 (2H, t, J=7.2 Hz), 2.74 (2H, t, J=7.2 Hz), 3.90 (2H, t, J=6.4 Hz), 6.81 (2H, d, J=8.6 Hz), 7.11 (2H, d, J=8.6 Hz), 12.10 (1H, br s)

Preparation 48

2-(4-Octyloxyphenyl)-2-methoxyacetic acid
IR (Nujol): 1760, 1720, 1600, 1500, 1240, 1180, 1100, 830 cm⁻¹
NMR (DMSO-d₆, δ): 0.86 (3H, t, J=6.7 Hz), 1.2-1.5 (10H, m), 2.6-2.8 (2H, m), 3.26 (3H, s), 3.94 (2H, t, J=6.4 Hz), 4.67 (1H, s), 6.90 (2H, d, J=8.6 Hz), 7.27 (2H, d, J=8.6 Hz)

Preparation 49

O⁴-Octyl-N-(t-butoxycarbonyl)-D-tyrosine
IR (Nujol): 3400, 2900, 1700, 1500, 1240, 1160 cm⁻¹
NMR (DMSO-d₆, δ): 0.859 (3H, t, J=6.8 Hz), 1.20-1.30 (10H, m), 1.32 (9H, s), 1.68 (2H, m), 2.67-2.95 (1H, m), 3.90 (2H, t, J=7 Hz), 4.01 (1H, m), 6.81 (2H, d, J=8.6 Hz), 7.02 (2H, d, J=8.3 Hz), 7.13 (2H, d, J=8.6 Hz)

Preparation 50

O⁴-Octyl-N,N-dimethyl-L-tyrosine
IR (Neat): 2940, 2860, 2600, 1620, 1240 cm⁻¹
NMR (DMSO-d₆, δ): 0.86 (3H, t, J=6.6 Hz), 1.26 (10H, m), 1.68 (2H, m), 2.67 (6H, s), 2.8-3.6 (3H, m), 3.91 (2H, t, J=6.4 Hz), 6.85 (2H, d, J=8.5 Hz), 7.16 (2H, d, J=8.5 Hz)

Preparation 51

O⁴-Octyloxyphenyl)glyoxylic acid
IR (Neat): 1730, 1670, 1600, 1260, 1160 cm⁻¹
NMR (DMSO-d₆, δ): 0.86 (3H, t, J=6.8 Hz), 1.2-1.5 (10H, m), 1-65-1.85 (2H, m), 4.09 (2H, t, J=6.5 Hz), 7.12 (2H, d, J=8.9 Hz), 7.89 (2H, d, J=8.9 Hz)

Preparation 52

Nᵀ-Octyl-N-(t-butoxycarbonyl)-L-histidine was obtained from N-(t-butoxycarbonyl)-L-histidine methyl ester according to similar manners to those of Preparations 3 and 4.
NMR (DMSO-d₆, δ): 0.85 (3H, t, J=6.3 Hz), 1.23 (10H, m), 1.35 (9H, s), 2.83 (2H, m), 3.90 (2H, t, J=7 Hz), 4.0-4.2 (1H, m), 6.36 (1H, s), 7.02 (1H, d, J=8 Hz), 7.75 (1H, s)

The following compounds (Preparations 53 to 60) were obtained according to a similar manner to that of Preparation 11.

Preparation 53

4-Octyloxyphthalic acid
IR (Neat): 2930, 2860, 2500, 1700, 1600, 1260 cm⁻¹
NMR (DMSO-d₆, δ): 0.86 (3H, t, J=6.8 Hz), 1.2-1.5 (10H, m), 1.5-1.8 (2H, m), 4.05 (2H, t, J=6.2 Hz), 7.03 (1H, d, J=2.6 Hz), 7.06 (1H, dd, J=8.4 Hz and 2.6 Hz), 7.72 (1H, d, J=8.4 Hz)

Preparation 54

3-Methoxy-4-octyloxybenzoic acid
IR (Nujol): 2600, 1680, 1600, 1270, 1230 cm⁻¹
NMR (DMSO-d₆, δ): 0.86 (3H, t, J=6.8 Hz), 1.2-1.5 (10H, m), 1.6-1.8 (2H, m), 3.80 (3H, s), 4.01 (2H, t, J=6.5 Hz), 7.03 (1H, d, J=8.5 Hz), 7.44 (1H, d, J=1.9 Hz), 7.54 (1H, dd, J=8.5 Hz and 1.9 Hz)

Preparation 55

4-(4-Octyloxyphenyl)benzoic acid
IR (Nujol): 1670, 1600, 830, 770 cm⁻¹
NMR (DMSO-d₆, δ): 0.87 (3H, t, J=6.7 Hz), 1.2-1.5 (10H, m), 1.6-1.8 (2H, m), 4.01 (2H, t, J=6.4 Hz), 7.04 (2H, d, J=8.8 Hz), 7.68 (2H, d, J=8.8 Hz), 7.75 (2H, d, J=8.5 Hz), 7.99 (2H, d, J=8.5 Hz)

Preparation 56

6-(2-Ethylhexyloxy)-2-naphthoic acid
IR (Nujol): 1660, 1610, 1280, 1200 cm⁻¹
NMR (DMSO-d₆, δ): 0.88 (3H, t, J=7.3 Hz), 0.92 (3H, t, J=7.3 Hz), 1.2-1.6 (8H, m), 1.7-1.9 (1H, m), 4.01 (2H, d, J=5.7 Hz), 7.23 (1H, dd, J=8.9 and 2.4 Hz), 7.42 (1H, d, J=2.4 Hz), 7.86 (1H, d, J=8.7 Hz), 7.94 (1H, d, J=8.7 Hz), 8.01 (1H, d, J=8.9 Hz), 8.51 (1H, s), 12.9 (1H, s)

Preparation 57

6-(3,7-Dimethyl-6-octenyloxy)naphthoic acid
IR (Nujol): 1660, 1610, 1290, 1200 cm⁻¹
NMR (DMSO-d₆, δ): 0.95 (3H, d, J=6.1 Hz), 1.1-1.5 (2H, m), 1.57 (3H, s), 1.64 (3H, s), 1.6-2.1 (5H, m), 4.15 (2H, t, J=6.7 Hz), 5.10 (1H, t, J=7.1 Hz), 7.22 (1H, dd, J=8.9 Hz and 2.3 Hz), 7.42 (1H, d, J=2.3 Hz), 7.86 (1H, d, J=8.6 Hz), 7.94 (1H, d, J=8.6 Hz), 8.01 (1H, d, J=8.9 Hz), 8.52 (1H, s), 12.89 (1H, s)

Preparation 58

6-(3 7-Dimethyl-2,6-octadienyloxy)naphthoic acid
IR (Nujol): 1660, 1620, 1210 cm$^{-1}$
NMR (DMSO-d$_6$, δ): 1.57 (3H, s), 1.60 (3H, s), 1.76 (3H, s), 2.07 (4H, m), 4.70 (2H, d, J=6.5 Hz), 5.07 (1H, m), 5.51 (1H, t, J=6.5 Hz), 7.24 (1H, dd, J=8.9 Hz and 2.4 Hz), 7.41 (1H, d, J=2.4 Hz), 7.85 (1H, d, J=8.7 Hz), 7.94 (1H, d, J=8.7 Hz), 8.01 (1H, d, J=8.9 Hz), 8.52 (1H, s), 12.88 (1H, s)

Preparation 59

(2E)-3-(4-Octyloxyphenyl)acrylic acid
IR (Nujol): 1660, 1600, 1240 cm$^{-1}$
NMR (DMSO-d$_6$, δ): 0.86 (3H, t, J=6.7 Hz), 1.2–1.5 (10H, m), 1.6–1-8 (2H, m), 4.00 (2H, t, J=6.4 Hz), 6.36 (1H, d, J=16 Hz), 6.95 (2H, d, J=8.7 Hz), 7.54 (1H, d, J=16 Hz), 7.61 (2H, d, J=8.7 Hz), 12.20 (1H, br s)

Preparation 60

Sodium 6-octyloxy-2-naphthalene sulfonate
IR (Nujol): 1230, 1180, 860, 820 cm$^{-1}$
NMR (DMSO-d$_6$, δ): 0.86 (3H, t, J=6 Hz), 1.1–1.6 (10H, m), 4.06 (2H, t, J=5 Hz), 7.08 (1H, d, J=9 Hz), 7.21 (1H, s), 7.79 (1H, d, J=9 Hz), 8.00 (1H, s)

Preparation 61

To a solution of thionyl chloride (0.692 ml) and N,N-dimethylformamide (0.022 ml) was added sodium 6-octyloxy-2-naphthalenesulfonate (1 g) under ice-cooling and stirred for 1.5 hours at 95° C. The reaction mixture was evaporated under reduced pressure to give 6-octyloxy-2-naphthylsulfonyl chloride (1 g).

IR (Nujol): 1610, 1260, 1160 cm$^{-1}$
NMR (CDCl$_3$, δ): 0.90 (3H, t, J=6.2 Hz), 1.2–1.7 (10H, m), 1.8–2.0 (2H, m), 4.12 (2H, t, J=6.5 Hz), 7.20 (1H, d, J=2.2 Hz), 7.32 (1H, dd, J=9.0 Hz and 2.2 Hz), 7.84–7.97 (3H, m), 8.49 (1H, s)

The following compounds (Preparations 62 to 63 to 71) were obtained according to a similar manner to that of Preparation 12.

Preparation 62

1-(4-Octylbenzoyl)-1H-benzotriazole-3-oxide
IR (Neat): 2930, 2850, 1780, 1610, 1240, 990 cm$^{-1}$

Preparation 63

1-[4-(4-Octyloxyphenyl)benzoyl]-1H-benzotriazole-3-oxide
IR (Nujol): 1770, 1600, 980 cm$^{-1}$

Preparation 64

1-[6-(2-Ethylhexyloxy)-2-naphthoyl]-1H-benzotriazole-3-oxide
IR (Nujol): 1770, 1620, 1270, 1180 cm$^{-1}$
NMR (CDCl$_3$, δ): 0.93 (3H, t, J=7.1 Hz), 0.98 (3H, t, J=7.4 Hz), 1.3–1.7 (8H, m), 1.7–2.0 (1H, m), 4.03 (2H, d, J=5.7 Hz), 7.22 (1H, d, J=2.2 Hz), 7.29 (1H, dd, J=8.9 Hz, 2.2 Hz), 7.4–7.7 (3H, m), 7.87 (1H, d, J=9.5 Hz), 7.92 (1H, d, J=9.5 Hz), 8.1–8.2 (2H, m), 8.80 (1H, s)

Preparation 65

1-[6-(3,7-Dimethyl-6-octenyloxy)-2-naphthoyl]-1H-benzotriazole-3-oxide
IR (Neat): 2900, 1770, 1620, 1180 cm$^{-1}$

Preparation 66

1-[6-{(E)-3,7-Dimethyl-2,6-octadienyloxy}-2-naphthoyl]-1H-benzotriazole-3-oxide
IR (Nujol): 1770, 1620, 1270, 1180 cm$^{-1}$

Preparation 67

1-(2-Anthrylcarbonyl)-1H-benzotriazole-3-oxide
IR (Nujol): 1780, 1200, 720, 740 cm$^{-1}$

Preparation 68

1-[2-(4-Octyloxyphenyl)acetyl]-1H-benzotriazole-3oxide
IR (Nujol): 1730, 1460, 1420, 1250, 1130 cm$^{-1}$

Preparation 69

1-[3-(4-Octyloxyphenyl)propionyl]-1H-benzotriazole-3-oxide
IR (Nujol): 1730, 1420, 1340, 1240, 950 cm$^{-1}$

Preparation 70

1-[(E)-3-(4-Octyloxyphenyl)acryloyl]-1H-benzotriazole-3-oxide
IR (Nujol): 1770, 1600, 1260, 1080 cm$^{-1}$

Preparation 71

1-(O$^4$-Octyl-N,N-dimethyl-L-tyrosyl)-1H-benzotriazole-3-oxide
IR (Neat): 2930, 2850, 1800, 1610 cm$^{-1}$

Preparation 72

To a suspension of lithium aluminum hydride (4.05 g) in tetrahydrofuran (475 ml) was added dropwise a solution of 4-octyloxybenzaldehyde (25 g) in tetrahydrofuran (25 ml) at 55°~60° C. The reaction mixture was stirred under reflux for 1 hour, and thereto was added sodium fluoride (35.84 g) and water (11.52 ml) under ice-cooling. The mixture was stirred for 30 minutes, and filtrated. The filtrate was evaporated in vacuo to give 4-octyloxybenzyl alcohol (25.1 g) as crystals.

IR (Nujol): 3200, 1605, 1510 cm$^{-1}$
NMR (DMSO-d$_6$, δ): 0.86 (3H, t, J=6.7 Hz), 1.26–1.38 (10H, m), 1.62–1.72 (2H, m), 3.92 (2H, t, J=6.5 Hz), 4.40 (2H, d, J=5.7 Hz), 5.03 (1H, t, J=5.7 Hz), 6.85 (2H, d, J=8.6 Hz), 7.20 (2H, d, J=8.6 Hz)

Preparation 73

To a suspension of 4-octyloxybenzyl alcohol (25 g), N-hydroxyphthalimide (17.15 g) and triphenylphosphine (27.74 g) in tetrahydrofuran (250 ml) was added dropwise diethyl azodicarboxylate (18.4 g) under ice-cooling. The reaction mixture was stirred at room temperature for 2 hours, and evaporated in vacuo. The residue was purified by chromatography on silica gel to give N-(4-octyloxybenzyloxy)phthalimide (33.45 g) as crystals.

IR (Nujol): 1780, 1725, 1605, 1580, 1505 cm$^{-1}$
NMR (DMSO-d$_6$, δ): 0.86 (3H, m), 1.26 (10H, m), 1.70 (2H, m), 3.95 (2H, t, J=6.5 Hz), 5.08 (2H, s), 6.93 (2H, d, J=8.6 Hz), 7.40 (2H, d, J=8.6 Hz), 7.85 (4H, s)

Preparation 74

To a solution of N-(4-octyloxybenzoyloxy)phthalimide (4.13 g) in tetrahydrofuran (16 ml) was added hydrazine-hydrate (0.53 ml) at room temperature. After the mixture was stirred at the same temperature for 1 hour, the precipitate was filtered off. To the filtrate was added water (6 ml) and 4-hydroxyphenylglyoxylic acid (1.5 g) at room temperature. The mixture was maintained at pH 4~4.5 with aqueous sodium bicarbonate solution for 2 hours, thereto was added ethyl acetate, and adjusted to pH 2 with 1N hydrochloric acid. The separated organic layer was washed with brine, and dried over magnesium sulfate. The organic solvent was evaporated in vacuo to give (4-hydroxyphenyl)-2-(4-octyloxybenzyloxyimino)acetic acid (3.4 g).
IR (Nujol): 3400, 1715, 1605, 1590, 1505 cm$^{-1}$
NMR (DMSO-d$_6$, δ): 0.86 (3H, m), 1.25 (10H, m), 1.69 (2H, m), 3.94 (2H, t, J=6.4 Hz), 5.07 (2H, s), 6.82 (2H, d, J=8.7 Hz), 6.90 (2H, d, J=8.6 Hz), 7.29 (2H, d, J=8.6 Hz), 7.35 (2H, d, J=8.7 Hz)

The following compounds (Preparations 75 and 76) were obtained according to a similar manner to that of Preparation 74.

Preparation 75

2-Phenyl-2-(4-octyloxybenzyloxyimino)acetic acid
IR (Nujol): 1720, 1610, 1585, 1515 cm$^{-1}$
NMR (DMSO-d$_6$, δ): 0.86 (3H, t, J=6.7 Hz), 1.26 (10H, m), 1.69 (2H, m), 3.94 (2H, t, J=6.5 Hz), 5.13 (2H, s), 6.91 (2H, d, J=8.6 Hz), 7.22–7.49 (7H, m)

Preparation 76

2-(4-Octyloxybenzyloxyimino)acetic acid
IR (Nujol): 1700, 1670, 1600 cm$^{-1}$
NMR (DMSO-d$_6$, δ): 0.86 (3H, t, J=6.2 Hz), 1.26 (10H, m), 1.70 (2H, m), 3.95 (2H, t, J=6.5 Hz), 5.13 (2H, s), 6.91 (2H, d, J=8.6 Hz), 7.29 (2H, d, J=8.6 Hz), 7.56 (1H, s)

Preparation 77

A solution of 4-octyloxyphenylglyoxylic acid (0.935 g) in a mixture of water (9 ml) and tetrahydrofuran (18 ml) and adjusted to pH 3.5–4 with 1N hydrochloric acid and methoxyamine hydrochloride (0.337 g) was added thereto at room temperature. The mixture was stirred for 2 hours at room temperature maintaining pH 3.5~4 with 1N hydrochloric acid. The reaction mixture was added to ethyl acetate. The organic layer was separated and dried over magnesium sulfate. The magnesium sulfate was filtered off, and the filtrate was evaporated under reduced pressure to give 2-(4-octyloxyphenyl)-2-methoxyiminoacetic acid (0.57 g).
IR (Nujol): 1700, 1600, 1250, 1030 cm$^{-1}$
NMR (DMSO-d$_6$, δ): 0.86 (3H, t, J=6.3 Hz), 1.2–1.5 (10H, m), 1.6–1.8 (2H, m), 3.89 (3H, s), 3.99 (2H, t, J=6.4 Hz), 7.00 (2H, d, J=8.9 Hz), 7.45 (2H, d, J=8.9 Hz), 14.05 (1H, s)

Preparation 78

To a mixture of 2,3,4,5,6-pentafluorobenzoic acid (1 g) and 2,2,3,3,4,4,5,5-octafluoropentanol (1.18 g) in N,N-dimethylformamide (5 ml) was added 62% sodium hydride (0.39 g) at room temperature. The mixture was stirred at the same temperature for 1 hour, and thereto was added a mixture of water and ethyl acetate. The separated organic layer was washed with water and brine, dried over magnesium sulfate, and evaporated in vacuo. The residue was purified by chromatography on silica gel to give 4-(2,2,3,3,4,4,5,5-octafluoropentyloxy)-2,3,5,6-tetrafluorobenzoic acid (923.0 mg).
IR (Nujol): 1700, 1580 cm$^{-1}$
NMR (DMSO-d$_6$, δ): 4.96 (2H, t, J=14.2 Hz), 7.10 (1H, tt, J=5.6 Hz and 50.2 Hz)

Preparation 79

4-(2,2,3,3,4,4,5,5,6,6,7,7,8,8,8-Pentadecafluorooctyloxy)-2,3,5,6-tetrafluorobenzoic acid
IR (Nujol): 3400, 1640, 1560 cm$^{-1}$
NMR (DMSO-d$_6$, δ): 4.95 (2H, t, J=14.0 Hz)

The following compounds (Preparations 80 to 90) were obtained according to a similar manner to that of Preparation 5.

Preparation 80

Succinimido 2-(4-hydroxyphenyl)-2-(4-octyloxybenzyloxyimino)acetate
IR (Nujol): 1800, 1770, 1700, 1600 cm$^{-1}$

Preparation 81

Succinimido 2-Phenyl-2-(4-octyloxybenzyloxyimino)acetate
IR (Nujol): 1780, 1730, 1605 cm$^{-1}$
NMR (DMSO-d$_6$, δ): 0.86 (3H, m), 1.26 (10H, m), 1.69 (2H, m), 2.90 (4H, m), 3.94 (2H, t, J=6.4 Hz), 5.30 (2H, s), 6.91 (2H, d, J=8.6 Hz), 7.25–7.56 (7H,

Preparation 82

Succinimido 2-(4-Octyloxybenzyloxyimino)acetate
IR (Nujol) 1760, 1725, 1600, 1580 cm$^{-1}$
NMR (DMSO-d$_6$, δ): 0.86 (3H, t, J=6.7 Hz), 1.26 (10H, m), 1.70 (2H, m), 2.85 (4H, s), 3.96 (2H, m), 5.28 (2H, s), 6.91 (2H, d, J=8.6 Hz), 7.33 (2H, d, J=8.6 Hz), 8.12 (1H, s)

Preparation 83

Succinimido 4-(2,2,3,3,4,4,5,5-octafluoropentyloxy)-2,3,5,6-tetraflurobenzoate
IR (Nujol): 3500, 1770, 1740, 1640 cm$^{-1}$
NMR (DMSO-d$_6$, δ): 2.90 (4H, s), 5.23 (2H, t, J=13.8 Hz), 7.11 (1H, tt, J=50.2 Hz and 5.6 Hz)

Preparation 84

Succinimido 4-(2,2,3,3,4,4,5,5,6,6,7,7,8,8,8-pentadecafluorooctyloxy)-2,3,5,6-tetrafluorobenzoate
IR (Nujol): 1735, 1620, 1600 cm$^{-1}$
NMR (DMSO-d$_6$, δ): 2.90 (4H, s), 5.12 (2H, t, J=13.8 Hz)

Preparation 85

Succinimido 3-methoxy-4-octyloxybenzoate
IR (Nujol): 1760, 1730, 1600, 1280, 1200, 880 cm$^{-1}$
NMR (DMSO-d$_6$, δ): 0.86 (3H, t, J=6.7 Hz), 1.2–1.5 (10H, m), 1.6–1.9 (2H, m), 2.88 (4H, s), 3.84 (3H, s), 4.09 (2H, t, J=6.5 Hz), 7.19 (1H, d, J=8.6 Hz), 7.49 (1H, d, J=2.0 Hz), 7.73 (1H, dd, J=8.6 and 2.0 Hz)

Preparation 86

Succinimido 4-(2-butoxyethoxy)benzoate
IR (Nujol): 1730, 1600, 1250, 1060 cm$^{-1}$
NMR (DMSO-d$_6$, δ): 0.87 (3H, t, J=7.2 Hz), 1.2–1.6 (4H, m), 2.89 (4H, s), 3.46 (2H, t, J=6.3 Hz), 3.73 (2H, t, J=4.4 Hz), 4.25 (2H, t, J=4.4 Hz), 7.18 (2H, d, J=9.0 Hz), 8.04 (2H, d, J=9.0 Hz)

Preparation 87

Succinimido 2-(4-octyloxyphenyl)-2-methoxyacetate
IR (Nujol): 1810, 1740, 1610, 1250, 1210, 1100 cm$^{-1}$
NMR (DMSO-d$_6$, δ): 0.86 (3H, t, J=6.7 Hz), 1.2–1.5 (10H, m), 1.6–1.8 (2H, m), 2.80 (4H, s), 3.35 (3H, s), 3.97 (2H, t, J=6.4 Hz), 5.35 (1H, s), 6.96 (2H, d, J=S.7 Hz), 7.38 (2H, d, J=8.7 Hz)

Preparation 88

O$^4$-Octyl-N-(t-butoxycarbonyl)-D-tyrosine succinimido ester
IR (Nujol): 3370, 1780, 1730, 1700, 1250, 1200 cm$^{-1}$

Preparation 89

Succinimido 2-(4-octyloxyphenyl)-2-methoxyiminoacetate

IR (Nujol): 1800, 1780, 1730, 1600, 1250, 1180, 1130 cm$^{-1}$

NMR (DMSO-d$_6$, δ): 0.86 (3H, t, J=6.6 Hz) 1.2–1.5 (10H, m), 1.6–1.8 (2H, m), 2.89 (4H, s), 4.01 (3H, s), 4.03 (2H, t, J=6.4 Hz), 7.08 (2H, d, J=8.9 Hz), 7.68 (2H, d, J=8.9 Hz)

Preparation 90

N$^T$-Octyl-N-(t-butoxycarbonyl)-L-histidine succinimido ester

IR (Neat): 1810, 1780, 1730, 1500, 1360, 1200, 1160 cm$^{-1}$

Preparation 91

4-Octyloxyphthalic anhydride was obtained from 4-octyloxyphthalic acid according to a similar manner to that of Preparation 5.

IR (Neat): 2910, 2850, 1840, 1760, 1640, 1610, 1290, 1260 cm$^{-1}$

NMR (DMSO-d$_6$, δ): 0.86 (3H, t, J=6.8 Hz), 1.2–1.5 (10H, m), 1.6–1.9 (2H, m), 4.19 (2H, t, J=6.5 Hz), 7.47 (1H, dd, J=8.4 Hz and 2.2 Hz), 7.57 (1H, d, J=2.2 Hz), 7.98 (1H, d, J=8.4 Hz)

Preparation 92

N-Octyloxycarbonyloxysuccinimide was obtained according to a similar manner to that of Preparation 5.

IR (Neat): 2960, 2850, 1780, 1740, 1260, 1230 cm$^{-1}$

NMR (CDCl$_3$, δ): 0.89 (3H, t, J=6.7 Hz), 1.2–1.4 (10H, m), 1.6–1.8 (2H, m), 2.84 (4H, s), 4.32 (2H, t, J=6.7 Hz)

Preparation 93

To a solution of octyl phenyl ether (1.53 g) in chloroform (6 ml) was added chlorosulfonic acid at 0° C. The mixture was stirred at room temperature for 30 minutes, then the mixture was poured into a mixture of water and tetrahydrofuran.

The separated organic layer was washed with sodium chloride aqueous solution, dried over magnesium sulfate and then the solvent was evaporated in vacuo. The residue was subjected to a column chromatography on silica gel to give 4-octyloxyphenylsulfonyl chloride (1.25 g).

IR (Nujol): 1600, 1580, 1500, 1380, 1180 cm$^{-1}$

NMR (CDCl$_3$, δ): 0.89 (3H, t, J=6.6 Hz), 1.20–1.50 (10H, m), 1.80 (2H, m), 4.06 (2H, t, J=6.4 Hz), 7.03 (2H, d, J=9.0 Hz), 7.96 (2H, d, J=9.0 Hz)

The following compounds (Preparations 94 and 95) were obtained according to a similar manner to that of Preparation 5.

Preparation 94

Succinimido 4-(4-heptyloxyphenyl)benzoate

IR (Nujol): 1760, 1740, 1600 cm$^{-1}$

NMR (CDCl$_3$, δ): 0.87 (3H, t, J=6.8 Hz), 1.2–1.7 (8H, m), 1.7–1.9 (2H, m), 2.92 (4H, s), 4.01 (2H, t, J=6.5 Hz), 7.00 (2H, d, J=8.8 Hz), 7.58 (2H, d, J=8.8 Hz), 7.69 (2H, d, J=8.5 Hz), 8.17 (2H, d, J=8.5 Hz)

Preparation 95

Succinimido 4-(4-hexyloxyphenoxy)benzoate

IR (Nujol): 1760, 1120, 1600 cm$^{-1}$

NMR (CDCl$_3$, δ): 0.92 (3H, t, J=6.8 Hz), 1.2–1.5 (6H, m), 1.7–1.9 (2H, m), 2.90 (4H, s), 3.96 (2H, t, J=6.5 Hz), 6.9–7.1 (6H, m), 8.07 (2H, d, J=9 Hz)

In the following, the structures of the compounds of Examples 13 to 53 are shown (SEQ ID NO: 1).

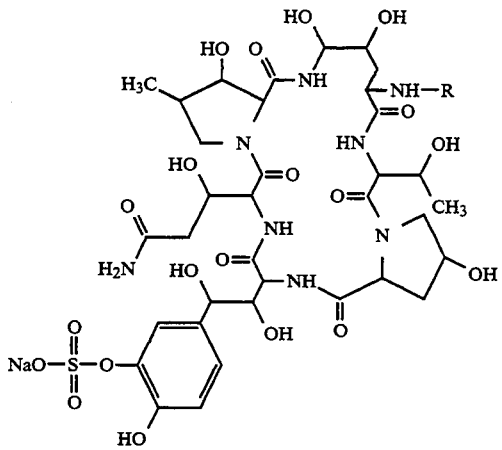

In the following formulae, $^t$Bu means t-butyl, and p-TsOH means p-toluenesulfonic acid.

| Example No. | Compound No. | R |
|---|---|---|
| 13 | FR139835 | —COO(CH$_2$)$_7$CH$_3$ |
| 14 | FR139537 | —CO—⟨C$_6$H$_4$⟩—$^t$Bu |
| 15 | FR141145 | —CO—⟨C$_6$H$_4$⟩—O(CH$_2$)$_2$O(CH$_2$)$_3$CH$_3$ |
| 16 | FR139538 | —CO—⟨C$_6$H$_4$⟩—O(CH$_2$)$_4$—⟨C$_6$H$_5$⟩ |

-continued

| Example No. | Compound No. | R |
|---|---|---|
| 17 | FR140215 | —CO—C₆H₃(COOH)—O(CH₂)₇CH₃ (2-COOH, 5-O(CH₂)₇CH₃ on benzoyl) |
| 18 | FR140216 | —CO—C₆H₃(OCH₃)—O(CH₂)₇CH₃ (3-OCH₃, 4-O(CH₂)₇CH₃ on benzoyl) |
| 19 | FR140727 | —CO—C₆F₄—OCH₂(CF₂)₄H (tetrafluorobenzoyl) |
| 20 | FR143301 | —CO—C₆F₄—OCH₂(CF₂)₆CF₃ (tetrafluorobenzoyl) |
| 21 | FR140495 | —COCH₂—C₆H₄—C₆H₅ (biphenyl) |
| 22 | FR139503 | —COCH(OCH₃)—C₆H₄—O(CH₂)₇CH₃ |
| 23 | FR139500 | —COCH(NHCOO^tBu)CH₂—C₆H₄—O(CH₂)₇CH₃ (D) |
| 24 | FR139501 | —CO—CH(NHCOO^tBu)—(2-naphthyl) (L) |
| 25 | FR139502 | —COCH(NHCOO^tBu)CH₂—[pyrazole-N—(CH₂)₇CH₃] (L) |
| 26 | FR138959 | —CO—C(=NOCH₃)—C₆H₄—O(CH₂)₇CH₃ |

-continued

| Example No. | Compound No. | R |
|---|---|---|
| 27 | FR140291 | —CO—C(=N—O—CH₂—C₆H₄—O(CH₂)₇CH₃)—C₆H₄—OH |
| 28 | FR141580 | —CO—C(=N—O—CH₂—C₆H₄—O(CH₂)₇CH₃)—C₆H₅ |
| 29 | FR141579 | —CO—CH=N—O—CH₂—C₆H₄—O(CH₂)₇CH₃ |
| 30 | FR141146 | CH₃—CO—CH=C(CH₃)—CH₂—CH₂—CH=C(CH₃)—CH₂—CH₂—CH=C(CH₃)₂ |
| 31 | FR140731 | —CO—C₆H₄—(CH₂)₇CH₃ |
| 32 | FR140217 | —CO—C₆H₄—O—C₆H₄—O(CH₂)₇CH₃ |
| 33 | FR142472 | —CO—C₆H₄—C₆H₄—O(CH₂)₇CH₃ |
| 34 | FR140496 | —CO—(naphthyl)—O(CH₂)₃CH₃ |
| 35 | FR140497 | —CO—(naphthyl)—O(CH₂)₅CH₃ |
| 36 | FR143483 | —CO—(naphthyl)—O—CH₂—CH(C₂H₅)—(CH₂)₃CH₃ |

-continued

| Example No. | Compound No. | R |
|---|---|---|
| 37 | FR140728 | —CO—[6-(O(CH$_2$)$_9$CH$_3$)-naphthalen-2-yl] |
| 38 | FR142172 | —CO—[6-(O-CH$_2$CH$_2$CH(CH$_3$)CH$_2$CH$_2$CH$_2$CH(CH$_3$)$_2$)-naphthalen-2-yl] |
| 39 | FR143326 | —CO—[6-(O-CH$_2$CH$_2$CH(CH$_3$)CH$_2$CH$_2$CH=C(CH$_3$)$_2$)-naphthalen-2-yl] |
| 40 | FR142390 | —CO—[6-(O-CH$_2$CH=C(CH$_3$)CH$_2$CH$_2$CH=C(CH$_3$)$_2$)-naphthalen-2-yl] |
| 41 | FR140729 | —CO—[6-(O(CH$_2$)$_{11}$CH$_3$)-naphthalen-2-yl] |
| 42 | FR140730 | —CO—(anthracen-2-yl) |
| 43 | FR143020 | —COCH$_2$—[4-(O(CH$_2$)$_7$CH$_3$)-phenyl] |
| 44 | FR143021 | —CO(CH$_2$)$_2$—[4-(O(CH$_2$)$_7$CH$_3$)-phenyl] |
| 45 | FR141315 | —CO—CH=CH—[4-(O(CH$_2$)$_7$CH$_3$)-phenyl] |
| 46 | FR140105 | —CO—CH(N(CH$_3$)$_2$)CH$_2$—[4-(O(CH$_2$)$_7$CH$_3$)-phenyl] |
| 47 | FR141564 | —SO$_2$—[4-(O(CH$_2$)$_7$CH$_3$)-phenyl] |

-continued

| Example No. | Compound No. | R |
|---|---|---|
| 48 | FR143170 | 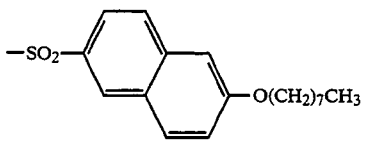 |
| 49 | FR138912 | 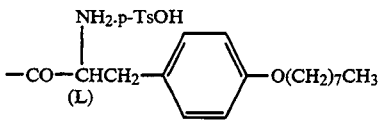 |
| 50 | FR138960 | 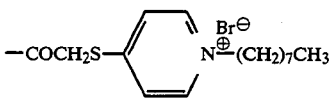 |
| 51 | FR138727 | 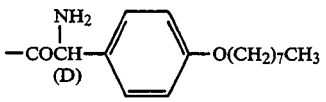 |
| 52 | FR138912 | 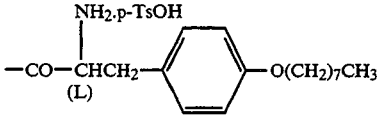 |
| 53 | FR138960 | 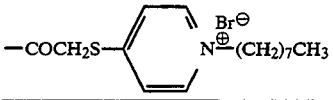 |

EXAMPLE 13

FR139835 substance (SEQ ID NO: 1) was obtained by reacting FR133303 substance (SEQ ID NO: 1) with N-octyloxycarbonyloxysuccinimide according to a similar manner to that of Example 3.
IR (Nujol): 3300, 1620 cm$^{-1}$
FAB-MS e/z=1137 (M+Na)

EXAMPLE 14

FR139537 substance (SEQ ID NO: 1) was obtained by reacting FR133303 substance (SEQ ID NO: 1) with succinimido 4-t-butylbenzoate according to a similar manner to that of Example 3.
IR (Nujol): 3300, 1620 cm$^{-1}$
NMR (D$_2$O, δ): 1.05 (3H, d, J=6.9 Hz), 1.15 (3H, d, J=5.9 Hz), 1.33 (9H, s), 2.0–2.3 (3H, m), 2.4–2.6 (3H, m), 2.7–2.9 (1H, m), 3.4–3.6 (1H, m), 3.8–4.9 (12H, m), 5.07 (2H, m), 5.40 (1H, d, J=3 Hz), 7.06 (1H, d, J=8.2 Hz), 7.08 (1H, dd, J=8.2 Hz and 2 Hz), 7.27 (1H, d, J=2 Hz), 7.60 (1H, d, J=8.6 Hz), 7.75 (1H, d, J=8.6 Hz)

EXAMPLE 15

FR141145 substance (SEQ ID NO: 1) was obtained by reacting FR133303 substance (SEQ ID NO: 1) with succinimido 4-(2-butoxyethoxy)benzoate according to a similar manner to that of Example 3.
IR (Nujol): 3300, 1620 cm$^{-1}$
NMR (DMSO-d$_6$, +D$_2$O, δ): 0.88 (3H, t, J=7.3 Hz), 0.96 (3H, d, J=6.7 Hz), 1.04 (3H, d, J=5.7 Hz), 1.2–1.6 (4H, m), 1.7–2.0 (3H, m), 2.1–2.65 (4H, m), 3.16 (1H, m), 3.7–4.5 (20H, m), 4.78 (1H, d, J=3 Hz), 4.86 (1H, d, J=3.8 Hz), 5.02 (1H, d, J=3 Hz), 6.74 (1H, d, J=8.2 Hz), 6.79 (1H, d, J=8.2 Hz), 7.00 (2H, d, J=8.9 Hz), 7.06 (1H, s), 7.87 (2H, d. J=8.9 Hz)
FAB-MS e/z=1201 (M+Na)

EXAMPLE 16

FR139538 substance (SEQ ID NO: 1) was obtained by reacting FR133303 substance (SEQ ID NO: 1) with succinimido 4-(4-phenylbutoxy)benzoate according to a similar manner to that of Example 3.
IR (Nujol): 3300, 1620 cm$^{-1}$
FAB-MS e/z=1233 (M+Na)

EXAMPLE 17

FR140215 substance (SEQ ID NO: 1) was obtained by reacting FR133303 substance (SEQ ID NO: 1) with 4-octyloxyphthalic anhydride according to a similar manner to that of Example 3.
IR (Nujol): 3300, 1620 cm$^{-1}$
FAB-MS e/z=1257 (M+Na)

EXAMPLE 18

FR140216 substance (SEQ ID NO: 1) was obtained by reacting FR133303 substance (SEQ ID NO: 1) with succinimido 3-methoxy-4-octyloxybenzoate according to a similar manner to that of Example 3.
IR (Nujol): 3300, 1620 cm$^{-1}$
FAB-MS e/z=1243 (M+Na)

EXAMPLE 19

FR140727 substance (SEQ ID NO: 1) was obtained by reacting FR133303 substance (SEQ ID NO: 1) with succinimido 4-(2,2,3,3,4,4,5,5-octafluoropentyloxy)-

2,3,5,6-tetrafluorobenzoate according to a similar manner to that of Example 3.

IR (Nujol): 3300, 1630 cm$^{-1}$
FAB-MS e/z: 1387 (M+Na)

EXAMPLE 20

FR143301 substance (SEQ ID NO: 1) was obtained by reacting FR133303 substance (SEQ ID NO: 1) with succinimido 4-(2,2,3,3,4,4,5,5,6,6,7,7,8,8,8-pentadecafluorooctyloxy)-2,3,5,6-tetrafluorobenzoate according to a similar manner to that of Example 3.

IR (Nujol): 3300, 1630 cm$^{-1}$
FAB-MS e/z=1534 (M+)

EXAMPLE 21

FR140495 substance (SEQ ID NO: 1) was obtained by reacting FR133303 substance (SEQ ID NO: 1) with succinimido 2-(4-biphenylyl)acetate according to a similar manner to that of Example 3.

IR (Nujol): 3300, 1620 cm$^{-1}$
NMR (CD$_3$OD, δ): 1.0–1.1 (6H, m), 1.9–2.2 (3H, m), 2.3–2.6 (3H, m), 2.7–2.85 (1H, m), 3.35 (1H, m), 3.58 (2H, s), 3.65–4.7 (13H, m), 4.93 (1H, d, J=3 Hz), 5.04 (1H, d, J=3.8 Hz), 5.25 (1H, d, J=3 Hz), 6.85 (1H, d, J=8.3 Hz), 7.01 (1H, dd, J=8.3 Hz and 2 Hz), 7.3–7.6 (10H, m)

EXAMPLE 22

FR139503 substance (SEQ ID NO: 1) was obtained by reacting FR133303 substance (SEQ ID NO: 1) with succinimido 2-(4-octyloxyphenyl)-2-methoxyacetate according to a similar manner to that of Example 3.

IR (Nujol): 3330, 1620 cm$^{-1}$
FAB-MS e/z=1257 (M+Na)

EXAMPLE 23

FR139500 substance (SEQ ID NO: 1) was obtained by reacting FR133303 substance (SEQ ID NO: 1) with O$^4$-octyl-N-(t-butoxycarbonyl)-D-tyrosine succinimido ester according to a similar manner to that of Example 3.

IR (Nujol): 3300, 1620 cm$^{-1}$
NMR (CD$_3$OD, δ): 0.90 (3H, t, J=6.8 Hz), 1.06 (3H, d, J=6.8 Hz), 1.17 (3H, d, J=6.7 Hz), 1.20–1.30 (10H, m), 1.35 (9H, s), 1.74 (2H, m), 1.9–2.1 (3H, m), 2.45 (3H, m), 2.76 (1H, m), 3.0–3.1 (1H, m), 3.37 (1H, m), 3.7–4.6 (18H, m), 4.94 (1H, d, J=3 Hz), 5.01 (1H, d, J=3.8 Hz), 5.25 (1H, d, J=3 Hz), 6.79 (2H, d, J=8.5 Hz), 6.83 (1H, d, J=8.3 Hz), 7.03 (1H, dd, J=8.3 Hz and 2 Hz), 7.12 (2H, d, J=8.8 Hz), 7.31 (1H, d, J=2 Hz)

EXAMPLE 24

FR139501 substance (SEQ ID NO: 1) was obtained by reacting FR133303 substance (SEQ ID NO: 1) with N-(t-butoxycarbonyl)-L-2-(2-naphthyl)glycine succinimido ester according to a similar manner to that of Example 3.

IR (Nujol): 3300, 1620 cm$^{-1}$

EXAMPLE 25

FR139502 substance (SEQ ID NO: 1) was obtained by reacting FR133303 substance (SEQ ID NO: 1) with N$^t$-octyl-N-(t-butoxycarbonyl)-L-histidine succinimido ester according to a similar manner to that of Example 3.

IR (Nujol): 3300, 1620 cm$^{-1}$
FAB-MS e/z=1330 (M+Na)

EXAMPLE 26

FR138959 substance (SEQ ID NO: 1) was obtained by reacting FR133303 substance (SEQ ID NO: 1) with succinimido 2-(4-octyloxyphenyl)-2-methoxyiminoacetate according to a similar manner to that of Example 3.

IR (Nujol): 3300, 1620 cm$^{-1}$
NMR (CD$_3$OD, δ): 0.91 (3H, t, J=6.6 Hz), 1.06 (3H, d, J=6.8 Hz), 1.25 (3H, d, J=6.3 Hz), 1.25–1.6 (10H, m), 1.65–1.9 (2H, m), 1.9–2.2 (3H, m), 2.3–2.65 (3H, m), 1.75–1.9 (1H, m), 3.3–3.5 (1H, m), 3.95 (3H, s), 3.7–4.75 (16H, m), 5.03 (1H, d, J=3.0 Hz), 5.11 (1H, d, J=3.7 Hz), 5.46 (1H, d, J=2.7 Hz), 6.86 (1H, d, J=8.2 Hz), 6.89 (2H, d, J=8.9 Hz), 7.01 (1H, dd, J=8.2 Hz and 2 Hz), 7.31 (1H, d, J=2 Hz), 7.54 (2H, d, J=8.9 Hz)
FAB-MS e/z=1270 (M+Na)

EXAMPLE 27

FR140291 substance (SEQ ID NO: 1) was obtained by reacting FR133303 substance (SEQ ID NO: 1) with succinimido 2-(4-hydroxyphenyl)-2-(4-octyloxybenzyloxyimino)acetate according to a similar manner to that of Example 3.

IR (Nujol): 3250, 1650, 1620 cm$^{-1}$
FAB-MS e/z=1363 (M+Na)

EXAMPLE 28

FR141580 substance (SEQ ID NO. 1) was obtained by reacting FR133303 substance (SEQ ID NO. 1) with succinimido 2-phenyl-2-(4-octyloxybenzyloxyimino)acetate according to a similar manner to that of Example 3.

IR (Nujol): 3300, 1646 cm$^{-1}$
FAB-MS e/z=1346 (M+Na)

EXAMPLE 29

FR141579 substance (SEQ ID NO: 1) was obtained by reacting FR133303 substance (SEQ ID NO: 1) with succinimido 2-(4-octyloxybenzyloxyimino)acetate according to a similar manner to that of Example 3.

IR (Nujol): 3250, 1650 cm$^{-1}$
FAB-MS e/z=1270 (M+Na)

EXAMPLE 30

FR141146 substance (SEQ ID NO: 1) was obtained by reacting FR133303 substance (SEQ ID NO: 1) with 1-[(2E,6E)-3,7,11-trimethyl-2,6,10-dodecatrienoyl]-1H-benzotriazole-3-oxide according to a similar manner to that of Example 12.

IR (Nujol): 3300, 1620, 1040 cm$^{-1}$
NMR (CD$_3$OD, δ): 1.06 (3H, d, J=6.8 Hz), 1.19 (3H, d, J=5.9 Hz), 1.60 (3H, s), 1.62 (3H, s), 1.66 (3H, s), 1.9–2.2 (11H, m), 2.05 (3H, s), 2.3–2.6 (3H, m), 2.7–2.9 (1H, m), 3.35 (1H, m), 3.7–5.0 (14H, m), 5.08 (4H, m), 5.27 (1H, d, J=2.8 Hz), 5.77 (1H, s), 6.86 (1H, d, J=8.3 Hz), 7.04 (1H, dd, J=8.3 Hz and 1.9 Hz), 7.32 (1H, d, J=1.9 Hz)

EXAMPLE 31

FR140731 substance (SEQ ID NO: 1) was obtained by reacting FR133303 substance (SEQ ID NO: 1) with 1-(4-octylbenzoyl)-1H-benzotriazole-3-oxide according to a similar manner to that of Example 12.

IR (Nujol): 3300, 1620, 1040 cm$^{-1}$
NMR (CD$_3$OD, δ): 0.86 (3H, t, J=6.8 Hz), 1.06 (3H, d, J=6.8 Hz), 1.21 (3H, d, J=5.8 Hz), 1.25–1.45 (10H, m), 1.55–1.75 (2H, m), 1.9–2.25 (3H, m), 2.35–2.6 (3H, m), 2.65 (2H, t, J=7.5 Hz), 2.81 (1H, m), 3.32 (1H, m), 3.7–4.8 (14H, m), 4.98 (1H, d, J=3 Hz), 5.09 (1H, d, J=3.9 Hz), 5.31 (1H, d, J=3 Hz), 6.86 (1H, d, J=8.3 Hz), 7.03 (1H, dd, J=8.3 Hz and 2 Hz), 7.24 (2H, d, J=8.2 Hz), 7.33 (1H, d, J=2 Hz), 7.74 (2H, d, J=8.2 Hz)

FAB-MS e/z=1197 (M+Na)

EXAMPLE 32

FR140217 substance (SEQ ID NO: 1) was obtained by reacting FR133303 substance (SEQ ID NO: 1) with 1-[4-(4-octyloxy)phenoxy]benzoyl-1H-benzotriazole-3-oxide according to a similar manner to that of Example 12.

IR (Nujol): 3300, 1620 cm$^{-1}$
FAB-MS e/z=1305 (M+Na)

EXAMPLE 33

FR142472 substance (SEQ ID NO: 1) was obtained by reacting FR133303 substance (SEQ ID NO: 1) with 1-[4-(4-octyloxyphenyl)benzoyl]-1H-benzotriazole-3-oxide according to a similar manner to that of Example 12.

IR (Nujol): 3300, 1620 cm$^{-1}$
NMR (CD$_3$OD, δ): 0.88 (3H, t, J=6.7 Hz), 1.06 (3H, d, J=6.8 Hz), 1.23 (3H, d, J=6.1 Hz), 1.3–1.6 (10H, m), 1.8–1.9 (2H, m), 1.9–2.3 (3H, m), 2.3–2.7 (3H, m), 2.9–3.0 (1H, m), 3.39 (1H, m), 3.7–4.7 (16H, m), 4.99 (1H, d, J=3.0 Hz), 5.10 (1H, d, J=3.7 Hz), 5.35 (1H, d, J=2.7 Hz), 6.87 (1H, d, J=8.3 Hz), 6.99 (2H, d, J=8.8 Hz), 7.04 (1H, dd, J=8.3 Hz and 1.9 Hz), 7.33 (1H, d, J=1.9 Hz), 7.58 (2H, d, J=8.8 Hz), 7.62 (2H, d, J=8.4 Hz), 7.87 (2H, d, J=8.4 Hz)

FAB-MS e/z=1289 (M+Na)

EXAMPLE 34

FR140496 substance (SEQ ID NO: 1) was obtained by reacting FR133303 substance (SEQ ID NO: 1) with 1-(6-butoxy-2-naphthoyl)-1H-benzotriazole-3-oxide according to a similar manner to that of Example 12.

IR (Nujol): 3300, 1620 cm$^{-1}$
FAB-MS e/z=1207 (M+Na)

EXAMPLE 35

FR140497 substance (SEQ ID NO: 1) was obtained by reacting FR133303 substance (SEQ ID NO: 1) with 1-(6-hexyloxy-2-naphthoyl)-1H-benzotriazole-3-oxide according to a similar manner to that of Example 12.

IR (Nujol): 3300, 1620 cm$^{-1}$
NMR (DMSO-d$_6$+D$_2$O, δ): 0.89 (3H, t, J=6.6 Hz), 0.97 (3H, d, J=6.9 Hz), 1.08 (3H, d, J=5.9 Hz), 1.2–1.6 (6H, m), 1.7–2.1 (5H, m), 2.1–2.5 (3H, m), 2.5–2.7 (1H, m), 3.19 (1H, m), 3.73 (2H, m), 3.8–4.5 (12H, m), 4.80 (1H, d, J=3 Hz), 4.88 (1H, d, J=3.8 Hz), 5.08 (1H, d, J=3 Hz), 6.74 (1H, d, J=8.2 Hz), 6.80 (1H, dd, J=8.2 Hz and 2 Hz), 7.08 (1H, d, J=2 Hz), 7.26 (1H, dd, J=8.9 Hz and 2.4 Hz), 7.39 (1H, d, J=2.4 Hz), 7.85 (1H, d, J=8.7 Hz), 7.89 (1H, d, J=8.7 Hz), 7.93 (1H, d, J=8.9 Hz), 8.44 (1H, s)

FAB-MS e/z=1236 (M+Na)

EXAMPLE 36

FR143483 substance (SEQ ID NO: 1) was obtained by reacting FR133303 substance (SEQ ID NO: 1) with 1-[6-(2-ethylhexyloxy)-2-naphthoyl]-1H-benzotriazole-3-oxide according to a similar manner to that of Example 12.

IR (Nujol): 3250, 1620 cm$^{-1}$
NMR (CD$_3$OD, δ): 0.93 (3H, t, J=7.4 Hz), 0.98 (3H, t, J=7.4 Hz), 1.06 (3H, d, J=6.8 Hz), 1.24 (3H, d, J=6.0 Hz), 1.3–1.7 (8H, m), 1.7–1.9 (1H, m), 1.9–2.3 (3H, m), 2.3–2.7 (3H, m), 2.8–3.0 (1H, m), 3.39 (1H, m), 3.7–4.7 (16H, m), 5.00 (1H, d, J=4.4 Hz), 5.11 (1H, d, J=3.7 Hz), 5.37 (1H, d, J=2.6 Hz), 6.87 (1H, d, J=8.3 Hz), 7.04 (1H, dd, J=8.3 Hz and 2 Hz), 7.17 (1H, dd, J=8.9 Hz and 1.9 Hz), 7.22 (1H, d, J=2 Hz), 7.33 (1H, d, J=1.9 Hz), 7.7–7.9 (3H, m), 8.29 (1H, s)

FAB-MS e/z=1263 (M+Na)

EXAMPLE 37

FR140728 substance (SEQ ID NO: 1) was obtained by reacting FR133303 substance (SEQ ID NO: 1) with 1-(6-decyloxy-2-naphthoyl)-1H-benzotriazole-3-oxide according to a similar manner to that of Example 12.

IR (Nujol): 3300, 1620 cm$^{-1}$
NMR (DMSO-d$_6$+D$_2$O, δ): 0.86 (3H, t, J=6.6 Hz), 0.97 (3H, d, J=6.7 Hz), 1.07 (3H, d, J=5.9 Hz), 1.2–1.6 (14H, m), 1.7–2.1 (5H, m), 2.1–2.5 (3H, m), 2.5–2.7 (1H, m), 3.19 (1H, m), 3.45 (1H, m), 3.73 (2H, m), 3.9–4.5 (12H, m), 4.79 (1H, d, J=3 Hz), 4.87 (1H, d, J=3.8 Hz), 5.07 (1H, d, J=3 Hz), 6.74 (1H, d, J=8.2 Hz), 6.79 (1H, dd, J=8.1 Hz and 2 Hz), 7.06 (1H, d, J=2 Hz), 7.23 (1H, dd, J=8.9 Hz and 2.4 Hz), 7.38 (1H, J=2.4 Hz), 7.85 (1H, d, J=8.7 Hz), 7.89 (1H, J=8.7 Hz), 7.93 (1H, d, J=8.9 Hz), 8.45 (1H, s)

FAB-MS e/z=1291 (M+Na)

EXAMPLE 38

FR142172 substance (SEQ ID NO: 1) was obtained by reacting FR133303 substance (SEQ ID NO: 1) with 1-[6-(3,7-dimethyloctyloxy)-2-naphthoyl]-1H-benzotriazole-3-oxide according to a similar manner to that of Example 12.

IR (Nujol): 3300, 1610 cm$^{-1}$
NMR (DMSO-d$_6$+D$_2$O, δ): 0.85 (6H, d, J=6.6 Hz), 0.95 (3H, d, J=5.9 Hz), 0.97 (3H, d, J=6.7 Hz), 1.08 (3H, d, J=5.9 Hz), 1.1–1.4 (6H, m), 1.4–2.1 (7H, m), 2.1–2.5 (3H, m), 2.5–2.7 (1H, m), 3.19 (1H, m), 3.74 (2H, m), 3.9–4.6 (12H, m), 4.81 (1H, d, J=3 Hz), 4.87 (1H, d, J=3.8 Hz), 5.07 (1H, d, J=3 Hz), 6.74 (1H, d, J=8.2 Hz), 6.83 (1H, dd, J=8.1 Hz and 2 Hz), 7.06 (1H, d, J=2 Hz), 7.23 (1H, dd, J=8.9 Hz and 2.4 Hz), 7.40 (1H, d, J=2.4 Hz), 7.85 (1H, d, J=8.7 Hz), 7.89 (1H, d, J=8.7 Hz), 7.93 (1H, d, J=8.9 Hz), 8.45 (1H, s)

FAB-MS e/z=1291 (M+Na)

EXAMPLE 39

FR143326 substance (SEQ ID NO: 1) was obtained by reacting FR133303 substance (SEQ ID NO: 1) with 1-[6-(3,7-dimethyl-6-octenyloxy)-2-naphthoyl]-1H-benzotriazole-3-oxide according to a similar manner to that of Example 12.

IR (Nujol): 3300, 1620, 1260, 1040 cm$^{-1}$
NMR (CD$_3$OD, δ): 1.00 (3H, d, J=6.2 Hz), 1.06 (3H, d, J=6.8 Hz), 1.25 (3H, d, J=5.9 Hz), 1.2–1.6 (2H, m), 1.61 (3H, s), 1.67 (3H, s), 1.63–2.3 (8H, m), 2.3–2.7 (3H, m), 2.8–3.0 (1H, m), 3.39 (1H, m), 3.7–4.8 (16H, m), 5.00 (1H, d, J=5.1 Hz), 5.08–5.2 (2H, m), 5.37 (1H, d, J=2.5 Hz), 6.87 (1H, d, J=8.3 Hz), 7.04 (1H, d, J=8.3 Hz), 7.15 (1H, d, J=8.9 Hz), 7.21 (1H, s), 7.33 (1H, s), 7.71 (1H, d, J=8.7 Hz), 7.77–7.85 (2H, m), 8.28 (1H, s)

EXAMPLE 40

FR142390 substance (SEQ ID NO: 1) was obtained by reacting FR133303 substance (SEQ ID NO: 1) with 1-[6-{(E)-3,7-dimethyl-2,6-octadienyloxy}-2-naphthoyl]-1H-benzotriazole-3-oxide according to a similar manner to that of Example 12.

IR (Nujol): 3300, 1620 cm$^{-1}$

NMR (DMSO-d$_6$+D$_2$O, δ): 0.97 (3H, d, J=6.7 Hz), 1.07 (3H, d, J=6.0 Hz), 1.57 (3H, s), 1.61 (3H, s), 1.76 (3H, s), 1.8-2.5 (9H, m), 2.5-2.7 (1H, m), 3.19 (1H, m), 3.45 (1H, m), 3.73 (2H, m), 3.9-4.6 (11H, m), 4.70 (2H, d, J=6.5 Hz), 4.80 (1H, d, J=3 Hz), 4.87 (1H, d, J=3.8 Hz), 5.07 (2H, m), 5.51 (1H, t, J=6.5 Hz), 6.74 (1H, d, J=8.3 Hz), 6.83 (1H, dd, J=8.3 Hz and 2 Hz), 7.07 (1H, d, J=2 Hz), 7.24 (1H, dd, J=8.9 Hz and 2.4 Hz), 7.40 (1H, d, J=2.4 Hz), 7.8-8.0 (3H, m), 8.45 (1H, s)

FAB-MS e/z=1287 (M+Na)

EXAMPLE 41

FR140729 substance (SEQ ID NO: 1) was obtained by reacting FR133303 substance (SEQ ID NO: 1) with 1-(6-dodecyloxy-2-naphthoyl)-1H-benzotriazole-3-oxide according to a similar manner to that of Example 12.

IR (Nujol): 3300, 1610 cm$^{-1}$

NMR (DMSO-d$_6$+D$_2$O, δ): 0.85 (3H, t, J=6.6 Hz), 0.97 (3H, d, J=6.7 Hz), 1.07 (3H, d, J=5.9 Hz), 1.2-1.6 (18H, m), 1.7-2.1 (5H, m), 2.1-2.5 (3H, m), 2.5-2.7 (1H, m), 3.19 (1H, m), 3.45 (1H, m), 3.73 (2H, m), 3.9-4.5 (12H, m), 4.79 (1H, d, J=3 Hz), 4.87 (1H, d, J=3.8 Hz), 5.07 (1H, d, J=3 Hz), 6.74 (1H, d, J=8.1 Hz), 6.78 (1H, dd, J=8.1 Hz and 2 Hz), 7.06 (1H, d, J=2 Hz), 7.23 (1H, dd, J=8.9 Hz and 2.4 Hz), 7.38 (1H, d, J=2.4 Hz), 7.85 (1H, d, J=8.7 Hz), 7.89 (1H, d, J=8.7 Hz), 7.93 (1H, d, J=8.9 Hz), 8.44 (1H, s)

FAB-MS e/z=1320 (M+Na)

EXAMPLE 42

FR140730 substance (SEQ ID NO: 1) was obtained by reacting FR133303 substance (SEQ ID NO: 1) with 1-(2-anthrylcarbonyl)-1H-benzotriazole-3oxide according to a similar manner to that of Example 12.

IR (Nujol): 3300, 162.0 cm$^{-1}$

FAB-MS e/z=1.185 (M+Na)

EXAMPLE 43

FR143020 substance (SEQ ID NO: 1) was obtained by reacting FR133303 substance (SEQ ID NO: 1) with 1-[2-(4-octyloxyphenyl)acetyl]-1H-benzotriazole-3-oxide according to a similar manner to that of Example 12.

IR (Nujol): 3300, 1620 cm$^{-1}$

NMR (CD$_3$OD, δ): 0.87 (3H, t, J=6.8 Hz), 1.0-1.2 (6H, m), 1.2-1.6 (10H, m), 1.6-1.85 (2H, m), 1.85-2.1 (3H, m), 2.3-2.6 (3H, m), 2.7-2.85 (1H, m), 3.32 (1H, m), 3.46 (2H, s), 3.7-4.7 (16H, m), 5.04 (1H, d, J=3.7 Hz), 5.23 (1H, d, J=2.7 Hz), 6.75-6.9 (3H, m), 7.01 (1H, d, J=8.3 Hz), 7.15 (2H, d, J=8.5 Hz), 7.30 (1H, s)

FAB-MS e/z=1227 (M+Na)

EXAMPLE 44

FR143021 substance (SEQ ID NO: 1) was obtained by reacting FR133303 substance (SEQ ID NO: 1) with 1-[3-(4-octyloxyphenyl)propionyl]-1H-benzotriazole-3-oxide according to a similar manner to that of Example 12.

IR (Nujol): 3300, 162.0 cm$^{-1}$

FAB-MS e/z=1241 (M+Na)

EXAMPLE 45

FR141315 substance (SEQ ID NO: 1) was obtained by reacting FR133303 substance (SEQ ID NO: 1) with 1-[(E)-3-(4-octyloxyphenyl)acryloyl]-1H-benzotriazole-3-oxide according to a similar manner to that of Example 12.

IR (Nujol): 3300, 1620 cm$^{-1}$

NMR (DMSO-d$_6$+D$_2$O, δ): 0.86 (3H, t, J=6.7 Hz), 0.97 (3H, d, J=6.7 Hz), 1.04 (3H, d, J=5.4 Hz), 1.2-1.5 (10H, m), 1.6-2.0 (5H, m), 2.1-2.5 (3H, m), 2.5-2.6 (1H, m), 3.17 (1H, m), 3.3-4.5 (15H, m), 4.79 (1H, d, J=3 Hz), 4.86 (1H, d, J=3.8 Hz), 5.01 (1H, d, J=3 Hz), 6.57 (1H, d, J=15.8 Hz), 6.74 (1H, d, J=8.2 Hz), 6.82 (1H, d, J=8.2 Hz), 6.97 (2H, d, J=8.8 Hz), 7.09 (1H, s), 7.34 (1H, d, J=15.8 Hz), 7.52 (2H, d, J=8.8 Hz)

FAB-MS e/z=1239 (M+Na)

EXAMPLE 46

FR140105 substance (SEQ ID NO: 1) was obtained by reacting FR133303 substance (SEQ ID NO: 1) with 1-(O$^4$-octyl-N,N-dimethyl-L-tyrosyl)-1H-benzotriazole-3-oxide according to a similar manner to that of Example 12.

IR (Nujol): 3300, 1620 cm$^{-1}$

NMR (CD$_3$OD, δ): 0.91 (3H, t, J=6.8 Hz), 1.06 (3H, d, J=6.8 Hz), 1.12 (3H, d, J=6.1 Hz), 1.33 (10H, m), 1.74 (2H, m), 1.98 (3H, m), 2.40 (6H, s), 2.3-2.6 (3H, m), 2.8 (2H, m), 2.9-3.1 (1H, m), 3.3-3.5 (2H, m), 3.6-4.7 (16H, m), 5.06 (1H, d, J=3.8 Hz), 5.33 (1H, d, J=3 Hz), 6.77 (2H, d, J=8.6 Hz), 6.86 (1H, d, J=8.3 Hz), 7.03 (1H, dd, J=8.3 Hz and 2 Hz), 7.07 (2H, d, J=8.6 Hz), 7.31 (1H, d, J=2 Hz)

EXAMPLE 47

FR141564 substance was obtained by reacting FR133303 substance with 4-octyloxyphenylsulfonyl chloride according to a similar manner to that of Example 6.

IR (Nujol): 3300, 1620 cm$^{-1}$

NMR (DMSO-d$_6$+D$_2$O, δ): 0.87 (3H, t, J=6.7 Hz), 0.97 (3H, d, J=6.8 Hz), 1.04 (3H, d, J=5.7 Hz), 1.1-1.5 (10H, m), 1.6-2.1 (5H, m), 2.45 (3H, m), 2.5-2.7 (1H, m), 3.19 (1H, m), 3.7-4.5 (16H, m), 4.80 (1H, d, J=3 Hz), 4.88 (1H, d, J=4 Hz), 5.08 (1H, d, J=3 Hz), 6.74 (1H, d, J=8.2 Hz), 6.82 (1H, d, J=8.2 Hz), 6.84 (2H, d, J=8.7 Hz), 7.07 (1H, s), 7.51 (2H, d, J=8.7 Hz)

FAB-MS e/z=1249 (M+Na)

EXAMPLE 48

FR143170 substance was obtained by reacting FR133303 substance with 6-octyloxy-2-naphthylsulfonyl chloride according to a similar manner to that of Example 6.

IR (Nujol): 3300, 1620 cm$^{-1}$

NMR (CD$_3$OD, δ): 0.29 (3H, d, J=6.0 Hz), 0.91 (3H, t, J=6.7 Hz), 1.07 (3H, d, J=6.9 Hz), 1.25-1.6 (10H, m), 1.7-2.2 (5H, m), 2.2-2.6 (4H, m), 3.37 (1H, m), 3.55-4.65 (17H, m), 4.97 (1H, m), 5.54 (1H, m), 6.84 (1H, d, J=8.3 Hz), 7.01 (1H, dd, J=8.4 Hz and 2 Hz), 7.15-7.3 (3H, m), 7.75-8.0 (3H, m), 8.35 (1H, s)

FAB-MS e/z=1299 (M+Na)

EXAMPLE 49

To a solution of FR138364 substance (SEQ ID NO: 1) obtained in Example 5 (0.24 g) in acetonitrile (5 ml) was added p-toluenesulfonic acid (0.132 g) and stirred for 8 hours at room temperature. The reaction mixture was added to water and the aqueous layer was adjusted to pH 4.5 with saturated sodium bicarbonate aqueous solution. The aqueous solution was subjected to column chromatography on Diaion HP-20 and eluted with 80% aqueous methanol. The fractions containing the object compound were combined and evaporated under reduced pressure to remove methanol. The residue was lyophilized to give FR138912 substance (SEQ ID NO: 1) (0.15 g).

IR (Nujol): 3300, 1620 cm$^{-1}$
FAB-MS e/z=1272 (M+K)

EXAMPLE 50

The mixture of FR138728 substance (SEQ ID NO: 1) obtained in Example 8 (0.15 g) and 1-octyl-1,4-dihydropyridine-4-thione (0.031 g) in N,N-dimethylformamide was stirred for 1.5 hours under ice-cooling. The reaction mixture was pulverized with diethyl ether (50 ml). The precipitate was filtrated and dried over phosphorus pentoxide under reduced pressure. The powder was added to water (300 ml) and adjusted to pH 4.5. The aqueous solution was subjected to column chromatography on Diaion HP-20 (50 ml) and eluted with 80% aqueous methanol. The fractions containing the object compound were combined and evaporated under reduced pressure to remove methanol. The residue was lyophilized to give FR138960 substance (SEQ ID NO: 1) (0.15 g).

IR (Nujol): 3300, 1620 cm$^{-1}$
FAB-MS e/z=1222 (Free M+Na)

The following compounds (Examples 51 to 53) were obtained according to a similar manner to that of Example 3.

EXAMPLE 51

FR138727 substance (SEQ ID NO: 1)
NMR (CD$_3$OD, δ): 0.90 (3H, t, J=6.8 Hz), 1.05 (3H, d, J=6.8 Hz), 1.17–1.33 (13H, m), 1.6–1.8 (2H, m), 1.9–2.1 (3H, m), 2.50 (1H, m), 2.75 (1H, dd, J=16 Hz and 4 Hz), 3.40 (1H, m), 3.7–3.8 (1H, m), 3.98 (2H, t, J=6.2 Hz), 3.9–4.2 (5H, m), 4.3–4.5 (5H, m), 4.5–4.7 (3H, m), 4.97 (1H, d, J=3 Hz), 5.06 (1H, s), 5.20 (1H, d, J=3 Hz), 5.40 (1H, d, J=3 Hz), 6.85 (1H, d, J=8.3 Hz), 6.95 (2H, d,, J=8.5 Hz), 7.02 (1H, d, J=8.3 Hz), 7.30 (1H, d, J=8.5 Hz), 7.44 (1H, s)

EXAMPLE 52

FR138912 substance
IR (Nujol): 3300, 1620 cm$^{-1}$

EXAMPLE 53

FR138960 substance
IR (Nujol): 3300, 1620 cm$^{-1}$

In the following, the structures of the compounds of Example 54 and 55 are shown (SEQ ID NO: 1).

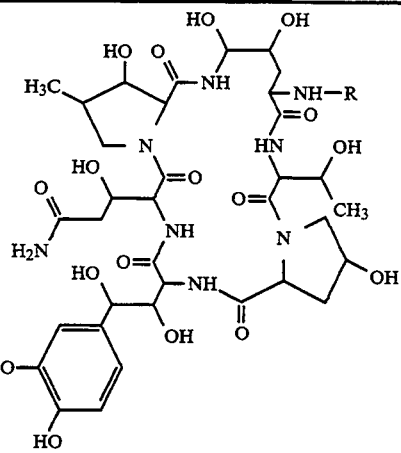

| Example No. | Compound No. | R |
|---|---|---|
| 54 | FR144274 | —CO—⌬—⌬—O(CH$_2$)$_6$CH$_3$ |
| 55 | FR144271 | —CO—⌬—O—⌬—O(CH$_2$)$_5$CH$_3$ |

The following compounds (Examples 54 and 55) were obtained according to a similar manner to that of Example 3.

EXAMPLE 54

FR144274
IR (Nujol): 3300, 1620 cm$^{-1}$
Anal. Calcd. for $C_{55}H_{73}N_8SO_{22}Na$ 6H$_2$O C: 48.53, H: 6.29, N: 8.23, S: 2.35 Found C: 48.36, H: 6.34, N: 8.15, S: 2.30
FAB-MS e/z 1275 (M+Na)

EXAMPLE 55

FR144271
Anal. Calcd. for $C_{54}H_{71}N_8SO_{23}Na$ 6H$_2$O C: 47.57, H: 6.14, N: 8.22, S: 2.35 Found C: 47.58, H: 6.05, N: 8.18, S: 2.27
FAB-MS e/z=1277 (M+Na)

What we claim is:

1. A polypeptide compound having antimicrobial activity of the following formula:

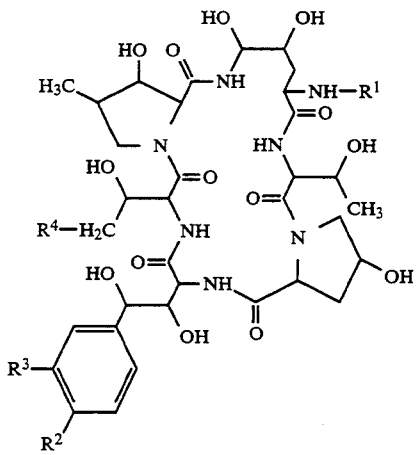

wherein
   $R^1$ is a hydrogen or acyl group,
   $R^2$ is hydroxy or acyloxy,
   $R^3$ is hydroxysulfonyloxy, and
   $R^4$ is hydrogen or carbamoyl,
with proviso that
   $R^1$ is not palmitoyl, when $R^2$ is hydroxy,
   $R^3$ is hydroxysulfonyloxy and
   $R^4$ is carbamoyl,
and a salt thereof.

2. A polypeptide compound of claim 1, which is shown by the following formula (SEQ ID NO: 1):

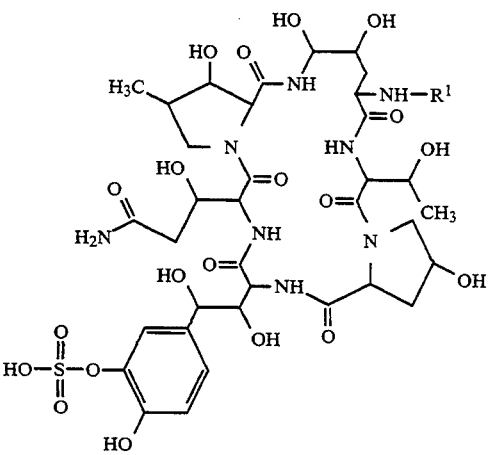

wherein $R^1$ is as defined above.

3. A compound of claim 2, wherein $R^1$ is lower alkanoyl which may have one or more suitable substituent(s); higher alkanoyl, lower alkenoyl which may have one or more suitable substituent(s); higher alkenoyl; lower alkoxycarbonyl; higher alkoxycarbonyl; aryloxycarbonyl; arylglyoxyloyl; ar(lower)alkoxycarbonyl which may have one or more suitable substituent(s); lower alkylsulfonyl; arylsulfonyl which may have one or more suitable substituent(s); ar(lower)alkylsulfonyl; or aroyl which may have one or more suitable substituent(s).

4. A compound of claim 3, wherein $R^1$ is lower alkanoyl; halo(lower)alkanoyl; ar(lower)alkanoyl which may have 1 to 3 suitable substituent(s) selected from the group consisting of hydroxy, lower alkoxy, higher alkoxy, aryl, amino, protected amino, di(lower)alkylamino, lower alkoxyimino and ar(lower)alkoxyimino which may have 1 to 3 higher alkoxy; heterocyclicthio(lower)alkanoyl which may have 1 to 3 higher alkyl; heterocyclic(lower)alkanoyl which may have 1 to 3 suitable substituent(s) selected from the group consisting of lower alkoxyimino, higher alkyl, amino and protected amino; ar(lower)alkoxyimino(lower)alkanoyl which may have 1 to 3 higher alkoxy; higher alkanoyl; ar(lower)alkenoyl which may have 1 to 3 higher alkoxy; higher alkenoyl; lower alkoxycarbonyl; higher alkoxycarbonyl;

aryloxycarbonyl; arylsulfonyl which may have 1 to 3 suitable substituent(s) selected from the group consisting of lower alkyl and higher alkoxy; or aroyl which may have 1 to 5 suitable substituent(s) selected from the group consisting of halogen, lower alkyl, higher alkyl, carboxy, lower alkoxy which may have 1 to 10 halogen, lower alkoxy(lower)alkoxy, ar(lower)alkoxy, higher alkoxy which may have 1 to 17 halogen, higher alkenyloxy, aryl which may have 1 to 3 higher alkoxy and aryloxy which may have 1 to 3 lower alkoxy or higher alkoxy.

5. A compound of claim 4, wherein $R^1$ is lower alkanoyl; halo(lower)alkanoyl; phenyl(lower)alkanoyl or naphthyl(lower)alkanoyl, each of which may have 1 to 3 suitable substituent(s) selected from the group consisting of hydroxy, lower alkoxy, higher alkoxy, phenyl, amino, lower alkoxycarbonylamino, di(lower)alkylamino, lower alkoxyimino and phenyl(lower)alkoxyimino which may have 1 to 3 higher alkoxy;

pyridylthio(lower)alkanoyl which may have 1 to 3 higher alkyl; imidazolyl(lower)alkanoyl or thiazolyl(lower)alkanoyl, each of which may have 1 to 3 suitable substituent(s) selected from the group consisting of lower alkoxyimino, higher alkyl, amino and lower alkoxycarbonylamino;

phenyl(lower)alkoxyimino(lower)alkanoyl which may have 1 to 3 higher alkoxy; higher alkanoyl;

phenyl(lower)alkenoyl which may have 1 to 3 higher alkoxy; higher alkenoyl; lower alkoxycarbonyl, higher alkoxycarbonyl; phenoxycarbonyl; phenylsulfonyl or naphthylsulfonyl, each of which may have 1 to 3 suitable substituent(s) selected from the group consisting of lower alkyl and higher alkoxy; or, benzoyl, naphthoyl or anthrylcarbonyl, each of which may have 1 to 5 suitable substituent(s) selected from the group consisting of halogen, lower alkyl, higher alkyl, carboxy, lower alkoxy, which may have 6 to 10 halogen, lower alkoxy(lower)alkoxy, phenyl(lower)alkoxy, higher alkoxy which may have 12 to 17 halogen, higher alkenyloxy, phenyl which may have 1 to 3 higher alkoxy, and phenoxy which may have 1 to 3 lower alkoxy or higher alkoxy.

6. A compound of claim 5, wherein $R^1$ is phenyl(lower)alkenoyl which may have 1 to 3 higher alkoxy; or benzoyl, naphthoyl or anthrylcarbonyl, each of which may have 1 to 5 suitable substituent(s) selected from the group consisting of halogen, lower alkyl, higher alkyl, carboxy, lower alkoxy which may have 6 to 10 halogen, lower alkoxy(lower)alkoxy, phenyl(lower)alkoxy, higher alkoxy which may have 12 to 17 halogen, higher alkenyloxy, phenyl which may have 1 to 3 higher alkoxy, and phenoxy which may have 1 to 3 lower alkoxy or higher alkoxy.

7. A compound of claim 6, wherein $R^1$ is phenyl(lower)alkenoyl which may have higher alkoxy; or benzoyl or naphthoyl, each of which may have higher alkoxy, higher alkenyloxy, or phenyl which may have higher alkoxy.

8. A compound of claim 7, wherein $R^1$ is benzoyl which has higher alkoxy.

9. A compound of claim 8, wherein $R^1$ is 4-octyloxybenzoyl.

10. A compound of Claim 7, wherein $R^1$ is phenyl(lower)alkenoyl which has higher alkoxy; or naphthoyl which was higher alkoxy or higher alkenyloxy.

11. A pharmaceutical composition having antimicrobial activity which comprises an effective amount of a compound of claim 1 or a pharmaceutically acceptable salt thereof in admixture with a pharmaceutically acceptable carrier or excipient.

* * * * *

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
       (A) LENGTH: 6 amino acids
       (B) TYPE: amino acid
       (D) TOPOLOGY: circular (ii) MOLECULE TYPE: protein (xi) SEQUENCE DESCRIPTION: SEQ ID NO:1:

Xaa Thr Xaa Xaa Xaa Xaa
   1               5